(12) United States Patent  (10) Patent No.: US 6,403,561 B1
Rose et al.  (45) Date of Patent: Jun. 11, 2002

(54) TRIPEPTIDYLPEPTIDASE INHIBITORS

(75) Inventors: Christiane Rose, Le Mesnil St Denis; Froylan Vargas, Paris; Pierre Bourgeat, Paris; Jean-Charles Schwartz, Paris, all of (FR); Paul Beaumont Bishop, London (GB); Ramesh B. Bambal, Lawrence, KS (US); Charon Robin Ganellin, Wedwyn Herts (GB); Bertrand Leblond, Rouen (FR); Andrew N. J. Moore, Jerusalem (IL); Lihua Zhao, London; Suzanne Chan, Bexleyreath, both of (GB)

(73) Assignee: Institut National de la Sante et de la Recherche Medicale (Inserm) (FR)

( * ) Notice: Subject to any disclaimer, the term of this patent is extended or adjusted under 35 U.S.C. 154(b) by 0 days.

(21) Appl. No.: 08/930,055

(22) PCT Filed: May 9, 1996

(86) PCT No.: PCT/FR96/00700

§ 371 (c)(1),
(2), (4) Date: Feb. 19, 1998

(87) PCT Pub. No.: WO96/35805

PCT Pub. Date: Nov. 14, 1996

(51) Int. Cl.$^7$ .............................................. C07K 5/062
(52) U.S. Cl. ........................ 514/19; 562/553; 562/575; 540/476
(58) Field of Search ........................ 540/476; 562/575, 562/553; 514/19

(56) References Cited

U.S. PATENT DOCUMENTS 5,159,060 A  10/1992  Kinder et al. .............. 530/331

FOREIGN PATENT DOCUMENTS

FR   8014195   1/1981

OTHER PUBLICATIONS

Neurochemical Res. vol. 18, No. 7, 1993, Wilson et al,pp. 743–749.
Proc.Natl,Acad Sci,USA,vol. 85, pp.8326–8330, 11/88 Neurobiology.
Biochem, J. 1994, pp. 517–523, 304, Tomkinson.
Archives of Biochemistry, vo. 314,No. 2, 11/1 pp. 276–279 1994.
Biochemistry (1991), vol. 30, p. 168–174, Tomkinson et al, "Characterization . . . Peptidase II".
Journal of Biological Chemistry (1986), vol. 261, No. 5 p. 2409–2417 Balow et al, "Purification . . . Peptidase II".
Arch. Biochem. Biophy (1994), vol. 314, No. 2, p. 276–279, Tomkinson et al "Use . . . Peptidase II".
Neurochem Res (1993), vol. 18, No. 7, 743–749, Wilson et al , "Purification . . . Human Brain".
Proc. Natl. Acad. Sci USA, (1988), vol. 85, p. 8326–8330, Rose et al A Serine . . . Brain.
Biochemical Journal, (1994), vol. 304, p. 517–523, Tomkinson, "Characterization . . . Splicing".

*Primary Examiner*—Christopher S. F. Low
*Assistant Examiner*—David Lukton
(74) *Attorney, Agent, or Firm*—Bierman, Muserlian and Lucas

(57) ABSTRACT

A compound of formula

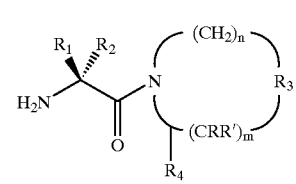

wherein the substituents are defined as in the specification and salts or hydrates thereof is disclosed as well as a method of treating disorders associated with the inactivation or excessive degradation of cholecystokinin.

17 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 4617
      (B) TYPE: NUCLEIC ACID
      (C) STRANDEDNESS: DOU BLE
      (D) TOPOLOGY: LINEAR (ii) MOLECULE TYPE: cDNA (vi) ORIGINAL SOURCE:
      (A) ORGANISM: RAT
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(xi) SEQUENCE DESCRIPTION:SEQ ID NO:1:

```
CGCCCCTCGT CCGCGCGCTG CCTGGCAGTT TACCTCTTCC                          40

ACGTCCGTCC TCCAGCTTGC GTCC                                          64

ATG GCC ACC GCT GCG ACC GAG GAG CCT TTC C CT TTC                   100
Met Ala Thr Ala Ala Thr Glu Glu Pro Phe P ro Phe
1               5                   10

CAT GGT CTT CTA CCA AAG AAA GAG ACT GGG G CC TCC                   136
His Gly Leu Leu Pro Lys Lys Glu Thr Gly A la Ser
15                  20

TCC TTC CTG TGC CGC TAC CCG GAG TAT GAC G GA CGC                   172
Ser Phe Leu Cys Arg Tyr Pro Glu Tyr Asp G ly Arg
25                  30                  35

GGG GTG CTC ATC GCC GTC CTG GAC ACA GGG G TT GAT                   208
Gly Val Leu Ile Ala Val Leu Asp Thr Gly V al Asp
40                  4 5

CCC GGG GCC CCG GGC ATG CAG GTC ACG ACT G AT GGG                   244
Pro Gly Ala Pro Gly Met Gln Val Thr Thr A sp Gly
50                  55                  60

AAA CCA AAA ATC ATT GAT ATC ATT GAT ACA A CA GGA                   280
Lys Pro Lys Ile Ile Asp Ile Ile Asp Thr T hr Gly
65                  70

AGT GGT GAT GTG AAT ACT GCT ACA GAA GTA G AA CCA                   316
Ser Gly Asp Val Asn Thr Ala Thr Glu Val G lu Pro
75                  80

AAA GAT GCG GAA ATC ACT GGT CTT TCT GGA A GA GTG                   352
Lys Asp Ala Glu Ile Thr Gly Leu Ser Gly A rg Val
85                  90                  95

CTT AAG ATT CCT GCA AAC TGG ACA AAT CCT T CA GGA                   388
Leu Lys Ile Pro Ala Asn Trp Thr Asn Pro S er Gly
100                 105

AAA TAT CAT ATT GGC ATT AAA AAT GGT TAT G AC TTC                   424
Lys Tyr His Ile Gly Ile Lys Asn Gly Tyr A sp Phe
110                 115                 120

TAT CCA AAG GCT CTC AAG GAA AGG ATA CAG A AA GAA                   460
Tyr Pro Lys Ala Leu Lys Glu Arg Ile Gln L ys Glu
125                 130
```

```
CGG AAG GAA AAA ATC TGG GAT CCA ATT CAC A GA GTT                    496
Arg Lys Glu Lys Ile Trp Asp Pro Ile His A rg Val
135                 140

GCG CTT GCA GAA GCT TGT AGA AAA CAA GAA G AA TTT                    532
Ala Leu Ala Glu Ala Cys Arg Lys Gln Glu G lu Phe
145                 150                 155

GAT ATT GCC AAT AAT GGC TCT TCC CAA GCC A AT AAA                    568
Asp Ile Ala Asn Asn Gly Ser Ser Gln Ala A sn Lys
160                 165

CTA ATC AAG GAA GAG TTG CAG AGT CAA GTG G AA TTA                    604
Leu Ile Lys Glu Glu Leu Gln Ser Gln Val G lu Leu
170                 175                 180

CTT AAT TCT TTT GAG AAA AAG TAT AGT GAT C CA GGC                    640
Leu Asn Ser Phe Glu Lys Lys Tyr Ser Asp P ro Gly
185                 190

CCT GTG TAT GAC TGC TTG GTG TGG CAT GAT G GT GAG                    676
Pro Val Tyr Asp Cys Leu Val Trp His Asp G ly Glu
195                 200

ACC TGG AGA GCC TGT GTT GAT TCG AAT GAA A AT GGG                    712
Thr Trp Arg Ala Cys Val Asp Ser Asn Glu A sn Gly
205                 210                 215

GAC TTG GGT AAA TCT ACT GTA TTG AGA AAC T AC AAA                    748
Asp Leu Gly Lys Ser Thr Val Leu Arg Asn T yr Lys
220                 225

GAG GCT CAA GAA TAT GGT TCT TTT GGC ACA G CT GAG                    784
Glu Ala Gln Glu Tyr Gly Ser Phe Gly Thr A la Glu
230                 235                 240

ATG CTG AAT TAC TCT GTT AAT ATT TAT GAT G AT GGA                    820
Met Leu Asn Tyr Ser Val Asn Ile Tyr Asp A sp Gly
245                 250

AAC CTG CTC TCC ATT GTG ACC AGT GGA GGA G CT CAT                    856
Asn Leu Leu Ser Ile Val Thr Ser Gly Gly A la His
255                 260

GGA ACC CAT GTA GCG AGT ATA GCT GCT GGG C AT TTT                    892
Gly Thr His Val Ala Ser Ile Ala Ala Gly H is Phe
265                 270                 275

CCA GAA GAG CCT GAA CGG AAT GGA GTT GCT C CT GGT                    928
Pro Glu Glu Pro Glu Arg Asn Gly Val Ala P ro Gly
280                 285

GCT CAA ATT CTA TCC ATT AAG ATT GGT GAT A CA AGG                    964
Ala Gln Ile Leu Ser Ile Lys Ile Gly Asp T hr Arg
290                 295                 300

CTA AGC ACC ATG GAA ACA GGC ACA GGC CTC A TC AGA                   1000
Leu Ser Thr Met Glu Thr Gly Thr Gly Leu I le Arg
305                 310

GCT ATG ATA GAA GTT ATA AAT CAT AAG TGT G AT CTT                   1036
Ala Met Ile Glu Val Ile Asn His Lys Cys A sp Leu
315                 320

GTC AAC TAC AGT TAT GGA GAA GCA ACT CAT T GG CCA                   1072
Val Asn Tyr Ser Tyr Gly Glu Ala Thr His T rp Pro
325                 330                 335

AAT TCT GGG AGA ATT TGT GAA GTA ATT AAT G AA GCA                   1108
Asn Ser Gly Arg Ile Cys Glu Val Ile Asn G lu Ala
340                 345

GTA TGG AAA CAT AAT ACA ATT TAT GTT TCA A GT GCT                   1144
Val Trp Lys His Asn Thr Ile Tyr Val Ser S er Ala
350                 355                 360

GGA AAT AAT GGT CCA TGC CTT TCT ACA GTG G GT TGT                   1180
Gly Asn Asn Gly Pro Cys Leu Ser Thr Val G ly Cys
365                 370
```

```
CCA GGA GGA ACT ACT TCC AGC GTG ATA GGT G TT GGA              1216
Pro Gly Gly Thr Thr Ser Ser Val Ile Gly V al Gly
375                 380

GCT TAT GTT TCT CCT GAT ATG ATG GTT GCA G AG TAT              1252
Ala Tyr Val Ser Pro Asp Met Met Val Ala G lu Tyr
385                 390                 395

TCA CTG AGA GAG AAA CTA CCT GCA AAT CAA T AT ACA              1288
Ser Leu Arg Glu Lys Leu Pro Ala Asn Gln T yr Thr
400                 405

TGG TCT TCT AGA GGC CCA AGT GCT GAT GGG G CC CTT              1324
Trp Ser Ser Arg Gly Pro Ser Ala Asp Gly A la Leu
410                 415                 420

GGT GTG AGC ATC AGT GCA CCA GGA GGT GCT A TT GCT              1360
Gly Val Ser Ile Ser Ala Pro Gly Gly Ala I le Ala
425                 430

TCT GTG CCT AAC TGG ACA TTG AGG GGG ACT C AG CTA              1396
Ser Val Pro Asn Trp Thr Leu Arg Gly Thr G ln Leu
435                 440

ATG AAT GGG ACA TCA ATG TCT TCC CCC AAT G CC TGT              1432
Met Asn Gly Thr Ser Met Ser Ser Pro Asn A la Cys
445                 450                 455

GGT GGC ATT GCC CTG GTA CTT TCA GGG CTG A AA GCA              1468
Gly Gly Ile Ala Leu Val Leu Ser Gly Leu L ys Ala
460                 465

AAT AAT GTT GAC TAT ACT GTT CAC TCA GTC A GA AGA              1504
Asn Asn Val Asp Tyr Thr Val His Ser Val A rg Arg
470                 475                 480

GCT CTA GAA AAC ACT GCA ATA AAA GCT GAC A AT ATA              1540
Ala Leu Glu Asn Thr Ala Ile Lys Ala Asp A sn Ile
485                 490

GAA GTA TTT GCC CAA GGA CAT GGA ATT ATT C AG GTT              1576
Glu Val Phe Ala Gln Gly His Gly Ile Ile G ln Val
495                 500

GAC AAA GCT TAT GAC TAC CTC ATT CAG AAT A CA TCA              1612
Asp Lys Ala Tyr Asp Tyr Leu Ile Gln Asn T hr Ser
505                 510                 515

TTT GCT AAC AGA TTA GGT TTT ACA GTT ACA G TT GGA              1648
Phe Ala Asn Arg Leu Gly Phe Thr Val Thr V al Gly
520                 525

AAT AAC CGT GGC ATC TAC CTC CGA GAT CCT G TT CAG              1684
Asn Asn Arg Gly Ile Tyr Leu Arg Asp Pro V al Gln
530                 535                 540

GTG GCT GCT CCT TCA GAT CAT GGT GTT GGC A TT GAG              1720
Val Ala Ala Pro Ser Asp His Gly Val Gly I le Glu
545                 550

CCT GTA TTT CCA GAG AAC ACA GAA AAC TCT G AA AAA              1756
Pro Val Phe Pro Glu Asn Thr Glu Asn Ser G lu Lys
555                 560

ATA TCC TTC CAG CTT CAT TTA GCT TTA ACT T CA AAT              1792
Ile Ser Phe Gln Leu His Leu Ala Leu Thr S er Asn
565                 570                 575

TCA TCT TGG GTT CAA TGT CCC AGC CAT TTG G AA CTC              1828
Ser Ser Trp Val Gln Cys Pro Ser His Leu G lu Leu
580                 585

ATG AAT CAA TGT CGG CAC ATA AAC ATA CGT G TG GAC              1864
Met Asn Gln Cys Arg His Ile Asn Ile Arg V al Asp
590                 595                 600

CCC AGG GGC TTA AGA GAA GGG TTA CAT TAT A CA GAG              1900
Pro Arg Gly Leu Arg Glu Gly Leu His Tyr T hr Glu
```

-continued

| | |
|---|---|
| GTA TGT GGG TAT GAT ATA GCA TCC CCC AAT G CA GGT<br>Val Cys Gly Tyr Asp Ile Ala Ser Pro Asn A la Gly<br>615                    620 | 1936 |
| CCT TTA TTC AGA GTT CCA ATC ACT GCA GTT A TA GCA<br>Pro Leu Phe Arg Val Pro Ile Thr Ala Val I le Ala<br>625                    630                    635 | 1972 |
| GCA AAA GTA AAT GAA TCA TCA CAT TAT GAT C TA GCC<br>Ala Lys Val Asn Glu Ser Ser His Tyr Asp L eu Ala<br>640                    645 | 2008 |
| TTT ACA GAT GTA CAT TTT AAA CCT GGT CAG A TT CGA<br>Phe Thr Asp Val His Phe Lys Pro Gly Gln I le Arg<br>650                    655                    660 | 2044 |
| AGA CAT TTT GTT GAG GTT CCT GAG GGG GCA A CT TGG<br>Arg His Phe Val Glu Val Pro Glu Gly Ala T hr Trp<br>665                    670 | 2080 |
| GCT GAA GTT ACC GTG TGT TCG TGT TCT TCT G AG GTA<br>Ala Glu Val Thr Val Cys Ser Cys Ser Ser G lu Val<br>675                    680 | 2116 |
| TCA GCA AAA TTT GTT CTT CAT GCA GTA CAG C TT GTG<br>Ser Ala Lys Phe Val Leu His Ala Val Gln L eu Val<br>685                    690                    695 | 2152 |
| AAG CAG AGA GCA TAT CGA AGT CAT GAA TTT T AT AAG<br>Lys Gln Arg Ala Tyr Arg Ser His Glu Phe T yr Lys<br>700                    705 | 2188 |
| TTT TGT TCC CTT CCA GAA AAA GGA ACA CTC A TT GAA<br>Phe Cys Ser Leu Pro Glu Lys Gly Thr Leu I le Glu<br>710                    715                    720 | 2224 |
| GCC TTT CCT GTT CTG GGT GGG AAA GCA ATT G AA TTT<br>Ala Phe Pro Val Leu Gly Gly Lys Ala Ile G lu Phe<br>730 | 2260 |
| TGT ATT GCT CGT TGG TGG GCA AGT CTC AGT G AT GTC<br>Cys Ile Ala Arg Trp Trp Ala Ser Leu Ser A sp Val<br>735                    740 | 2296 |
| AAT ATT GAT TAT ACC ATA TCA TTC CAT GGC A TA GTG<br>Asn Ile Asp Tyr Thr Ile Ser Phe His Gly I le Val<br>745                    750                    755 | 2332 |
| TGT ACT GCA CCA CAG TTA AAC ATT CAT GCA T CT GAA<br>Cys Thr Ala Pro Gln Leu Asn Ile His Ala S er Glu<br>760                    765 | 2368 |
| GGA ATC AAT CGT TTT GAT GTC CAG TCC TCT T TA AAA<br>Gly Ile Asn Arg Phe Asp Val Gln Ser Ser L eu Lys<br>770                    775                    780 | 2404 |
| TAT GAA GAT CTG GCT CCT TGC ATA ACT TTG A AG AGC<br>Tyr Glu Asp Leu Ala Pro Cys Ile Thr Leu L ys Ser<br>785                    790 | 2440 |
| TGG GTG CAA ACA CTA CGC CCA GTA AAT GCA A AA ACC<br>Trp Val Gln Thr Leu Arg Pro Val Asn Ala L ys Thr<br>795                    800 | 2476 |
| AGA CCT TTA GGA TCA AGA GAT GTT TTG CCA A AT AAT<br>Arg Pro Leu Gly Ser Arg Asp Val Leu Pro A sn Asn<br>805                    810                    815 | 2512 |
| CGC CAG CTT TAT GAG ATG GTC CTG ACA TAC A GC TTT<br>Arg Gln Leu Tyr Glu Met Val Leu Thr Tyr S er Phe<br>820                    825 | 2548 |
| CAT CAG CCC AAG AGC GGA GAA GTA ACA CCT A GT TGT<br>His Gln Pro Lys Ser Gly Glu Val Thr Pro S er Cys<br>830                    835                    840 | 2584 |
| CCA CTC CTT TGT GAA TTA TTA TAT GAG TCA G AA TTT | 2620 |

```
Pro Leu Leu Cys Glu Leu Leu Tyr Glu Ser Glu Phe
845                 850

GAC AGT CAG TTG TGG ATT ATT TTT GAC CAG AAC AAA                2656
Asp Ser Gln Leu Trp Ile Ile Phe Asp Gln Asn Lys
855                 860

AGA CAG ATG GGC TCA GGC GAT GCC TAT CCA CAT CAG                2692
Arg Gln Met Gly Ser Gly Asp Ala Tyr Pro His Gln
865                 870                 875

TAT TCT TTG AAA TTG GAG AAA GGA GAT TAT ACG ATT                2728
Tyr Ser Leu Lys Leu Glu Lys Gly Asp Tyr Thr Ile
880                 885

CGA TTA CAG ATT CGT CAT GAG CAA ATC AGT GAT TTG                2764
Arg Leu Gln Ile Arg His Glu Gln Ile Ser Asp Leu
890                 895                 900

GAT CGT CTC AAA GAT CTT CCG TTT ATT GTT TCG CAT                2800
Asp Arg Leu Lys Asp Leu Pro Phe Ile Val Ser His
905                 910

AGG TTG TCT AAT ACC TTG AGC TTA GAT ATT CAT GAA                2836
Arg Leu Ser Asn Thr Leu Ser Leu Asp Ile His Glu
915                 920

AAT CAT AGC CTT GCA CTT CTA GGA AAG AAG AAA TCA                2872
Asn His Ser Leu Ala Leu Leu Gly Lys Lys Lys Ser
925                 930                 935

AGC AGT TTG ACA TTA CCA CCC AAA TAT AAT CAG CCA                2908
Ser Ser Leu Thr Leu Pro Pro Lys Tyr Asn Gln Pro
940                 945

TTC TTT GTT ACT TCC TTA CCT GAT GAT AAA ATA CCT                2944
Phe Phe Val Thr Ser Leu Pro Asp Asp Lys Ile Pro
950                 955                 960

AAG GGG GCA GGA CCC GGA TGC TAC CTT GCA GGC TCC                2980
Lys Gly Ala Gly Pro Gly Cys Tyr Leu Ala Gly Ser
965                 970

TTG ACA TTG TCA AAG ACT GAG CTT GGA AAG AAA GCT                3016
Leu Thr Leu Ser Lys Thr Glu Leu Gly Lys Lys Ala
975                 980

GAT GTG ATC CCT GTT CAT TAC TAT CTA ATA CCT CCA                3052
Asp Val Ile Pro Val His Tyr Tyr Leu Ile Pro Pro
985                 990                 995

CCA ACA AAG ACT AAG AAT GGC AGC AAA GAT AAA GAA                3088
Pro Thr Lys Thr Lys Asn Gly Ser Lys Asp Lys Glu
1000                1005

AAG GAT TCA GAA AAA GAG AAA GAT TTG AAA GAA GAG                3124
Lys Asp Ser Glu Lys Glu Lys Asp Leu Lys Glu Glu
1010                1015                1020

TTT ACT GAA GCT TTA CGA GAT CTT AAA ATT CAG TGG                3160
Phe Thr Glu Ala Leu Arg Asp Leu Lys Ile Gln Trp
1025                1030

ATG ACC AAG CTG GAT TCT ACT GAC ATT TAC AAT GAA                3196
Met Thr Lys Leu Asp Ser Thr Asp Ile Tyr Asn Glu
1035                1040

TTG AAA GAA ACA TAT CCT GCT TAC CTT CCT TTG TAT                3232
Leu Lys Glu Thr Tyr Pro Ala Tyr Leu Pro Leu Tyr
1045                1050                1055

GTT GCA CGT CTT CAT CAA TTA GAT GCT GAA AAG GAG                3268
Val Ala Arg Leu His Gln Leu Asp Ala Glu Lys Glu
1060                1065

CGG ATG AAA AGA CTT AAT GAA ATT GTT GAT GCT GCC                3304
Arg Met Arg Arg Leu Asn Glu Ile Val Asp Ala Ala
1070                1075                1080
```

| | |
|---|---|
| AAT GCT GTT ATT TCT CAC ATC GAT CAG ACC G CT CTC<br>Asn Ala Val Ile Ser His Ile Asp Gln Thr A la Leu<br>1085                       109 0 | 3340 |
| GCT GTT TAC ATT GCC ATG AAG ACT GAC CCC A GG CCT<br>Ala Val Tyr Ile Ala Met Lys Thr Asp Pro A rg Pro<br>1095                       110 0 | 3376 |
| GAT GCA GCT ACT ATA AAA AAT GAT ATG GAC A AG CAG<br>Asp Ala Ala Thr Ile Lys Asn Asp Met Asp L ys Gln<br>1105           1110                  1115 | 3412 |
| AAA TCT ACC CTG GTA GAT GCC CTC TGC AGG A AA GGA<br>Lys Ser Thr Leu Val Asp Ala Leu Cys Arg L ys Gly<br>1120                       112 5 | 3448 |
| TGT GCT CTG GCA GAC CAC CTT CTT CAT GCA C AG CCC<br>Cys Ala Leu Ala Asp His Leu Leu His Ala G ln Pro<br>1130                       113 5               1140 | 3484 |
| CAC CAT GGG GCA GCA GCT GGA GAT GCA GAA G CA AAA<br>His Asp Gly Ala Ala Ala Gly Asp Ala Glu A la Lys<br>1145                       115 0 | 3520 |
| GAA GAG GAA GGA GAA AGT ACC TTG GAA TCT C TA TCA<br>Glu Glu Glu Gly Glu Ser Thr Leu Glu Ser L eu Ser<br>1155                       116 0 | 3556 |
| GAA ACC TAT TGG CAA ACT ACA AAG TGG ACA G AT CTT<br>Glu Thr Tyr Trp Gln Thr Thr Lys Trp Thr A sp Leu<br>1165                       117 0               1175 | 3592 |
| TTT GAC ACT AAG GTT TTG ACA TTT GCA TAC A AG CAT<br>Phe Asp Thr Lys Val Leu Thr Phe Ala Tyr L ys His<br>1180                       118 5 | 3628 |
| GCA TTA GTA AAT AAG ATG TAC GGG AGA GGC C TT AAG<br>Ala Leu Val Asn Lys Met Tyr Gly Arg Gly L eu Lys<br>1190                       119 5               1200 | 3664 |
| TTT GCA ACC AAA CTC GTA GAA GAA AAA CCA A CA AAA<br>Phe Ala Thr Lys Leu Val Glu Glu Lys Pro T hr Lys<br>1205                       121 0 | 3700 |
| GAA AAC TGG AAA AAT TGT ATT CAA CTG ATG A AA TTA<br>Glu Asn Trp Lys Asn Cys Ile Gln Leu Met L ys Leu<br>1215                       122 0 | 3736 |
| CTC GGA TGG ACC CAT TGT GCG TCT TTT ACT G AA AAC<br>Leu Gly Trp Thr His Cys Ala Ser Phe Thr G lu Asn<br>1225           1230                  1235 | 3772 |
| TGG CTC CCC ATC ATG TAT CCT CCT GAT TAT T GT GTA<br>Trp Leu Pro Ile Met Tyr Pro Pro Asp Tyr C ys Val<br>1240                       124 5 | 3808 |
| TTC TAA<br>Phe | 3814 |
| AATGGGAACC AAAACGTTAA ATTTCGAAAG CAGAAAATTT | 3854 |
| TATAGTGAAC AAATATATGA ACAAATGTGT GGCATTTCTA | 3894 |
| GTCTAACTAA TGCATGTCTT CATCCACTAT CGAATACTGA | 3934 |
| TCATTAAAAC TCTATGTATT TATCAGAGAA CTCAATGGTG | 3974 |
| TGTGGCTTCA TACATGTAAT GTAGACAGAC CTCTGACATC | 4014 |
| ATGCTGCTTT CCTGCTGCCT CCCACACTTG GCTAGGGAGG | 4054 |
| GCAGAGCCTG CCTGCCAGCC CCAACCTGGG TGGATGCAGC | 4094 |
| TGCTCACTGC AGGAGAGGTT TTCATCTCTT AATTTTTAAC | 4134 |
| TGTAAAACGT CATCCAGTTT TTATTTTATA AATCAAAAAG | 4174 |
| GTTAAAACAT GCTAAATTTT TCCAATTATA TAGAGGCCTT | 4214 |

-continued

| | |
|---|---|
| AAAAATGCTA CATTGGGTGT AGCTAAATTA TTTATTTGAC | 4254 |
| TAAAAATTAC GAGAACATAA TTTCCAGACT TCTAAAAATA | 4294 |
| AATTCAATTA ATGGGTATGG TGGGGAGGTA TAAATACATG | 4334 |
| GCAACTGGGA AAAGAAACGT GTTAATGTAA TCTTCACTCC | 4374 |
| GGAGTCACAA CAAGCAAGTT GTTTTTACAG CATCCTCAAG | 4414 |
| TACACAGCAT CAGAATAAGT TAAAATTTCA TGTGTTGGTG | 4454 |
| CCAGACAGTT GAATCTATCT GGTTTTGTAA AGATATACAC | 4494 |
| AGTATGTTTA TAACATTGAA ATCATGTAAA ATACATGAAT | 4534 |
| AAATGTGCAA AACAACAGGC ACAGCACACC ATATGCACTC | 4574 |
| TGATACCTGT TTTTTATAAA TAAAAGTAAA TATTGAAGCT | 4614 |
| AAA | 4617 |

(2) INFORMATION FOR SEQ ID NO:2:

(i) SEQUENCE CHARACTERISTICS:
  (A) LENGTH: 5109
  (B) TYPE: NUCLEIC ACID
  (C) STRANDEDNESS: DOU BLE
  (D) TOPOLOGY: LINEAR (ii) MOLECULE TYPE: cDNA (vi) ORIGINAL SOURCE:
  (A) ORGANISM: RAT
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(xi) SEQUENCE DESCRIPTION: SEQ ID NO:2:

| | |
|---|---|
| ATAATTTGTT TGGTTTCACT GCTGAGTACC ATGCTATGAT | 40 |
| TTCTACACTA TCTGCTTATT AAACTGTTTC TTACTGTTTG | 80 |
| GAACTGTTAT CTAACAGTTA TTTCAAAAAG CATTAGGCAC | 120 |
| AGTTCCTGTG CCTGTGTGCA GATGTTTCCA GGATGTATAC | 160 |
| CAGAAATGGA ATTGCTGAGT CAGGGAGATT CAGGTTTACT | 200 |
| AGGTCATGTG TAACAGCTTT TTCATTGAGC TGGCCTTGAA | 240 |
| CTCTTCTGAT ATTCCTGCCT CCACCTCCCA GCTGCTGTGA | 280 |
| TTATGGATAT ATTCCACCAT GCCTGGCCAA CTGTTAACTT | 320 |
| CTTTTTTTA ATTTTATTTT TTTTTTAAAG ATTTTATTTT | 360 |
| ATTGTATGAG TGCACTGTAG CTGCCTTCAG ACACACCAGA | 400 |
| AGAGGGCATT GGATTCCATT ACAGATGGTT GTGAGCCACC | 440 |
| ATGTGGTTGC TGGGATTTGA ACTCAGGACC TCAGGAAGAG | 480 |
| CACTCGGTGC TCTTAACCAC TGAGCCATCT CTCCAGCCCC | 520 |
| CAACTGTTAA CTTCTTATAC TTTGAATTTT CAGACCTGTT | 560 |
| TTTAATTTCT TATGTAGGAA ATATCAGTGT ATTGCAGG | 598 |
| TTT GAT TTG CAT TTT TAT AGT GAA ATC AGT T AT TTT<br>Phe Asp Leu His Phe Tyr Ser Glu Ile Ser T yr Phe<br>1     5       10 | 634 |

-continued

| | |
|---|---|
| TCT AAC AGA TTT AGG CTT TTG GGT CCT CTC A TA GTG<br>Ser Asn Arg Phe Arg Leu Leu Gly Pro Leu I le Val<br>15                              20 | 670 |
| CTA TTA AAG TTC TTT TAC TTT TTC ATT TTC T GT TTT<br>Leu Leu Lys Phe Phe Tyr Phe Phe Ile Phe C ys Phe<br>25                            30                        35 | 706 |
| TTT TTT TTT TTT AAT ACT ACT AAG TTG TCA A TT GCT<br>Phe Phe Phe Phe Asn Thr Thr Lys Leu Ser I le Ala<br>40                            4 5 | 742 |
| TTT TTT TTT TTT CCG GAG CTG GGG ATC GAA C CC AGG<br>Phe Phe Phe Phe Pro Glu Leu Gly Ile Glu P ro Arg<br>50                            55                        60 | 778 |
| GCC TTG CGC TTG CTA GGC AAG CGC TCT ACC G CT GAG<br>Ala Leu Arg Leu Leu Gly Lys Arg Ser Thr A la Glu<br>65                            70 | 814 |
| CTA AAT CTC CAA CCC CTG TCA ATT GCT TTT T CA CTG<br>Leu Asn Leu Gln Pro Leu Ser Ile Ala Phe S er Leu<br>75                            80 | 850 |
| ATT CCT GCA AAC TGG ACA AAT CCT TCA GGA A AA TAT<br>Ile Pro Ala Asn Trp Thr Asn Pro Ser Gly L ys Tyr<br>85                            90                        95 | 886 |
| CAT ATT GGC ATT AAA AAT GGT TAT GAC TTC T AT CCA<br>His Ile Gly Ile Lys Asn Gly Tyr Asp Phe T yr Pro<br>100                          105 | 922 |
| AAG GCT CTC AAG GAA AGG ATA CAG AAA GAA C GG AAG<br>Lys Ala Leu Lys Glu Arg Ile Gln Lys Glu A rg Lys<br>110                          115                        120 | 958 |
| GAA AAA ATC TGG GAT CCA ATT CAC AGA GTT G CG CTT<br>Glu Lys Ile Trp Asp Pro Ile His Arg Val A la Leu<br>125                          130 | 994 |
| GCA GAA GCT TGT AGA AAA CAA GAA GAA TTT G AT ATT<br>Ala Glu Ala Cys Arg Lys Gln Glu Glu Phe A sp Ile<br>135                          140 | 1030 |
| GCC AAT AAT GGC TCT TCC CAA GCC AAT AAA C TA ATC<br>Ala Asn Asn Gly Ser Ser Gln Ala Asn Lys L eu Ile<br>145                          150                     155 | 1066 |
| AAG GAA GAG TTG CAG AGT CAA GTG GAA TTA C TT AAT<br>Lys Glu Glu Leu Gln Ser Gln Val Glu Leu L eu Asn<br>160                          165 | 1102 |
| TCT TTT GAG AAA AAG TAT AGT GAT CCA GGC C CT GTG<br>Ser Phe Glu Lys Lys Tyr Ser Asp Pro Gly P ro Val<br>170                          175                     180 | 1138 |
| TAT GAC TGC TTG GTG TGG CAT GAT GGT GAG A CC TGG<br>Tyr Asp Cys Leu Val Trp His Asp Gly Glu T hr Trp<br>185                          190 | 1174 |
| AGA GCC TGT GTT GAT TCG AAT GAA AAT GGG G AC TTG<br>Arg Ala Cys Val Asp Ser Asn Glu Asn Gly A sp Leu<br>195                          200 | 1210 |
| GGT AAA TCT ACT GTA TTG AGA AAC TAC AAA G AG GCT<br>Gly Lys Ser Thr Val Leu Arg Asn Tyr Lys G lu Ala<br>205                          210                     215 | 1246 |
| CAA GAA TAT GGT TCT TTT GGC ACA GCT GAG A TG CTG<br>Gln Glu Tyr Gly Ser Phe Gly Thr Ala Glu M et Leu<br>220                          225 | 1282 |
| AAT TAC TCT GTT AAT ATT TAT GAT GAT GGA A AC CTG<br>Asn Tyr Ser Val Asn Ile Tyr Asp Asp Gly A sn Leu<br>230                          235                     240 | 1318 |
| CTC TCC ATT GTG ACC AGT GGA GGA GCT CAT G GA ACC<br>Leu Ser Ile Val Thr Ser Gly Gly Ala His G ly Thr<br>245                          250 | 1354 |

-continued

| | | |
|---|---|---|
| CAT GTA GCG AGT ATA GCT GCT GGG CAT TTT C CA GAA<br>His Val Ala Ser Ile Ala Ala Gly His Phe P ro Glu<br>255                               260 | | 1390 |
| GAG CCT GAA CGG AAT GGA GTT GCT CCT GGT G CT CAA<br>Glu Pro Glu Arg Asn Gly Val Ala Pro Gly A la Gln<br>265                         270                       275 | | 1426 |
| ATT CTA TCC ATT AAG ATT GGT GAT ACA AGG C TA AGC<br>Ile Leu Ser Ile Lys Ile Gly Asp Thr Arg L eu Ser<br>280                         285 | | 1462 |
| ACC ATG GAA ACA GGC ACA GGC CTC ATC AGA G CT ATG<br>Thr Met Glu Thr Gly Thr Gly Leu Ile Arg A la Met<br>290                       295                       300 | | 1498 |
| ATA GAA GTT ATA AAT CAT AAG TGT GAT CTT G TC AAC<br>Ile Glu Val Ile Asn His Lys Cys Asp Leu V al Asn<br>305                         310 | | 1534 |
| TAC AGT TAT GGA GAA GCA ACT CAT TGG CCA A AT TCT<br>Tyr Ser Tyr Gly Glu Ala Thr His Trp Pro A sn Ser<br>315                       320 | | 1570 |
| GGG AGA ATT TGT GAA GTA ATT AAT GAA GCA G TA TGG<br>Gly Arg Ile Ser Glu Val Ile Asn Glu Ala V al Trp<br>325                       330                   335 | | 1606 |
| AAA CAT AAT ACA ATT TAT GTT TCA AGT GCT G GA AAT<br>Lys His Asn Thr Ile Tyr Val Ser Ser Ala G ly Asn<br>340                       345 | | 1642 |
| AAT GGT CCA TGC CTT TCT ACA GTG GGT TGT C CA GGA<br>Asn Gly Pro Cys Leu Ser Thr Val Gly Cys P ro Gly<br>350                       355                   360 | | 1678 |
| GGA ACT ACT TCC AGC GTG ATA GGT GTT GGA G CT TAT<br>Gly Thr Thr Ser Ser Val Ile Gly Val Gly A la Tyr<br>365                       370 | | 1714 |
| GTT TCT CCT GAT ATG ATG GTT GCA GAG TAT T CA CTG<br>Val Ser Pro Asp Met Met Val Ala Glu Tyr S er Leu<br>375                       380 | | 1750 |
| AGA GAG AAA CTA CCT GCA AAT CAA TAT ACA T GG TCT<br>Arg Glu Lys Leu Pro Ala Asn Gln Tyr Thr T rp Ser<br>385                       390                   395 | | 1786 |
| TCT AGA GGC CCA AGT GCT GAT GGG GCC CTT G GT GTG<br>Ser Arg Gly Pro Ser Ala Asp Gly Ala Leu G ly Val<br>400                       405 | | 1822 |
| AGC ATC AGT GCA CCA GGA GGT GCT ATT GCT T CT GTG<br>Ser Ile Ser Ala Pro Gly Gly Ala Ile Ala S er Val<br>410                       415                   420 | | 1858 |
| CCT AAC TGG ACA TTG AGG GGG ACT CAG CTA A TG AAT<br>Pro Asn Trp Thr Leu Arg Gly Thr Gln Leu M et Asn<br>425                       430 | | 1894 |
| GGG ACA TCA ATG TCT TCC CCC AAT GCC TGT G GT GGC<br>Gly Thr Ser Met Ser Ser Pro Asn Ala Cys G ly Gly<br>435                       440 | | 1930 |
| ATT GCC CTG GTA CTT TCA GGG CTG AAA GCA A AT AAT<br>Ile Ala Leu Val Leu Ser Gly Leu Lys Ala A sn Asn<br>445                       450                   455 | | 1966 |
| GTT GAC TAT ACT GTT CAC TCA GTC AGA AGA G CT CTA<br>Val Asp Tyr Thr Val His Ser Val Arg Arg A la Leu<br>460                       465 | | 2002 |
| GAA AAC ACT GCA ATA AAA GCT GAC AAT ATA G AA GTA<br>Glu Asn Thr Ala Ile Lys Ala Asp Asn Ile G lu Val<br>470                       475                   480 | | 2038 |
| TTT GCC CAA GGA CAT GGA ATT ATT CAG GTT G AC AAA<br>Phe Ala Gln Gly His Gly Ile Ile Gln Val A sp Lys | | 2074 |

```
                                                              -continued
485               490
GCT TAT GAC TAC CTC ATT CAG AAT ACA TCA T TT GCT                                        2110
Ala Tyr Asp Tyr Leu Ile Gln Asn Thr Ser P he Ala
495                   500

AAC AGA TTA GGT TTT ACA GTT ACA GTT GGA A AT AAC                                        2146
Asn Arg Leu Gly Phe Thr Val Thr Val Gly A sn Asn
505                   510                   515

CGT GGC ATC TAC CTC CGA GAT CCT GTT CAG G TG GCT                                        2182
Arg Gly Ile Tyr Leu Arg Asp Pro Val Gln V al Ala
520                   525

GCT CCT TCA GAT CAT GGT GTT GGC ATT GAG C CT GTA                                        2218
Ala Pro Ser Asp His Gly Val Gly Ile Glu P ro Val
530                   535                   540

TTT CCA GAG AAC ACA GAA AAC TCT GAA AAA A TA TCC                                        2254
Phe Pro Glu Asn Thr Glu Asn Ser Glu Lys I le Ser
545                   550

TTC CAG CTT CAT TTA GCT TTA ACT TCA AAT T CA TCT                                        2290
Phe Gln Leu His Leu Ala Leu Thr Ser Asn S er Ser
555                   560

TGG GTT CAA TGT CCC AGC CAT TTG GAA CTC A TG AAT                                        2326
Trp Val Gln Cys Pro Ser His Leu Glu Leu M et Asn
565                   570                   575

CAA TGT CGG CAC ATA AAC ATA CGT GTG GAC C CC AGG                                        2362
Gln Cys Arg His Ile Asn Ile Arg Val Asp P ro Arg
580                   585

GGC TTA AGA GAA GGG TTA CAT TAT ACA GAG G TA TGT                                        2398
Gly Leu Arg Glu Gly Leu His Tyr Thr Glu V al Cys
590                   595                   600

GGG TAT GAT ATA GCA TCC CCC AAT GCA GGT C CT TTA                                        2434
Gly Tyr Asp Ile Ala Ser Pro Asn Ala Gly P ro Leu
605                   610

TTC AGA GTT CCA ATC ACT GCA GTT ATA GCA G CA AAA                                        2470
Phe Arg Val Pro Ile Thr Ala Val Ile Ala A la Lys
615                   620

GTA AAT GAA TCA TCA CAT TAT GAT CTA GCC T TT ACA                                        2506
Val Asn Glu Ser Ser His Tyr Asp Leu Ala P he Thr
625                   630                   635

GAT GTA CAT TTT AAA CCT GGT CAG ATT CGA A GA CAT                                        2542
Asp Val His Phe Lys Pro Gly Gln Ile Arg A rg His
640                   645

TTT GTT GAG GTT CCT GAG GGG GCA ACT TGG G CT GAA                                        2578
Phe Val Glu Val Pro Glu Gly Ala Thr Trp A la Glu
650                   655                   660

GTT ACC GTG TGT TCG TGT TCT TCT GAG GTA T CA GCA                                        2614
Val Thr Val Cys Ser Cys Ser Ser Glu Val S er Ala
665                   670

AAA TTT GTT CTT CAT GCA GTA CAG CTT GTG A AG CAG                                        2650
Lys Phe Val Leu His Ala Val Gln Leu Val L ys Gln
675                   680

AGA GCA TAT CGA AGT CAT GAA TTT TAT AAG T TT TGT                                        2686
Arg Ala Tyr Arg Ser His Glu Phe Tyr Lys P he Cys
685                   690                   695

TCC CTT CCA GAA AAA GGA ACA CTC ATT GAA G CC TTT                                        2722
Ser Leu Pro Glu Lys Gly Thr Leu Ile Glu A la Phe
700                   705

CCT GTT CTG GGT GGG AAA GCA ATT GAA TTT T GT ATT                                        2758
Pro Val Leu Gly Gly Lys Ala Ile Glu Phe C ys Ile
710                   715                   720

GCT CGT TGG TGG GCA AGT CTC AGT GAT GTC A AT ATT                                        2794
```

-continued

```
Ala Arg Trp Trp Ala Ser Leu Ser Asp Val A sn Ile
725                 730
GAT TAT ACC ATA TCA TTC CAT GGC ATA GTG T GT ACT                    2830
Asp Tyr Thr Ile Ser Phe His Gly Ile Val C ys Thr
735                 740
GCA CCA CAG TTA AAC ATT CAT GCA TCT GAA G GA ATC                    2866
Ala Pro Gln Leu Asn Ile His Ala Ser Glu G ly Ile
745                 750                 755
AAT CGT TTT GAT GTC CAG TCC TCT TTA AAA T AT GAA                    2902
Asn Arg Phe Asp Val Gln Ser Ser Leu Lys T yr Glu
760                 765
GAT CTG GCT CCT TGC ATA ACT TTG AAG AGC T GG GTG                    2938
Asp Leu Ala Pro Cys Ile Thr Leu Lys Ser T rp Val
770                 775                 780
CAA ACA CTA CGC CCA GTA AAT GCA AAA ACC A GA CCT                    2974
Gln Thr Leu Arg Pro Val Asn Ala Lys Thr A rg Pro
785                 790
TTA GGA TCA AGA GAT GTT TTG CCA AAT AAT C GC CAG                    3010
Leu Gly Ser Arg Asp Val Leu Pro Asn Asn A rg Gln
795                 800
CTT TAT GAG ATG GTC CTG ACA TAC AGC TTT C AT CAG                    3046
Leu Tyr Glu Met Val Leu Thr Tyr Ser Phe H is Gln
805                 810                 815
CCC AAG AGC GGA GAA GTA ACA CCT AGT TGT C CA CTC                    3082
Pro Lys Ser Gly Glu Val Thr Pro Ser Cys P ro Leu
820                 825
CTT TGT GAA TTA TTA TAT GAG TCA GAA TTT G AC AGT                    3118
Leu Cys Glu Leu Leu Tyr Glu Ser Glu Phe A sp Ser
830                 835                 840
CAG TTG TGG ATT ATT TTT GAC CAG AAC AAA A GA CAG                    3154
Gln Leu Trp Ile Ile Phe Asp Gln Asn Lys A rg Gln
845                 850
ATG GGC TCA GGC GAT GCC TAT CCA CAT CAG T AT TCT                    3190
Met Gly Ser Gly Asp Ala Tyr Pro His Gln T yr Ser
855                 860
TTG AAA TTG GAG AAA GGA GAT TAT ACG ATT C GA TTA                    3226
Leu Lys Leu Glu Lys Gly Asp Tyr Thr Ile A rg Leu
865                 870                 875
CAG ATT CGT CAT GAG CAA ATC AGT GAT TTG G AT CGT                    3262
Gln Ile Arg His Glu Gln Ile Ser Asp Leu A sp Arg
880                 885
CTC AAA GAT CTT CCG TTT ATT GTT TCG CAT A GG TTG                    3298
Leu Lys Asp Leu Pro Phe Ile Val Ser His A rg Leu
890                 895                 900
TCT AAT ACC TTG AGC TTA GAT ATT CAT GAA A AT CAT                    3334
Ser Asn Thr Leu Ser Leu Asp Ile His Glu A sn His
905                 910
AGC CTT GCA CTT CTA GGA AAG AAG AAA TCA A GC AGT                    3370
Ser Leu Ala Leu Leu Gly Lys Lys Lys Ser S er Ser
915                 920
TTG ACA TTA CCA CCC AAA TAT AAT CAG CCA T TC TTT                    3406
Leu Thr Leu Pro Pro Lys Tyr Asn Gln Pro P he Phe
925                 930                 935
GTT ACT TCC TTA CCT GAT GAT AAA ATA CCT A AG GGG                    3442
Val Thr Ser Leu Pro Asp Asp Lys Ile Pro L ys Gly
940                 945
GCA GGA CCC GGA TGC TAC CTT GCA GGC TCC T TG ACA                    3478
Ala Gly Pro Gly Cys Tyr Leu Ala Gly Ser L eu Thr
950                 955                 960
```

| | |
|---|---|
| TTG TCA AAG ACT GAG CTT GGA AAG AAA GCT G AT GTG<br>Leu Ser Lys Thr Glu Leu Gly Lys Lys Ala A sp Val<br>965                     970 | 3514 |
| ATC CCT GTT CAT TAC TAT CTA ATA CCT CCA C CA ACA<br>Ile Pro Val His Tyr Tyr Leu Ile Pro Pro P ro Thr<br>975                     980 | 3550 |
| AAG ACT AAG AAT GGC AGC AAA GAT AAA GAA A AG GAT<br>Lys Thr Lys Asn Gly Ser Lys Asp Lys Glu L ys Asp<br>985                     990                     995 | 3586 |
| TCA GAA AAA GAG AAA GAT TTG AAA GAA GAG T TT ACT<br>Ser Glu Lys Glu Lys Asp Leu Lys Glu Glu P he Thr<br>1000                    100 5 | 3622 |
| GAA GCT TTA CGA GAT CTT AAA ATT CAG TGG A TG ACC<br>Glu Ala Leu Arg Asp Leu Lys Ile Gln Trp M et Thr<br>1010                    101 5                  1020 | 3658 |
| AAG CTG GAT TCT ACT GAC ATT TAC AAT GAA T TG AAA<br>Lys Leu Asp Ser Thr Asp Ile Tyr Asn Glu L eu Lys<br>1025                    103 0 | 3694 |
| GAA ACA TAT CCT GCT TAC CTT CCT TTG TAT G TT GCA<br>Glu Thr Tyr Pro Ala Tyr Leu Pro Leu Tyr V al Ala<br>1035                    104 0 | 3730 |
| CGT CTT CAT CAA TTA GAT GCT GAA AAG GAG C GG ATG<br>Arg Leu His Gln Leu Asp Ala Glu Lys Glu A rg Met<br>1045                    1050                  1055 | 3766 |
| AAA AGA CTT AAT GAA ATT GTT GAT GCT GCC A AT GCT<br>Arg Arg Leu Asn Glu Ile Val Asp Ala Ala A sn Ala<br>1060                    106 5 | 3802 |
| GTT ATT TCT CAC ATC GAT CAG ACC GCT CTC G CT GTT<br>Val Ile Ser His Ile Asp Gln Thr Ala Leu A la Val<br>1070                    107 5                  1080 | 3838 |
| TAC ATT GCC ATG AAG ACT GAC CCC AGG CCT G AT GCA<br>Tyr Ile Ala Met Lys Thr Asp Pro Arg Pro A sp Ala<br>1085                    109 0 | 3874 |
| GCT ACT ATA AAA AAT GAT ATG GAC AAG CAG A AA TCT<br>Ala Thr Ile Lys Asn Asp Met Asp Lys Gln L ys Ser<br>1095                    110 0 | 3910 |
| ACC CTG GTA GAT GCC CTC TGC AGG AAA GGA T GT GCT<br>Thr Leu Val Asp Ala Leu Cys Arg Lys Gly C ys Ala<br>1105                    1110                  1115 | 3946 |
| CTG GCA GAC CAC CTT CTT CAT GCA CAG CCC C AC CAT<br>Leu Ala Asp His Leu Leu His Ala Gln Pro H is Asp<br>1120                    112 5 | 3982 |
| GGG GCA GCA GCT GGA GAT GCA GAA GCA AAA G AA GAG<br>Gly Ala Ala Ala Gly Asp Ala Glu Ala Lys G lu Glu<br>1130                    113 5                  1140 | 4018 |
| GAA GGA GAA AGT ACC TTG GAA TCT CTA TCA G AA ACC<br>Glu Gly Glu Ser Thr Leu Glu Ser Leu Ser G lu Thr<br>1145                    115 0 | 4054 |
| TAT TGG CAA ACT ACA AAG TGG ACA GAT CTT T TT GAC<br>Tyr Trp Gln Thr Thr Lys Trp Thr Asp Leu P he Asp<br>1155                    116 0 | 4090 |
| ACT AAG GTT TTG ACA TTT GCA TAC AAG CAT G CA TTA<br>Thr Lys Val Leu Thr Phe Ala Tyr Lys His A la Leu<br>1165                    1170                  1175 | 4126 |
| GTA AAT AAG ATG TAC GGG AGA GGC CTT AAG T TT GCA<br>Val Asn Lys Met Tyr Gly Arg Gly Leu Lys P he Ala<br>1180                    118 5 | 4162 |
| ACC AAA CTC GTA GAA GAA AAA CCA ACA AAA G AA AAC<br>Thr Lys Leu Val Glu Glu Lys Pro Thr Lys G lu Asn<br>1190                    119 5                  1200 | 4198 |

| | |
|---|---|
| TGG AAA AAT TGT ATT CAA CTG ATG AAA TTA C TC GGA<br>Trp Lys Asn Cys Ile Gln Leu Met Lys Leu L eu Gly<br>1205                                     121 0 | 4234 |
| TGG ACC CAT TGT GCG TCT TTT ACT GAA AAC T GG CTC<br>Trp Thr His Cys Ala Ser Phe Thr Glu Asn T rp Leu<br>1215                                     122 0 | 4270 |
| CCC ATC ATG TAT CCT CCT GAT TAT TGT GTA T TC TAA<br>Pro Ile Met Tyr Pro Pro Asp Tyr Cys Val P he<br>1225                            1230                   1235 | 4306 |
| AATGGGAACC AAAACGTTAA ATTTCGAAAG CAGAAAATTT | 4346 |
| TATAGTGAAC AAATATATGA ACAAATGTGT GGCATTTCTA | 4386 |
| GTCTAACTAA TGCATGTCTT CATCCACTAT CGAATACTGA | 4426 |
| TCATTAAAAC TCTATGTATT TATCAGAGAA CTCAATGGTG | 4466 |
| TGTGGCTTCA TACATGTAAT GTAGACAGAC CTCTGACATC | 4506 |
| ATGCTGCTTT CCTGCTGCCT CCCACACTTG GCTAGGGAGG | 4546 |
| GCAGAGCCTG CCTGCCAGCC CCAACCTGGG TGGATGCAGC | 4586 |
| TGCTCACTGC AGGAGAGGTT TTCATCTCTT AATTTTTAAC | 4626 |
| TGTAAAACGT CATCCAGTTT TTATTTTATA AATCAAAAAG | 4666 |
| GTTAAAACAT GCTAAATTTT TCCAATTATA TAGAGGCCTT | 4706 |
| AAAAATGCTA CATTGGGTGT AGCTAAATTA TTTATTTGAC | 4746 |
| TAAAAATTAC GAGAACATAA TTTCCAGACT TCTAAAAATA | 4786 |
| AATTCAATTA ATGGGTATGG TGGGGAGGTA TAAATACATG | 4826 |
| GCAACTGGGA AAAGAAACGT GTTAATGTAA TCTTCACTCC | 4866 |
| GGAGTCACAA CAAGCAAGTT GTTTTTACAG CATCCTCAAG | 4906 |
| TACACAGCAT CAGAATAAGT TAAAATTTCA TGTGTTGGTG | 4946 |
| CCAGACAGTT GAATCTATCT GGTTTTGTAA AGATATACAC | 4986 |
| AGTATGTTTA TAACATTGAA ATCATGTAAA ATACATGAAT | 5026 |
| AAATGTGCAA AACAACAGGC ACAGCACACC ATATGCACTC | 5066 |
| TGATACCTGT TTTTTATAAA TAAAAGTAAA TATTGAAGCT | 5106 |
| AAA | 5109 |

(2) INFORMATION FOR SEQ ID NO:3:

(i) SEQUENCE CHARACTERISTICS:
        (A) LENGTH: 24
        (B) TYPE: NUCLEIC ACID
        (C) STRANDEDNESS: SIN GLE
        (D) TOPOLOGY: LINEAR (iv) ANTI-SENSE: NO (xi) SEQUENCE DESCRIPTION: SEQ ID NO:3:

| | |
|---|---|
| GACTGAGGAG CCCTTCCCTT TTCA | 24 |

(2) INFORMATION FOR SEQ ID NO:4:

(i) SEQUENCE CHARACTERISTICS:
        (A) LENGTH: 24
        (B) TYPE: NUCLEIC ACID
        (C) STRANDEDNESS: SIN GLE
        (D) TOPOLOGY: LINEAR (iv) ANTI-SENSE: YES

-continued (xi) SEQUENCE DESCRIPTION: SEQ ID NO:4:

GCCTTAGGAT AGAAGTCATA GCCA                                              24

(2) INFORMATION FOR SEQ ID NO:5:

(i) SEQUENCE CHARACTERISTICS:
            (A) LENGTH: 23
            (B) TYPE: NUCLEIC ACID
            (C) STRANDEDNESS: SINGLE
            (D) TOPOLOGY: LINEAR (iv) ANTI-SENSE: NO (xi) SEQUENCE DESCRIPTION: SEQ ID NO:5:

CCCTTTGTAG GAAAGGTTGT GCC                                               23

(2) INFORMATION FOR SEQ ID NO:6:

(i) SEQUENCE CHARACTERISTICS:
            (A) LENGTH: 25
            (B) TYPE: NUCLEIC ACID
            (C) STRANDEDNESS: SINGLE
            (D) TOPOLOGY: LINEAR (iv) ANTI-SENSE: YES (xi) SEQUENCE DESCRIPTION: SEQ ID NO:6:

GAATACGCAA TAATCGGGAG GATAC                                             25

(2) INFORMATION FOR SEQ ID NO:7:

(i) SEQUENCE CHARACTERISTICS:
            (A) LENGTH: 8
            (B) TYPE: AMINO ACID
            (C) STRANDEDNESS: SINGLE
            (D) TOPOLOGY: LINEAR (ii) MOLECULE TYPE: PEPTIDE (ix) FEATURE:
            (A) NAME/KEY: MODIFIED-SITE
            (B) LOCATION: 2 and 8
            (C) IDENTIFICATION METHOD :
            (D) OTHER INFORMATION: The Tyr at location
                2 maybe either unmodified or modified by
                a SO3H group; the carboxy-terminal of
                Phe at location 8 is modified by an NH2
                group.

(xi) SEQUENCE DESCRIPTION: SEQ ID NO:7:

Asp Tyr Met Gly Trp Met Asp Phe
1               5

(2) INFORMATION FOR SEQ ID NO:8:

(i) SEQUENCE CHARACTERISTICS:
            (A) LENGTH: 5
            (B) TYPE: AMINO ACID
            (C) STRANDEDNESS: SINGLE
            (D) TOPOLOGY: LINEAR (ii) MOLECULE TYPE: PEPTIDE (ix) FEATURE:
            (A) NAME/KEY: MODIFIED-SITE
            (B) LOCATION: 5
            (C) IDENTIFICATION METHOD :
            (D) OTHER INFORMATION: The carboxy-terminal
                of Phe at location 5 is modified by an
                NH2 group.

(xi) SEQUENCE DESCRIPTION: SEQ ID NO:8:

Gly Trp Met Asp Phe
5

TRIPEPTIDYLPEPTIDASE INHIBITORS

BACKGROUND OF THE INVENTION

The subject of the invention is also physiologically acceptable compositions comprising the said compounds.

The subject of the invention is also the use of the said compounds in the preparation of drugs intended for man or animals.

The important physiological role of endogenous neuropeptides, and in particular that of cholecystokinin (CCK), is known. This neuropeptide is both a digestive hormone and a neurotransmitter in the central and peripheral nervous systems. In the latter case, it is mainly in the form of an octapeptide sulphate (CCK-8-S) corresponding to the formula:

Asp-Tyr (SO$_3$H)-Met-Gly-Trp-Met-Asp-Phe-NH$_2$, (SEQ ID NO: 7)

CCK exerts various actions on motricity and digestive secretions (contraction of the bile vesicle, inhibition of gastric secretion, etc.) as well as on the central nervous system (analgesia, action on moods and cognition) and on the endocrine system (hypophyseal secretions). In addition, CCK and certain derivatives have a powerful anorexigenic activity by facilitating satiation by means of stimulating peripheral, and possibly central, receptors (J. J. Vanderhaegen and J. M. Crawley, Ann. N.Y. Acad. Sci., 1985, 448: 1–697).

Although interesting effects might be expected from the pharmacological stimulation of CCK receptors, no agent which stimulates these receptors is currently therapeutically available, mainly for reasons of poor bioavailability of CCK and derivatives thereof. In addition, it has even been shown that direct stimulation of CCK receptors was liable to lead to undesirable anxiogenic effects.

Other studies have been geared towards identifying the enzyme(s) responsible for the physiological inactivation of these endogenous neuropeptides and in particular CCK.

Accordingly, the involvement has been suggested of various enzymes which are thought to attack certain peptide bonds in the molecule CCK-8, such as, in particular, that of an acidic aminopeptidase, which is distinct from aminopeptidase A (Deschodt-Lanckman et al., Peptides, 1983, 4: 71), of enkephalinase and of an aminopeptidase (Matsas et al., FEBS Lett., 1984, 175: 124; Deschodt-Lanckman et al., Regul. Peptides, 1981, 2: 15), that of thiolpeptidases (Mc Dermott et al., Neurochem. Int., 1983, 5: 641; Durieux et al., Neuropeptides, 1986, 7: 1) as well as that of a metalloendopeptidase (Steardo et al., J. Neurochem., 1985, 45: 784).

More recently, Rose et al. (Proc. Natl. Acad., Sci. USA, 1988, 85: 8326; Neurosci., 1989, 29: 583) have suggested the involvement of a serine peptidase. They also observed that general reagents for the serine groups of proteins, such as diisopropyl fluorophosphorate (DFP) or elastase-inhibiting boronic acids or chloromethyl ketones (a family of serine peptidases) were capable of preventing the enzymatic degradation of endogenous CCK-8 released by depolarization of slices of brain.

However, these experiments did not allow the enzyme responsible to be identified and purified, and the compounds used in these experiments in vitro should not be considered as drugs, in particular on account of their toxicity, their absence of specificity and/or their poor bioavailability.

More recently still, an enzyme has been purified and identified from soluble extracts of human brain (Wilson C. et al., Neurochem. Res. 1993, 18(7), 743–749), this enzyme having much similarity with a protease known as tripeptidylpeptidase TPP II previously isolated from rat liver or from human erythrocytes (Balow R. M. et al., J. Biol. Chem., 1986, 261: 2409–2417; Tomkinson B. et al., Biochemistry 1991, vol. 30, 168–174). The 4611-bp sequence of a mouse TPP II has also been described (Tomkinson B., Biochem. J., 1994, vol. 304: 517–523), the coding sequence of which shows great homology with the abovementioned human TPP II.

This purified enzyme was shown to be capable of hydrolysing several neuropeptides including exogenous CCK-8, but neither its application in the inactivation of endogenous CCK-8 nor the possibility of obtaining CCK-type biological responses by inhibiting it had been either demonstrated or even suggested.

Thus, it is seen that there is a need in the prior art for specific, bioavailable, non-toxic chemical compounds which can be used as drugs for preventing the inactivation of these endogenous neuropeptides.

Moreover, a TPP II inhibitor of weak affinity has been described (Tomkinson et coll., Arch. Biochem. Biophys., 1994, 314: 276), but this inhibitor has an oligopeptidergic structure, which raises the idea that its bioavailability is low, especially orally, and that it therefore cannot constitute a drug, this use, incidentally, not having been considered by the authors.

The invention has now made it possible to achieve this objective by providing, in particular, a process for screening drugs which uses the isolated enzyme responsible, thus making it possible, depending on whether the said enzyme is or is not inhibited, to distinguish molecules liable to constitute effective drugs in the treatment of disorders or complaints involving endogenous neuropeptides, and in particular cholecystokinin.

The present invention also provides chemical compounds of formula defined below, which can be used to prevent the inactivation of endogenous neuropeptides, and thus satisfies the essential need existing in the prior art.

The inventors have prepared a pure membrane-derived tripeptidylpeptidase according to a process comprising the following steps:

i) preparation of membranes from brain (cerebral cortex), for example from rat brain;

ii) purification by high performance liquid chromatography/ies (HPLC);

iii) checking of the product obtained, by enzymatic reaction using a CCK substrate, for example the peptides CCK-8 (non-sulphated) of formula:

Asp-Tyr-Met-Gly-Trp-Met-Asp-Phe-NH$_2$ (SEQ ID NO: 7)

or CCK-5 of formula:

Gly-Trp-Met-Asp-Phe-NH$_2$ (SEQ ID NO: 8)

Studying the specificity of this purified enzyme on a series of model substrates showed that it behaves like an aminotripeptidylpeptidase.

The inventors have carried out sequencing work. One fragment of the purified protein is highly similar to a protease known as tripeptydylpeptidase II isolated previously from human erythrocytes or from rat liver (Balow R. M. et al., and Tomkinson et al.).

Using traditional molecular cloning methods, the inventors identified two distinct clones in a library of rat brain complementary DNA using two probes A and B of 350 and 380 bases respectively. They were obtained by a polymerase chain reaction (PCR) performed using the following primers:

SEQ ID No. 3 (probe A, sense primer): GACTGAG-GAGCCCTTCCCTTTTCA

SEQ ID No. 4 (probe A, antisense primer): GCCTTAG-GATAGAAGTCATAGCCA

SEQ ID No. 5 (probe B, sense primer): CCCTTTGTAG-GAAAGGTTGTGCC

SEQ ID No. 6 (probe B, antisense primer): GAATACG-CAATAATCGGGAGGATAC

Their sequencing indicated that the first clone is the rodent homologue of human tripeptidylpeptidase II (TPP II). On the other hand, in the second, the sequence differs in the 5' part (starting from nucleotide 293).

The nucleotide sequence coding for the isolated protein is given by the identifiers (SEQ ID No. 1 and SEQ ID No. 2).

The sequence includes a hydrophobic segment of about twenty amino acids, indicating the existence of a transmembrane segment. Thus, although this protein is probably derived from the same gene as the above one by a process of alternative splicing, it presents itself as a serine ectopeptidase.

Thus, the subject of the present invention is a process for screening drugs by measuring the activity of the membrane-bound tripeptidylpeptidase II enzyme or homologue, by using a model substrate for this enzyme.

Tripeptidylpeptidase can be prepared in accordance with the abovementioned process.

According to another embodiment, brain membranes, prepared by simple centrifugation of a homogenate, are incubated in the presence of an aminotripeptidylpeptidase substrate (such as AAF-Amc) and potential inhibitors of the enzymatic activity thus revealed.

The term homologous enzyme is understood to refer both to tripeptidylpeptidases which might be genetically modified and membrane-free, especially soluble, tripeptidylpeptidases, such as the one mentioned above, isolated by Barlöw R. M. et al.

DETAILED DESCRIPTION OF THE INVENTION

The inventors have been able to develop degradation inhibitors for endogenous neuropeptides, in particular CCK, by measuring the activity of the said enzyme in purified form, but also, more simply, in native form, on membrane preparations from tissues using a model substrate of TPP II.

Thus, the subject of the present invention is also chemical compounds corresponding to the general formula (I) below:

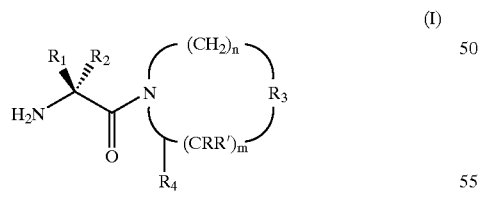

(I)

in which:
  $R_1$ represents a hydrogen or a linear or branched $C_1$–$C_4$ alkyl group;
  $R_2$ represents a hydrogen or a $C_1$–$C_2$ alkyl group;
    at least one from among $R_1$ and $R_2$ representing a hydrogen;
  n=0 or 1 and m=0 or 1 with n being different from m;
  R and R' each independently represent a hydrogen or a $C_1$–$C_2$ alkyl group;

$R_3$ represents a divalent radical consisting of a —(CH$_2$)$_2$—, —CH$_2$—CH(cis.F)— or —CH$_2$—CH(CH$_2$Ph)— alkyl chain, of a unit

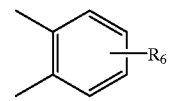

where $R_6$ represents H, F, OCH$_3$ or OCH$_2$Ph,

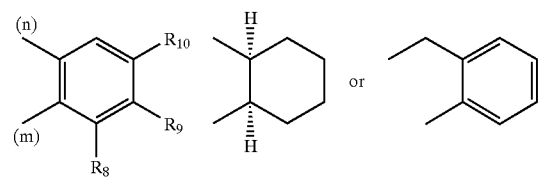

where $R_8$, $R_9$ and $R_{10}$ each represent a hydrogen or halogen atom, an O($C_1$–$C_4$ alkyl), OCH$_2$Ph, OH or $C_1$–$C_4$ alkyl group, including $R_6$, (m) and (n) indicating the bond orientation with respect to the (CH$_2$)$_n$ group (or to N if n=0) and to the (CRR')$_m$ group (or to CHR$_4$ if m=0)

$R_4$ represents an amide group CO—NH—$R_5$ where $R_5$ represents a hydrogen or a linear or branched $C_1$–$C_6$ alkyl, —(CH$_2$)$_3$—SCH$_3$, —CH$_2$Ph, —CH$_2$C$_6$H$_{11}$, (CH$_2$)$_3$OH,

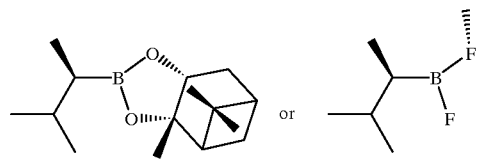

group.

Throughout the description, "Ph" denotes an optionally substituted phenyl radical.

The compounds of formula (I) have several asymmetric centres and the invention thus covers the racemic mixtures as well as the various stereoisomers and mixtures thereof in any proportion.

The subject of the present invention is also chemical compounds corresponding to the general formula (I') below:

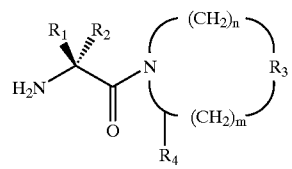

(I')

in which:
  $R_1$ represents a hydrogen or a linear or branched $C_1$–$C_4$ alkyl group;
  $R_2$ represents a hydrogen or a $C_1$–$C_2$ alkyl group;
    at least one from among $R_1$ and $R_2$ representing a hydrogen;
  n=0 or 1 and m=0 or 1 with n being different from m;
  $R_3$ represents a divalent radical consisting of a —(CH$_2$)$_2$—, —CH$_2$—CH(cis.F)— or —CH$_2$—CH(CH$_2$Ph)— alkyl chain, of a unit

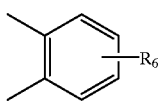

where $R_6$ represents H, F, $OCH_3$ or

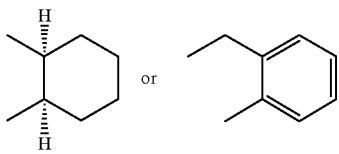

$R_4$ represents an amide group CO—NH—$R_5$ where $R_5$ represents a hydrogen or a linear or branched $C_1$-$C_6$ alkyl, —$(CH_2)_3$—$SCH_3$, —$CH_2Ph$, —$CH_2C_6H_{11}$,

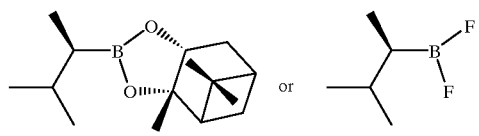

group.

According to a first preferred variant, the subject of the invention is compounds of formula (I) as defined above in which n and m are either equal to 0 or 1 with the proviso, however, that n is different from m.

According to a first aspect, the invention relates more particularly to a first group of these compounds in which $R_3$ represents the divalent radical —$(CH_2)_2$—.

A sub-family according to this aspect includes compounds where R and R' each represent a hydrogen atom.

Compounds of this type are, especially, the compounds given in the examples below, Nos. 1 to 7 (prepared according to route 1); No. 8 (route 2); No. 9 (route 5); No. 10 (route 6).

Among the latter group of compounds, those in which $R_1$ represents $CH_2CH_3$, $(CH_2)_2CH_3$, $(CH_2)_3CH_3$, CH $(CH_3)_2$, $CH_2CH(CH_3)_2$ and $CH(CH_3)CH_2CH_3$, $R_2$, R and R' represent a hydrogen, $R_4$ represents the amide group CO—NH—$R_5$ and $R_5$ represents a hydrogen, are known.

The compound of formula (I) in which $R_1$ represents $CH_2CH(CH_3)_2$, $R_2$, R and R' represent hydrogen, $R_3$ is the divalent radical —$(CH_2)_2$— and $R_5$ represents $CH_2CH_3$ is also known.

The compound of formula (I) in which $R_1$ represents $CH_3$, $R_2$, R and R' represent hydrogen, $R_3$ is the —$(CH_2)_2$— radical and $R_5$ represents the unit

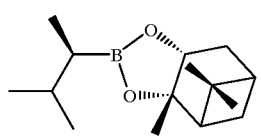

is also known.

According to another aspect, the invention relates more particularly to a second group of these compounds in which $R_3$ represents the cis-fluoroethylene unit —$CH_2$—CH (cis.F)— (substituted proline skeleton). One sub-family includes compounds in which R and R' are each a hydrogen, such as, for example, the compound of Example 11 (route 3) described below.

According to another aspect, the invention relates to a third group of these compounds in which $R_3$ represents the benzylethylene unit —$CH_2$—CH($CH_2Ph$)— (substituted proline skeleton). One sub-family includes compounds in which R and R' are each a hydrogen, such as, for example, the compound of Example 12 (route 4) described below.

According to a second preferred variant, the subject of the invention is compounds of formula (I) as defined above in which n=0 and m=1.

According to one aspect of this variant, the invention relates to compounds in which $R_3$ represents the unit

(tetrahydroisoquinoline skeleton)

where (n) and (m) indicate the bond orientation as above.

One sub-family includes compounds in which R and R' are each hydrogen, especially including the compound of Example 13 (route 3) described below.

According to a second particularly preferred aspect, the subject of the invention is compounds of formula (I) in which R and R' represent hydrogen and $R_3$ represents the unit

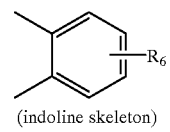

(indoline skeleton)

examples of which are, in particular, the compounds of Examples 14 to 17 (route 3); Examples 18 to 21 (route 7); described below.

According to another particularly preferred aspect of this second variant, the invention relates to compounds of formula (I) in which $R_3$ represents the unit

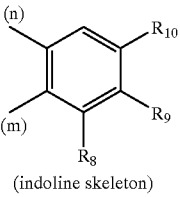

(indoline skeleton)

examples of which are, in particular, the compounds of Examples 24 to 26 (route 8) and of Example 27 (route 9); 28 (route 11); 29 and 30 (route 10); 31 and 32 (route 9); 33 and 34 (route 12); 35 (route 8); 38 (route 13) and 37 (route 14) described below.

This class of compounds includes compounds of formula (I) in which $R_3$ represents the unit

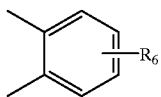

when R and R' each represent a hydrogen, two of the substituents $R_8$, $R_9$ and $R_{10}$ then being a hydrogen.

According to another aspect of this second variant, the invention relates to compounds in which $R_3$ represents the unit

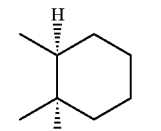

(perhydroindoline skeleton)

One sub-family includes compounds in which R and R' each represent hydrogen, such as, in particular, the compound of Example 22 (route 3) given below.

Lastly, according to a third variant, the subject of the invention is compounds of formula (I) in which n=and m=0 and $R_3$ represents the unit

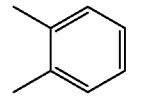

(isoindoline skeleton)

such as the compound of Example 23 (route 4) described below.

The compounds of formula (I) in which $R_2$ represents a hydrogen are also particularly preferred.

The inhibitory effect of these compounds was evaluated by measuring the membrane-bound TPP II activity and expressed in terms of their apparent dissociation constant Ki as described below.

The preferred compounds according to the invention are the following compounds:

2(S)-aminobutyryl-L-prolinamide;
L-valyl-L-proline n-hexylamide;
1-(2(S)-aminobutyryl)-L-proline 3-(methylthio)propylamide;
1-(2(S)-aminobutyryl)-L-proline n-pentylamide;
1-(2(S)-aminobutyryl)-L-proline n-butylamide;
1-(2(S)-aminobutyryl)-L-proline [2(S)-methyl]butylamide;
1-(2(S)-aminobutyryl)-L-proline n-propylamide;
1-(2(S)-aminobutyryl)-L-proline isobutylamide;
L-valyl-L-proline n-butylamide;
L-alanyl-L-prolyl-L-borovaline pinanediol ester;
L-alanyl-L-prolyldifluoro-L-borovaline borohydride;
1-(2(S)-aminobutyryl)-(4(S)-fluoro)-L-proline n-butylamide;
1-(2(S)-aminobutyryl)-(4(S)-benzyl)-L-proline n-butylamide;
2-(2(S)-aminobutyryl)-1,2,3,4-tetrahydro-3(S)-isoquinolinecarboxylic acid n-butylamide;
1-(2(S)-aminobutyryl)-2(S)-indolinecarboxylic acid n-butylamide;
1-(2(S)-aminobutyryl)-2(S)-indolinecarboxylic acid n-propylamide;
1-(2(S)-aminobutyryl)-2(S)-indolinecarboxylic acid methylamide;
1-(2(S)-aminobutyryl)-2(S)-indolinecarboxylic acid ethylamide;
1-(2(S)-aminobutyryl)-2(R/S)-(5-methoxy)indolinecarboxylic acid n-butylamide;
1-(2(S)-aminobutyryl)-2(R/S)-(6-methoxy)indolinecarboxylic acid n-butylamide;
1-(2(S)-aminobutyryl)-2(R/S)-(5-fluoro)indolinecarboxylic acid n-butylamide;
1-(2(S)-aminobutyryl)-2(R/S)-(5-benzyloxy)indolinecarboxylic acid n-butylamide;
1-(2(S)-aminobutyryl)-2(S)-[(3aS, 7aS)-perhydro]indolinecarboxylic acid n-butylamide;
2-(2(S)-aminobutyryl)-1(R/S)-isoindolinecarboxylic acid n-butylamide;

as well as the corresponding salts or hydrates thereof.

These compounds constitute preferred inhibitors according to the invention and have a constant Ki with respect to the tripeptidylpeptidase enzyme. according to the invention, of less than or equal to 1 $\mu$M.

Other compounds that are most particularly preferred are compounds of formula (I) having an indoline skeleton, namely the following compounds:

1-(2(S)-aminobutyryl)-2(S)-indolinecarboxylic acid n-butylamide;
1-(2(S)-aminobutyryl)-2(S)-indolinecarboxylic acid n-propylamide;
1-(2(S)-aminobutyryl)-2(S)-indolinecarboxylic acid ethylamide;
1-(2(S)-aminobutyryl)-2(R/S)-(5-methoxy)indolinecarboxylic acid n-butylamide;
1-(2(S)-aminobutyryl)-2(R/S)-(5-fluoro)indolinecarboxylic acid n-butylamide;

as well as the corresponding salts or hydrates thereof.

These compounds are particularly preferred inhibitors having a constant Ki which does not exceed 0.02 $\mu$M.

Other compounds that are most particularly preferred are also the compounds of formula (I) below having an indoline skeleton:

1-(L-valyl) -5-methoxyindoline-2(R/S)-carboxylic acid butylamide;
1-(L-alanyl)-5-methoxyindoline-2(R/S)-carboxylic acid butylamide;
1-(L-alanyl)-5-methoxyindoline-2(S)-carboxylic acid butylamide;
1-(2(S)-aminobutyryl)-4-methoxyindoline-2(R/S)-carboxylic acid butylamide;
1-(2(S)-aminobutyryl)-3,3-dimethylindoline-2(R/S)-carboxylic acid butylamide;
1-(2(S)-aminobutyryl)-3(R)-methylindoline-2(R)-carboxylic acid butylamide and 1-(2(S)-aminobutyryl)-2(S)-methylindoline-2(S)-carboxylic acid butylamide;
1-(2(S)-aminobutyryl)-3(R)-methylindoline-2(S)-carboxylic acid butylamide and 1-(2(S)-aminobutyryl)-3(S)-methylindoline-2(R)-carboxylic acid butylamide;
1-(2(S)-aminobutyryl)-4-ethoxyindoline-2(S)-carboxylic acid butylamide;
1-(2(S)-aminobutyryl)-4,5-dimethoxyindoline-2(R/S)-carboxylic acid butylamide;
1-(2(S)-aminobutyryl)-5-hydroxyindoline-2(S)-carboxylic acid butylamide;
1-(2(S)-aminobutyryl)-5-hydroxyindoline-2(R/S)-carboxylic acid butylamide;

1-(2(S)-aminobutyryl)-5-methylindoline-2(R/S)-carboxylic acid butylamide;
1-(2(S)-aminobutyryl)-5-chloroindoline-2(S)-carboxylic acid butylamide;
1-(2(S)-aminobutyryl)indoline-2(S)-carboxylic acid (3-hydroxy)propylamide;
as well as the corresponding salts or hydrates thereof.

The subject of the present invention is also processes for the preparation of the compounds of general formula (I) described above.

Thus, the invention relates more particularly to a process (route 1) for the preparation of a compound of general formula (I) defined above, in which:

$R_1$ represents a linear or branched $C_1$–$C_4$ alkyl group;
$R_2$ represents a hydrogen;
R and R' represent a hydrogen;
n=0 or 1 and m=0 or 1 with n being different from m and $R_3$ represents —(CH$_2$)$_2$—; and
$R_4$ represents CO—NH—$R_5$
$R_5$ represents a hydrogen or a linear or branched $C_1$–$C_6$ alkyl, —(CH$_2$)$_3$—S—CH$_3$ or —CH$_2$Ph group;
characterized in that it comprises:

i) the formation of a compound of formula (III)

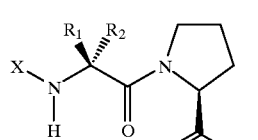
(III)

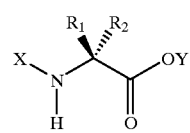
(III)

in which $R_1$ and $R_2$ have the meanings given above and X represents a protecting group, starting with a compound of formula (II)

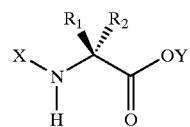
(II)

(II)

which is esterified on its acid function with a group Y and in which X, $R_1$ and $R_2$ have the meanings given above, by reaction with L-proline;
(ii) amidation of the acid function of compound (III) with the appropriate amine $R_5NH_2$
where $R_5$ has the meaning given above, in order to form the derivative (IV)

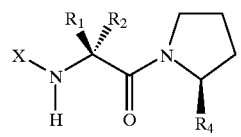
(III)

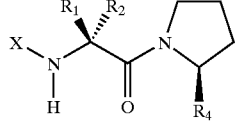
(IV)

which is protected on its primary amine function with the group X;
iii) removal of the group X from the derivative (IV), in order to obtain the desired compound (I).

The group Y preferably represents the unit

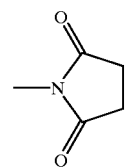

Step i) is carried out in the presence of triethylamine and of water.

Moreover, in step ii), the mixed anhydride of the acid (III) and of isobutyl chloroformate is formed and is then reacted in situ with the amine $R_5NH_2$.

In the compounds prepared according to this route 1, $R_1$ preferably represents an ethyl or isopropyl group.

The invention also relates to a process (route 2) for the preparation of a compound of general formula (I) given above, in which:

$R_1$ represents a linear or branched $C_1$–$C_4$ alkyl group;
$R_2$ represents a hydrogen or a methyl group;
R and R' represent a hydrogen;
n=0 or 1 and m=0 or 1 with n being different from m, and $R_3$ represents a —(CH$_2$)$_2$— group; and
$R_4$ represents a group CO—NH—$R_5$ in which $R_5$ represents a hydrogen or a linear or branched $C_1$–$C_6$ alkyl group;
characterized in that it comprises:
i) formation of a compound of formula (IV)

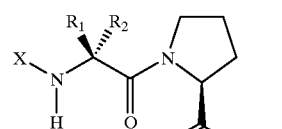
(IV)

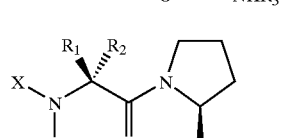
(IV)

in which $R_1$, $R_2$ and $R_5$ have the meanings given above and X represents a protecting group, starting with a compound of formula (II)

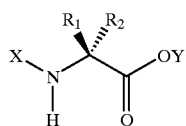
(II)

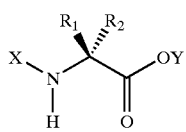
(II)

which is esterified on its acid function with a group Y and in which $R_1$, $R_2$ and X have the meanings given above, by reaction with a prolineamide of formula (V)

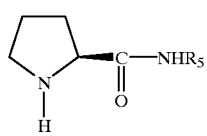
(V)

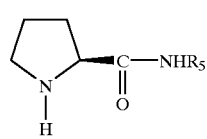
(V)

in which $R_5$ has the meaning given above;

ii) removal of the protecting group X from compound (IV) in order to obtain the desired compound (I).

The prolineamide (V) can be prepared by reacting L-proline

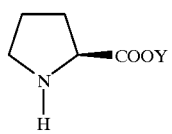

which is protected on its amine function with a protecting group X and esterified on its acid function with a group Y, with the appropriate amine $R_5NH_2$.

The group Y preferably represents the unit

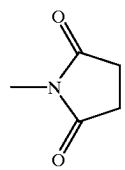

In order to form compound (IV), the prolineamide thus obtained is reacted with compound (II), in the presence of water and triethylamine in a solvent such as tetrahydrofuran or dioxane.

In the compounds prepared according to this route 2, $R_1$ preferably represents an ethyl or isopropyl group and $R_5$ preferably represents a hydrogen or an n-butyl group.

The invention also relates to a process (route 3) for the preparation of a compound of general formula (I) given above, in which:

$R_1$ represents a linear or branched $C_1$–$C_4$ alkyl group;

$R_2$ represents a hydrogen;

R and R' represent a hydrogen;

n=0 and m=1 and $R_3$ represents a group

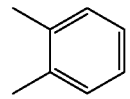

—$CH_2$—CH(cis.F)— 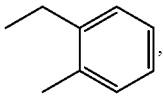 , 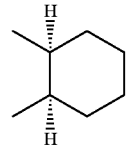

$R_4$ represents a group CO—NH—$R_5$ in which $R_5$ represents a hydrogen or a linear or branched $C_1$–$C_6$ alkyl group;

characterized in that it comprises:

i) preparation of a compound of formula (X)

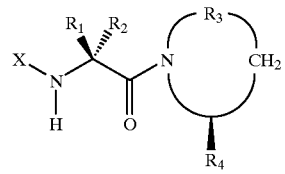
(X)

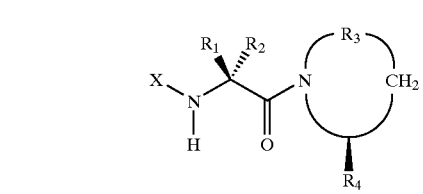
(X)

in which $R_1$, $R_2$, $R_3$ and $R_4$ have the meanings given above and X represents a protecting group, by reaction of a compound of formula (VIII)

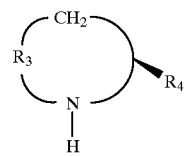
(VIII)

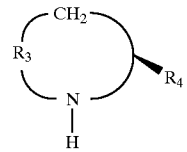
(VIII)

with a compound of formula (IX)

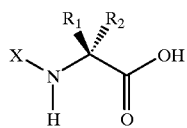
(IX)

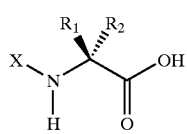
(IX)

in which $R_1$, $R_2$, $R_4$ and X have the meanings given above;

ii) removal of the group X from the compound (X), in order to form the desired compound (I).

According to this route 3, compound (VIII) is prepared by amidation of the acid function of a compound (VI)

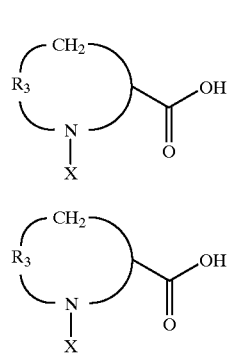
(VI)

(VI)

which is protected on its amine function with a protecting group X and in which $R_3$ has the meaning given above, with the appropriate amine $R_5NH_2$, in order to form the derivative (VII)

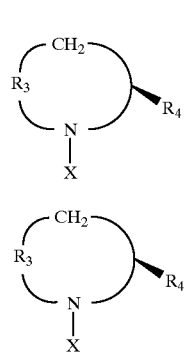
(VII)

(VII)

in which $R_3$ $R_4$ and X have the meanings given above, followed by removal of the protecting group X.

For this, the mixed anhydride of the acid (VI) and of isobutyl chloroformate is advantageously formed in the presence of N-ethylmorpholine in tetrahydrofuran, and is then reacted in situ with the appropriate amine $R_5NH_2$. These conditions can also constitute those of step i) except that compound (VII) is reacted instead of the amine $R_5NH_2$.

In the compounds prepared according to this route 3, $R_1$ preferably represents an ethyl group and $R_5$ preferably represents a hydrogen or a methyl, ethyl, n-propyl or n-butyl group.

The invention also relates to a process (route 4) for the preparation of a compound of general formula (I) given above, in which:

$R_1$ represents a linear or branched $C_1$–$C_4$ alkyl group;

$R_2$ represents a hydrogen;

n=1 and m=0 and $R_3$ represents a —CH(CH$_2$Ph)—CH$_2$— group or

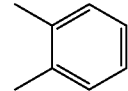

$R_4$ represents an amide group CO—NH—$R_5$ in which $R_5$ represents a hydrogen or a linear or branched $C_1$–$C_6$ alkyl group;

characterized in that it comprises:

i) production of a compound (XII)

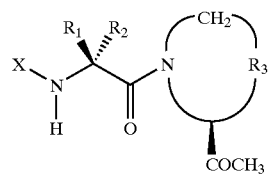
(XII)

which is protected on its primary amine function with a protecting group X and in which $R_1$, $R_2$ and $R_3$ have the meanings given above, by reaction of the compound of formula (IX)

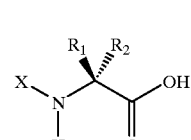
(IX)

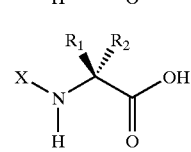
(IX)

with the compound of formula (XI)

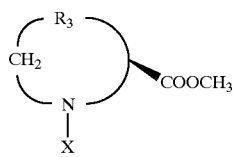
(XI)

in which $R_1$, $R_2$ and $R_3$ have the meanings given above and X represents a protecting group;

ii) hydrolysis of the ester function of compound (XII) thus obtained, in order to form the compound of formula (XIII)

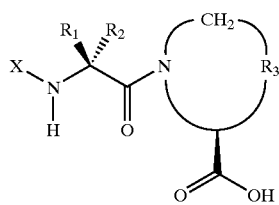
(XIII)

in which $R_1$, $R_2$, $R_3$ and X have the meanings given above;

iii) amidation of the acid function of compound (XIII) using the appropriate amine $R_5NH_2$, in order to form the derivative of formula (XIV)

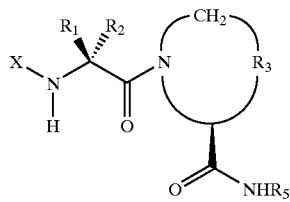
(XIV)

$R_1$, $R_2$, $R_3$, $R_5$ and X have the meanings given above;

iv) removal of the protecting group X from the compound (XIV) in order to form the desired compound (I).

Step ii) of hydrolysis is advantageously carried out in the presence of sodium hydroxide in methanol.

In step iii), the mixed anhydride of the acid (XIII) and of isobutyl chloroformate is formed and is then reacted in situ with the appropriate amine $R_5NH_2$.

In the compounds prepared according to this route 4, $R_1$ preferably represents an ethyl group and $R_5$ preferably represents a hydrogen or an n-butyl group.

The invention also relates to a process (route 5) for the preparation of a compound of general formula (I) given above, in which:

$R_1$ represents a methyl group;

$R_2$ represents a hydrogen;

R and R' represent a hydrogen;

n=0 or 1 and m=0 or 1 with n being different from m, and $R_3$ represents the —$(CH_2)_2$— group; and $R_4$ represents an amide group CO—NH—$R_5$ in which $R_5$ represents the unit

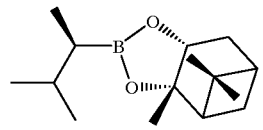

characterized in that it comprises:

i) amidation of the acid function of the compound of formula (XIX)

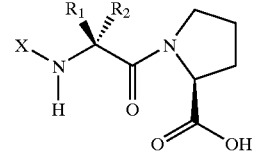
(XIX)

which is protected on its primary amine function with a protecting group X and in which $R_1$ and $R_2$ have the meanings given above, using the amine (XVIII)

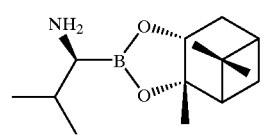
(XVIII)

in order to form the derivative (XX)

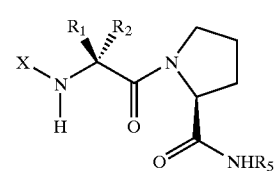
(XX)

in which $R_1$, $R_2$, $R_5$ and X have the meanings given above;

ii) removal of the protecting group X from compound (XX) in order to obtain the desired compound (I).

Step i) is advantageously performed using isobutyl chloroformate, in order to form the mixed anhydride of the acid XIX, in the presence of N-ethylmorpholine in tetrahydrofuran.

Step ii) can, itself, be carried out using trifluoroacetic acid in methylene chloride.

The amine (XVIII) is prepared i) by reaction of isopropylboronic acid with (+)-pinanediol in ether, in order to obtain the derivative (XV)

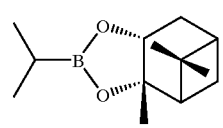
(XV)

ii) by reaction of compound (XV) with butyllithium and methylene chloride, followed by zinc chloride $ZnCl_2$ in tetrahydrofuran, at low temperature, in order to for m derivative (XVI)

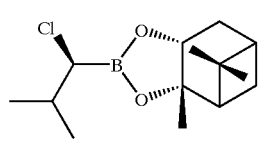
(XVI)

iii) substitution of the chlorine in compound (XVI) using butyllithium and hexamethyldisilazane in tetrahydrofuran at low temperature, in order to form compound (XVII)

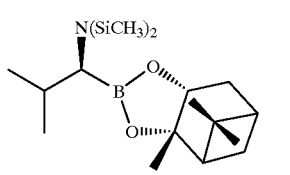
(XVII)

iv) liberation of the amine function in compound (XVII) in order to obtain the desired compound (XVIII).

Isopropylboronic acid is obtained by addition of triethyl borate to isopropylmagnesium chloride in ether at low temperature.

Step iv) mentioned above is advantageously performed using trifluoroacetic acid in pentane.

The invention also relates to a process (route 6) for the preparation of a compound of general formula (I) given above, in which:

$R_1$ represents a methyl group;
$R_2$ represents a hydrogen;
R and R' represent a hydrogen;.
n=0 or 1 and m=0 or 1 with n being different from m, and $R_3$ represents a —$(CH_2)_2$— group; and
$R_4$ represents an amide group CO—NH—$R_5$ in which $R_5$ represents $(CH_3)_2$—CH—$BF_2$;

characterized in that it comprises:

i) removal of the pinane unit from the compound of formula (I) in which $R_1$, $R_2$, n, m, $R_3$ and $R_4$ have the meanings given above and $R_5$ represents

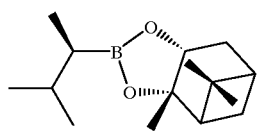

by the action of boron trichloride in methylene chloride, followed by hydrolysis, in order to obtain derivative (XXI)

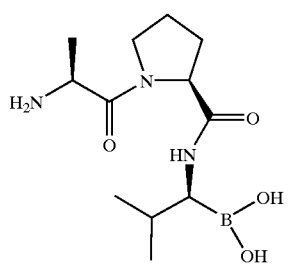
(XXI)

ii) reaction of compound (XXI) with hydrofluoric acid in order to form the desired compound (I).

The invention relates to a process (route 7) for the preparation of a compound of general formula (I) given above, in which:

$R_1$ represents a linear or branched $C_1$–$C_4$ alkyl group;
$R_2$ represents a hydrogen;
R and R' represent a hydrogen;
n=0 and m=1 and $R_3$ represents the unit

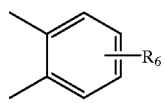

in which $R_6$ represents an $OCH_3$, $OCH_2Ph$ or F group; and $R_4$ represents an amide group CO—NH—$R_5$ in which $R_5$ represents a linear or branched $C_1$–$C_6$ alkyl group;

characterized in that it comprises:

i) formation of the amide of formula (XXXXIV)

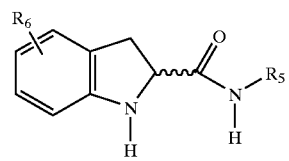
(XXXXIV)

starting with the ester of formula (XXXXIII)

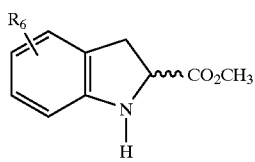
(XXXXIII)

in which formulae $R_6$ has the meaning given above, by reaction with the appropriate amine $R_5NH_2$;

ii) reaction of compound (XXXXIV) with the compound of formula (IX)

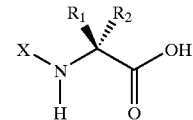
(IX)

in which $R_1$ and $R_2$ have the abovementioned meanings and X represents a protecting group, in order to form the compound of formula (XXXXV)

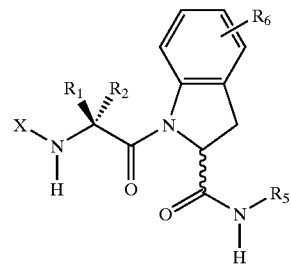
(XXXXV)

in which $R_1$, $R_2$, $R_5$, $R_6$ and X have the meanings given above;

iii) removal of the group X in order to form the desired compound (I).

Step ii) is advantageously carried out in the presence of bis(2-oxo-3-oxazolidinyl)phosphinyl chloride and triethylamine in methylene chloride.

As regards the methyl ester (XXXXIII), it can be obtained
i) by the action of sodium nitrite in the presence of hydrochloric acid, on the compound of formula (XXXIX)

(XXXIX)

in order to form the compound of formula (XXXX)

(XXXX)

in which formulae $R_6$ has the meaning indicated above ii) by addition of ethyl 2-methylacetoacetate to compound (XXXX) thus obtained, in the presence of sodium nitrite in ethanol, in order to form the compound of formula (XXXXI)

(XXXXI)

in which $R_6$ has the abovementioned meaning;

iii) by cyclization in acidic medium, in order to form the ethyl ester (XXXXII)

(XXXXII)

iv) by exchange starting with the ethyl ester (XXXXII) thus obtained, in the presence of magnesium in ethanol.

The ethyl ester undergoes an ester exchange and a reduction in the presence of magnesium and methanol in order to lead to the methyl ester (XXXXIII).

In the compounds prepared according to this route 7, $R_1$ preferably represents an ethyl group and $R_5$ preferably represents an n-butyl group.

The invention relates to a process (route 8) for the preparation of a compound of general formula (I) given above, in which:

$R^1$ represents a linear or branched $C_1$–$C_4$ alkyl group;
$R_2$, R and R' each represent a hydrogen;
n=0 and m=1, and $R_3$ represents the unit in which $R_8$ and $R_{10}$ represent a hydrogen and $R_9$ represents a group $O(C_1$–$C_4$ alkyl) or $C_1$–$C_4$ alkyl
$R_4$ represents an amide group CO—NH—$R_5$ in which $R_5$ represents a linear or branched $C_1$–$C_6$ alkyl group;
characterized in that it comprises:
i) formation of the amide of formula (49)

(49)

starting with the ester of formula (48)

(48)

in which $R_9$ and $R_5$ have the meaning given above, by reaction with the appropriate amine $R_5NH_2$;

ii) reaction of compound (49) with the compound of formula (IX)

(IX)

in which $R_1$ and $R_2$ have the abovementioned meanings and X represents a protecting group, in order to form the compound of formula (50)

(50)

in which $R_1$, $R_2$, $R_9$ and X have the meanings given above;

iii) removal of the group X in order to form the desired compound (I).

Step ii) is advantageously carried out in the presence of bis(2-oxo-3-oxazolidinyl)phosphonyl chloride and triethylamine in methylene chloride.

The methyl ester (48) can be obtained from the corresponding acid (46)

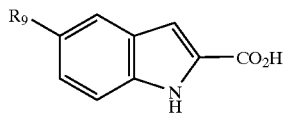
(46)

in which $R_9$ has the meaning given above i) by treatment in ethanol or methanol with concentrated sulphuric acid, in order to lead to the corresponding ester (47)

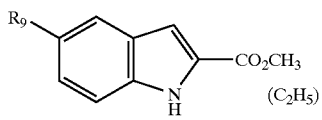
(47)

in which $R_9$ is as defined above ii) after which, compound (47) is treated with magnesium in methanol.

In the compounds prepared according to this route 8, $R_1$ preferably represents a $CH_3$, $C_2H_5$ or $(CH_3)_2CH$ group, $R_9$ preferably represents an $OCH_3$ or $CH_3$ group and $R_5$ preferably represents an n-butyl group.

The subject of the invention is also a process (route 9) for the preparation of a compound of general formula (I) given above, in which $R_1$ represents a linear or branched $C_1$–$C_4$ alkyl group;

$R_2$, R and R' each represent a hydrogen;

n=0 and m=1, and $R_3$ represents the unit

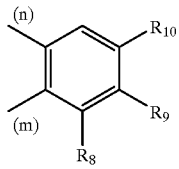

in which $R_8$ and $R_9$ represent a hydrogen or an $O(C_1$–$C_4$ alkyl) group, it not being possible for $R_8$ and $R_9$ simultaneously to represent a hydrogen, and $R_{10}$ represents a hydrogen $R_4$ represents an amide group $CONHR_5$ in which $R_5$ is a linear or branched $C_1$–$C_6$ alkyl group, characterized in that it comprises:

i) formation of compound (54)

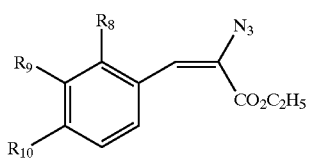
(54)

by reaction of the corresponding aldehyde (53)

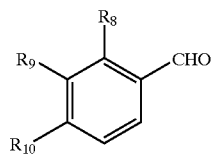
(53)

in which $R_8$, $R_9$ and $R_{10}$ are as defined above with ethyl azidoacetate (52)

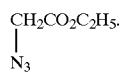
(52)

ii) cyclization of compound (54) in order to lead to compound (55)

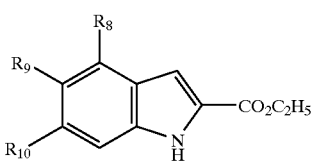
(55)

in which $R_8$, $R_9$ and $R_{10}$ have the meanings given above iii) formation of methyl ester (56)

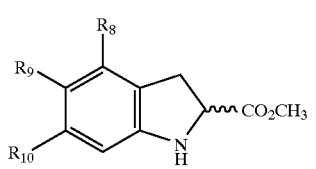
(56)

in which $R_8$, $R_9$ and $R_{10}$ have the meanings given above starting with compound (55) in the presence of magnesium in methanol iv) reaction of the ester (56) obtained with the appropriate amine $R_5NH_2$ in order to form the amide (57)

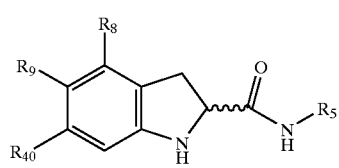
(57)

in which $R_8$, $R_9$ and $R_{10}$ are as defined above v) reaction of compound (57) with the compound of formula (IX)

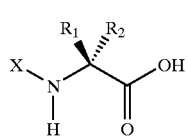
(IX)

in which $R_1$ and $R_2$ have the abovementioned meaning and X represents a protecting group, in order to form compound (58)

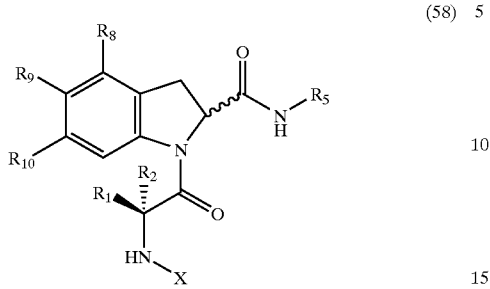
(58)

in which $R_1$, $R_2$, $R_5$, $R_8$, $R_9$, $R_{10}$ and X have the meaning given above, vi) removal of the group X in order to form the desired compound (I).

Compound (52) can be obtained by the action of sodium azide on ethyl bromoacetate in acetonitrile.

According to step i), sodium ethoxide is first formed and compounds (52) and (53) are then reacted.

The cyclization step ii) is advantageously carried out by refluxing in toluene.

Step v) is advantageously carried out in the presence of bis(2-oxo-3-oxazolidinyl)phosphonyl chloride and triethylamine in methylene chloride.

In the compounds prepared according to this route 9, $R_1$ preferably represents the $CH_2CH_3$ group, $R_8$ an $OCH_3$ or $OC_2H_5$ group and $R_9$ a hydrogen, or alternatively $R_8$ and $R_9$ both represent an $OCH_3$ group, and $R_5$ preferably represents an n-butyl group.

The subject of the invention is also a process (route 10) for the preparation of a compound of formula (I) given above, in which:

$R_1$ represents a linear or branched $C_1$–$C_4$ alkyl group;

$R_2$ represents a hydrogen;

one of the substituents R or R' represents a hydrogen and the other a $C_1$–$C_2$ alkyl group;

n=0 and m=1 and $R_3$ represents the unit

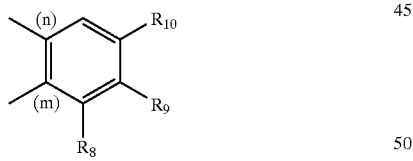

with $R_8$, $R_9$ and $R_{10}$ representing a hydrogen $R_4$ represents an amide group $CONHR_5$ in which $R_5$ is a linear or branched $C_1$–$C_6$ alkyl group, characterized in that it comprises:

i) formation of compound (59)

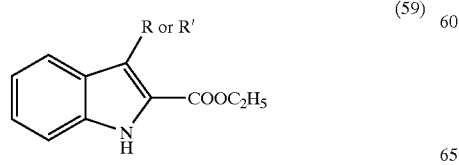
(59)

in which R and R' are as defined above by reaction between phenylhydrazine and 2-ketobutyric acid in acidic medium ii) formation of compound (60) from the compound (59) obtained

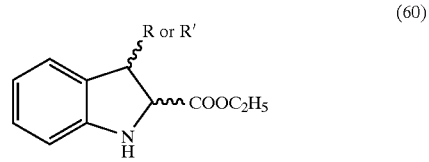
(60)

in which R and R' are as defined above in the presence of magnesium in methanol, iii) formation of the amide (61) corresponding to compound (60) by reaction with the appropriate amine $R_5NH_2$

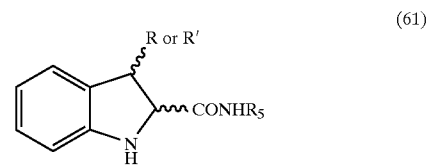
(61)

in which R and R' are as defined above iv) separation of the cis isomers (61a), on the one hand, and the trans isomers (61b), on the other hand, of compound (61)

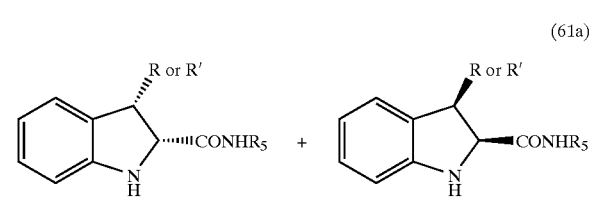
(61a)

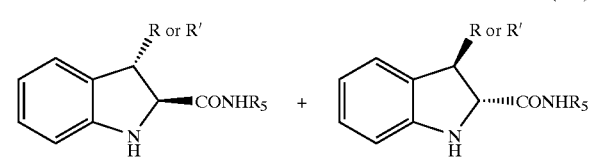
(61b)

v) reaction, respectively, of compounds (61a) and (61b) with compound (IX)

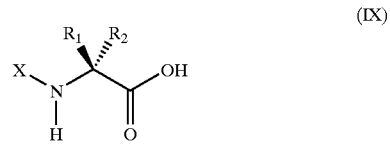
(IX)

in which $R_1$ and $R_2$ have the meaning given above and X represents a protecting group, in order to form mixtures (62a) and (62b) respectively

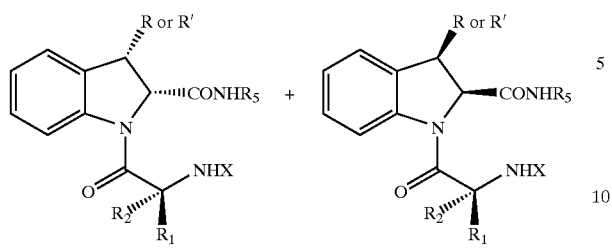
(62a)

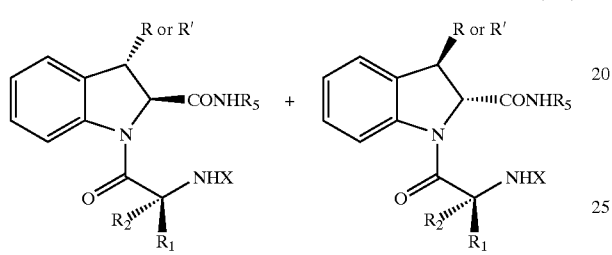
(62b)

in which $R_1$, $R_2$, R, R' and $R_5$ have the meaning given above vi) removal of the protecting group X, leading to the desired compound (I) in the form of cis pairs (63a) and trans pairs (63b), respectively.

Step v) is advantageously carried out in the presence of bis(2-oxo-3-oxazolidinyl)phosphinyl chloride and triethylamine in methylene chloride.

In the compounds prepared according to this route 10, $R_1$ preferably represents the $CH_2CH_3$ group, R or R' represents the $CH_3$ group (the other substituent being a hydrogen) and $R_5$ preferably represents the n-butyl group.

The subject of the invention is also a process (route 11) for the preparation of a compound of formula (I) given above, in which:

$R_1$ represents a linear or branched $C_1$–$C_4$ alkyl group;

$R_2$ represents a hydrogen;

R and R' each represent a $C_1$–$C_2$ alkyl group, which may be identical or different;

n=0 and m=1 and $R_3$ represents the unit

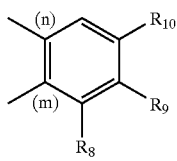

in which $R_8$, $R_9$ and $R_{10}$ each represent a hydrogen;

$R_4$ represents an amide group $CONHR_5$ in which $R_5$ is a linear or branched $C_1$–$C_6$ alkyl group;

characterized in that it comprises:

i) formation of compound (65) of the following formula:

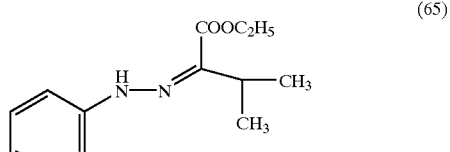
(65)

by reaction of phenylhydrazine with ethyl 2-oxo-3-methylbutanoate (64)

ii) cyclization of compound (65) in acidic medium, in order to form compound (66) below:

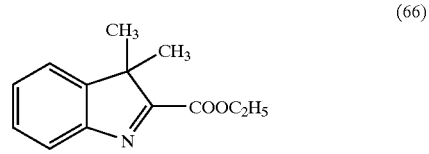
(66)

iii) hydrogenation of compound (66), leading to compound (67) below

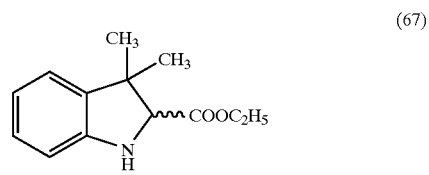
(67)

iv) formation of the corresponding amide (68) by the action of $LiNHR_5$ in which $R_5$ has the abovementioned meaning

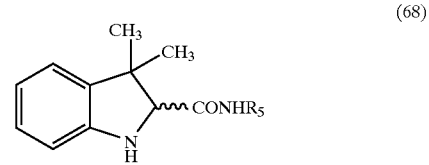
(68)

v) reaction of compound (68) with the compound of formula (IX)

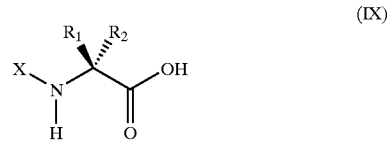
(IX)

in which $R_1$ and $R_2$ have the meaning given above and X is a protecting group, in order to form compound (69)

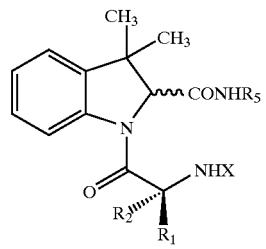
(69)

vi) removal of the group X in order to form the desired compound (I).

Route 11 is illustrated above in the case where R and R' represent a methyl group, but R and R' can each represent an alkyl group, which may be identical or different. In this case, step i) is carried out with the appropriate compound, in particular a compound (64)

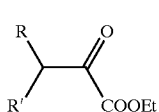
(64)

Step i) is advantageously carried out at a temperature of about 60° C. in toluene.

Step v) is advantageously carried out in the presence of bis(2-oxo-3-oxazolidinyl)phosphinyl chloride and triethylamine in methylene chloride.

Ethyl 2-oxo-3-methylbutanoate (64) can be obtained from diethyl oxalate with isopropylmagnesium chloride in ether at low temperature.

In the compounds prepared according to this route 11, $R_1$ preferably represents an ethyl group and $R_5$ preferably represents an n-butyl group.

The invention also relates to a process (route 12) for the preparation of a compound of formula (I) given above, in which:

$R_1$ represents a linear or branched $C_1$–$C_4$ alkyl group;

$R_2$, R and R' each represent a hydrogen;

n=0 and m=1, and $R_3$ represents the unit

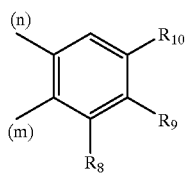

in which $R_9$ represents an OH group and $R_8$ and $R_{10}$ both represent a hydrogen;

$R_4$ represents an amide group $CONHR_5$ in which $R_5$ is a linear or branched $C_1$–$C_6$ alkyl group;

characterized in that it comprises:

i) formation of compound (71)

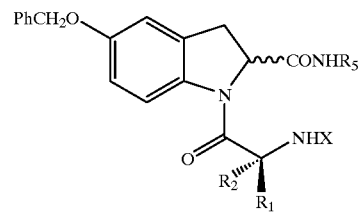
(71)

in which $R_9$ represents an $OCH_2Ph$ group, $R_5$ has the meaning given above and X represents a protecting group, by reaction of compound (70)

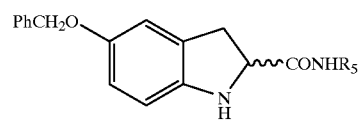
(70)

in which $R_5$ is as defined above, with a compound (IX)

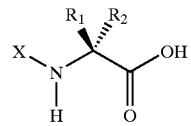
(IX)

in which $R_1$ and $R_2$ have the meaning given above and X represents a protecting group, ii) removal of the groups $CH_2Ph$ and X from compound (71) in order to form the desired compound (I).

Step i) is advantageously carried out in the presence of dicyclohexylcarbodiimide in methylene chloride.

Compound (70) can be obtained by the process described above (route 7).

In the compounds prepared according to this route 12, $R_1$ preferably represents an ethyl group and $R_5$ an n-butyl group.

The invention also relates to a process (route 13) for the preparation of a compound of formula (I) given above, in which:

$R_1$ represents a linear or branched $C_1$–$C_4$ alkyl group;

$R_2$, R and R' each represent a hydrogen;

n=0 and m=1, and $R_3$ represents the unit

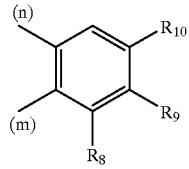

in which $R_9$ represents a halogen atom and $R_8$ and $R_{10}$ each represent a hydrogen $R_4$ represents an amide group $CONHR_5$ in which $R_5$ is a linear or branched $C_1$–$C_6$ alkyl group;

characterized in that it comprises:

i) formation of the methyl ester (73)

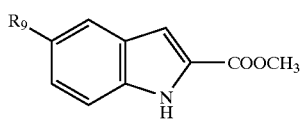
(73)

from the corresponding acid (72)

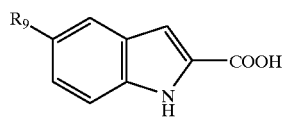
(72)

in which $R_9$ is as defined above, with concentrated sulphuric acid in methanol, ii) formation of compound (74)

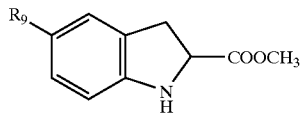
(74)

in which $R_9$ is as defined above, starting with compound (73), with magnesium in methanol, iii) formation of the corresponding amide (75) by reaction with the appropriate amine $R_5NH_2$

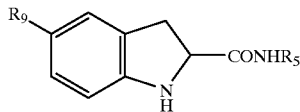
(75)

in which $R_5$ and $R_9$ are as defined above iv) reaction of compound (75) with a compound (IX)

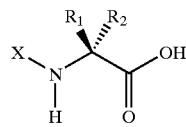
(IX)

in which $R_1$ and $R_2$ have the meanings given above and X represents a protecting group, in order to form compound (76)

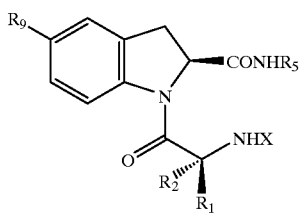
(76)

in which $R_1$, $R_2$, $R_5$, $R_9$ and X have the meanings given above, v) removal of the group X in order to form the desired compound (I).

Step iv) is advantageously carried out in the presence of bis(2-oxo-3-oxazolidinyl)phosphinyl chloride and ethylamine in methylene chloride.

In the compounds prepared according to this route 13, $R_1$ preferably represents an ethyl group and $R_5$ preferably represents an n-butyl group.

Lastly, the subject of the invention is a process (route 14) for the preparation of a compound of formula (I) given above, in which:

$R_1$ represents a linear or branched $C_1$–$C_4$ alkyl group;
$R_2$, R and R' each represent a hydrogen;
n=0 and m=1, and $R_3$ represents the unit

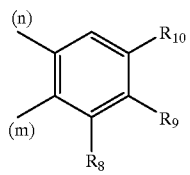

in which $R_8$, $R_9$ and $R_{10}$ each represent a hydrogen;
$R_4$ represents an amide group $CONHR_5$ in which $R_5$ is a $(CH_2)_3OH$ group, characterized in that it comprises:
i) reaction of the methyl ester of indoline-2S-carboxylic acid with a compound of formula (IX)

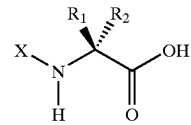
(IX)

in which $R_1$ and $R_2$ have the meaning given above and X represents a protecting group, in order to form compound (77) below

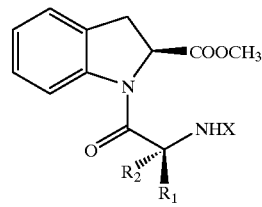
(77)

in which $R_1$, $R_2$ and X are as defined above ii) formation of amide (78)

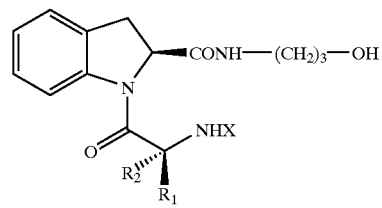
(78)

in which $R_1$ and $R_2$ have the above meaning starting with compound (77), by the action of 3-hydroxypropylamine in methanol iii) removal of the group X in order to form the desired compound (I).

The methyl ester of indoline-2S-carboxylic acid can be prepared from indoline-2S-carboxylic acid with methanol and concentrated sulphuric acid.

Step ii) is advantageously carried out in the presence of bis(2-oxo-3-oxazolidinyl)phosphinyl chloride and triethylamine in methylene chloride.

In the compounds prepared according to this route 14, $R_1$ preferably represents an ethyl group.

In all of the processes described above, formation of the acid anhydrides can be carried out by the standard methods, advantageously using isobutyl chloroformate in the presence of N-ethylmorpholine in tetrahydrofuran.

Moreover, according to the invention, X or X' represents a standard protecting group which is capable of protecting the desired function in a given molecule without affecting the other functions in that molecule, such as, in particular, the benzyl, benzyloxycarbonyl or tert-butoxycarbonyl groups. These groups are introduced by standard methods that are well known to those skilled in the art.

This is likewise the case for the deprotection steps, which are also carried out by methods known per se such as, in particular, acid hydrolysis or catalytic hydrogenation, in particular in the presence of Pd/C.

As regards the group Y, it is a radical capable of esterifying an acid function without modifying the other functions in the molecule, and constituting a good leaving group in order to be readily eliminated in a subsequent step. It is preferably the succinimide ester.

The Applicant's research has shown that the compounds of formula (I) have many therapeutic properties and in particular in the field of treating disorders or complaints which involve inactivation or excessive degradation (or which may be treated by delaying the physiological degradation) of endogenous neuropeptides, such as, in particular, disorders or complaints associated with inactivation of CCK.

Thus, the subject of the present invention is also the use of a compound of formula (I) as a drug for treating, in man or animals, in particular, eating, mood, cognitive or motor disorders, in particular anorexia, schizophrenia, Parkinson's disease and depression, as well as disorders of gastrointestinal transit such as irritable bowel syndrome, bulimia or pathological obesity conditions.

The subject of the present invention is also the use of a compound of formula (I) to prepare a drug intended for treating, in man or animals, complaints or disorders brought about by the physiological degradation of endogenous neuropeptides, in particular that of CCK.

The subject of the present invention is, in particular, the use of compounds of formula (I) to prepare a drug intended for treating disorders or complaints as mentioned above.

Compounds of the formula (I) which are useful as drugs may be administered in a physiologically acceptable vehicle.

Thus, the subject of the present invention is also pharmaceutical compositions comprising a therapeutically effective amount of a compound of formula (I) in combination with a physiologically acceptable vehicle.

The subject of the invention is also a process for treating, in man or animals, complaints or disorders associated with excessive degradation (or which may be treated by delaying the physiological degradation) of endogenous neuropeptides, in particular disorders or complaints associated with the inactivation of CCK, in particular the disorders given as examples above, comprising the administration of a pharmaceutical composition as defined above.

The subject of the present invention is also the use of the compounds of formula (I) as inactivation inhibitors for endogenous neuropeptides and in particular CCK.

The inventors have observed that, in general, among the compounds of formula (I), those having an L,L chirality (that is to say S,S according to the Ingold-Kahn-Prelog nomenclature) are the most active. In the examples given below, the configuration of the other optically active carbons is also indicated for the compounds of formula (I) having more than two asymmetric centres.

In all the abovementioned uses, it is preferred to choose compounds according to the invention that have a Ki constant less than or equal to 1 $\mu$M, such as those given as examples and, in an entirely preferable manner, the compounds of formula (I) having an indoline skeleton.

According to the invention, all the abovementioned uses also comprise that of the compounds of formula (I) which are already known, as indicated above, that is to say the compounds of formula (I) in which $R_2$, R and R' represent a hydrogen, n=0 and m=1 or n=1 and m=0, $R_3$ represents the —$(CH_2)_2$— divalent radical, $R_4$ represents an amide group $CONHR_5$, $R_1$ represents a $CH_2CH_3$, $(CH_2)_2CH_3$, $(CH_2)_3CH_3$, $CH(CH_3)_2$, $CH_2CH(CH_3)_2$ or $CH(CH_3)CH_2CH_3$ group with $R_5$ representing a hydrogen, $R_1$ represents $CH_2CH(CH_3)_2$ with $R_5$ representing a $CH_2CH_3$ group and $R_1$ represents $CH_3$ with $R_5$ representing the unit

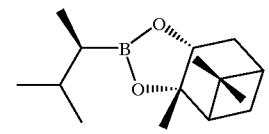

Other advantages and characteristics of the present invention will become apparent on reading the experimental results which follow, in particular of a method of isolation and characterization of the tripeptidylpeptidase according to the invention, as well as the preparation examples given by way of non-limiting illustration.

Isolation and Characterization of the CCK-inactivating Enzyme

The inventors used rat brain (cerebral cortex) membranes as starting material and non-sulphated CCK-8 (Asp-Tyr-Met-Gly-Trp-Met-Asp-Phe-NH$_2$) and CCK-5 (Gly-Trp-Met-Asp-Phe-NH$_2$) peptides as substrates, the characteristic products of the reaction (CCK-5 and Gly-Trp-Met) being measured fluorimetrically after isolation by high performance liquid chromatography (HPLC) according to Camus et al., (Neurosci., 1989, 29: 595).

The subsequent steps of HPLC purification used are described in Table I below, which also indicates the purification factors obtained using CCK-8 as substrate.

TABLE I

| Steps [eluent] | Retention time or molarity of the eluent at the peak of activity | Purification factor |
| --- | --- | --- |
| Membranes | | 1 |
| Solubilization of membranes (detergent: 1%) | | 0.4 |
| Ion exchange | 300 mM | 15 |

TABLE I-continued

| Steps [eluent] | Retention time or molarity of the eluent at the peak of activity | Purification factor |
|---|---|---|
| (DEAE 5PW) [NaCl 0–300 mM] | | |
| Hydroxyapatite (Bio-Gel HPHT) [phosphate 0–300 mM] | 220 mM | 45 |
| Gel filtration (Protein Pak 300SW) [phosphate 50 mM] | 45 min | 3.500 |
| Hydrophobic column (Phenyl-5 PW) [(NH$_4$)$_2$SO$_4$ 1M-O] | 0 | 8.571 |

From the second stage of purification onwards, the chromatography profile contains only one peak of enzymatic activity, on which is superimposed the peak obtained by measuring the hydrolysis of CCK-5, thereby indicating that only one enzyme is responsible for the two cleavages of the molecule CCK-8.

After the final step of purification, gel electrophoresis on sodium dodecyl sulphate (SDS) indicates a single band irreversibly labelled with $^3$H-DFP, at an apparent mass of 135 kDa.

Study of the specificity of the purified enzyme on a series of model substrates showed that it behaves like an aminotripeptidylpeptidase, capable, in particular, of hydrolysing Ala-Ala-Phe-p-nitroanilide or Ala-Ala-Phe-amidomethylcoumarin (A-AP-Amc) fragments, releasing nitroaniline or aminomethylcoumarin.

Preparation Examples for Compounds of Formula (I)

For the spectral data indicated in all the examples below, the abbreviations used have the following meanings:

s=singlet, m=multiplet, d=doublet, dd=doubled doublet, t=triplet, dt=doubled triplet, q=quartet, tq=triplet of quartets and tt=triplet of triplets.

EXAMPLE 1

Preparation of L-valyl-L-proline n-hexylamide; Route 1

$R_1$=CH(CH$_3$)$_2$; $R_2$=H; n=0 or 1 and m=0 or 1 with n being different from m; R=R'=H; $R_3$=—(CH$_2$)$_2$—; $R_4$=CO—NH—$R_5$; $R_5$=(CH$_2$)$_5$CH$_3$ a) Preparation of N-benzyloxycarbonyl-L-valine 10 g of L-valine (85 mmol) are dissolved in 4 M KOH (40 ml) and the mixture is cooled in ice. 21.9 g of benzyloxycarbonyl chloride (128 mmol) are added thereto over 5 minutes and a white solid forms. The mixture is stirred at 0° C. for one hour, the temperature is then allowed to rise and stirring is continued for another hour at room temperature. The reaction mixture is then diluted with 4 M KOH (200 ml) and is extracted with ether (2×100 ml). The aqueous phase is then brought to an acidic pH<1 with concentrated hydrochloric acid and is then extracted with ethyl acetate (3×200 ml). The extracts are combined and dried (Na$_2$SO$_4$) and the solvent is evaporated off. A clear oil is obtained.

$^1$H-NMR (200 MHz, CDCl$_3$, ppm): 7.42–7.52 (1H, d, NH); 7.24–7.36 (5H, m, Ph); 5.00 (2H, s, Ph—CH$_2$); 3.78–3.88 (1H, m, α-CH acid); 1.98–2.08 (1H, m, β-CH acid); 0.80–0.88 (6H, m, 2×CH$_3$).

b) Preparation of the succinimide ester of N-benzyloxycarbonyl-L-valine 15.63 g (62 mmol) of the product obtained in a) and 7.16 g of N-hydroxysuccinimide (62 mmol) are dissolved in dimethoxyethane (100 ml) and the mixture is cooled in ice. 12.8 g of dicyclohexylcarbodiimide (62 mmol) are added with stirring and the mixture is refrigerated overnight. The white solid formed is removed by filtration and the filtrate is concentrated in order to obtain a white solid by crystallization from isopropanol. The desired product is obtained: m.p.=105–6° C. (literature: 116–7° C.)

$^1$H-NMR: 7.35 (5H, s, ArCH); 5.27–5.41 (1H, d, NH); 5.11 (2h, s, PhCH$_2$); 4.58–4.71 (1H, m, α-CH valine); 2.80 (4H, s, 2×CH$_2$); 2.19–2.41 (1H, m, β-CH valine); 0.99–1.07 (6H, m, 2×CH$_3$).

c) Preparation of N-benzyloxycarbonyl-L-valyl-L-proline 3.4 g of L-proline (29.9 mmol) are dissolved in water (100 ml) and 4.5 g of triethylamine (44.8 mmol) are added. 10 g (29.9 mmol) of the product obtained in b) are dissolved in tetrahydrofuran (100 ml) and the solution is cooled with ice. The proline solution is added over 40 minutes and the mixture is stirred for one hour at 0° C. and then at room temperature overnight. The volume of solvent is reduced to about a half and the remaining solution is acidified (pH<1) with concentrated HCl and extracted with ethyl acetate (3×200 ml). The organic phases are combined and dried (Na$_2$SO$_4$) and the solvent is evaporated off. An oil is obtained.

TLC analysis (ethyl acetate/1% acetic acid) showed the presence of 4 components.

The product obtained is redissolved in ethyl acetate and extracted with 4M KOH (3×200 ml). The aqueous phases are acidified (pH<1) with concentrated HCl and are extracted with ethyl acetate (3×200 ml). The combined organic phases are dried (Na$_2$SO$_4$) and the solvent is evaporated off. An oil is obtained.

$^1$H-NMR (200 MHz, CDCl$_3$, ppm): 7.25–7.30 (5H, m, Ph); 5.90–5.95 (1H, d, NH); 5.04–5.10 (2H, m, PhCH$_2$); 4.50–4.57 (1H, m, α-CH valine); 4.26–4.34 (1H, m, α-CH proline); 3.63–3.79 (2H, m, CH$_2$ proline); 1.95–2.14 (4H, m, 2×CH$_2$ proline); 0.87–1.00 (6H, m, 2×CH$_3$).

Mass spectrum (EI): 349 (M$^+$+1).

d) Preparation of N-benzyloxycarbonyl-L-valyl-L-proline hexylamide 2 g (5.7 mmol) of the product obtained in c) are dissolved in tetrahydrofuran (50 ml, dry, distilled) and the solution is cooled in an ice/salt bath. 660 mg of N-ethylmorpholine (5.7 mmol) and 780 mg of isobutyl chloroformate (5.7 mmol) are added and the mixture is kept cool for 30 minutes. 580 mg of n-hexylamine (5.7 mmol) are added, the temperature of the mixture is allowed to rise to room temperature and the mixture is left like this overnight. The mixture is dissolved in water (50 ml) and extracted with ethyl acetate (2×50 ml). The organic phases are combined and dried (Na$_2$SO$_4$) and the solvent is evaporated off. 2.95 g of a brown oil are obtained. By crystallization from an ethyl acetate/petroleum ether mixture, 370 mg of a white powder are obtained. The filtrates are concentrated. By chromatography using ethyl acetate as eluent, the desired product is obtained.

$^1$H-NMR (200 MHz, CDCl$_3$, ppm): 7.33 (5H, s, Ph); 5.45–5.50 (1H, d, NH); 5.07–5.08 (2H, d, PhCH$_2$); 4.52–4.57 (1H, m, α-CH valine); 4.28–4.36 (1H, m, α-CH proline); 3.56–3.72 (2H, m, CH$_2$ proline); 3.11–3.21 (2H, m, α-CH$_2$ amide); 1.69–2.39 (5H, m, β-CH valine, 2×CH$_2$ proline); 1.15–1.45 (8H, m, 4×CH$_2$); 0.81–0.98 (9H, m, 3×CH$_3$).

e) Preparation of the title compound in the form of the oxalate 900 mg (208 mmol) of the product obtained in d) are dissolved in methanol (100 ml) and 300 mg of palladium-on-charcoal are added. The mixture is hydrogenated for 3 hours and the catalyst is then removed by filtration. After removal of the solvent, 602 mg (94.5%) of a pale oil are obtained.

TLC analysis showed that no more starting material remained.

182 mg of oxalic acid (202 mmol) in 5 ml of ethanol are added and the oil is dissolved. After addition of ether (50 ml), a cloudy solution is obtained, which is refrigerated. The desired product is obtained in the form of the oxalate salt.

m.p.=146–7° C.

Elemental analysis: $C_{16}H_{31}N_3O_2 \cdot C_2H_2O_4$

Found: C=55.99%; H=8.75%; N=10.63%;

Theory: C=55.80%; H=8.58%; N=10.84%;

$^1$H-NMR (200 MHz, DMSO, ppm): 7.85–7.91 (1H, t, NH); 4.25–4.32 (1H, q, α-H proline); 3.93–3.96 (1H, d, α-H valine); 3.43–3.72 (2H, m, $CH_2$ proline); 2.95–3.07 (2H, m, α-$CH_2$ amide); 1.66–2.15 (5H, m, β-CH valine, 2×$CH_2$ proline); 1.25–1.39 (8H, m, 4×$CH_2$); 0.8–1.2 (6H, m, 3×$CH_3$).

IR (cm$^{-1}$): 3400, 3333 (N—H), 2700–3200 (OH), 1683, 1639 (C=O), 1195 (CONH).

Mass spectrum (FAB): 298 (M$^+$+1).

EXAMPLE 2

Preparation of 1-(2(S)-amino-butyryl)-L-proline 3-(methylthio)propylamide; Route 1

$R_1=CH_2CH_3$; $R_2=H$; n=0 or 1 and m=0 or 1 with n being different from m; R=R'=H; $R_3=$—$(CH_2)_2$—; $R_4=$CO—NH—$R_5$; $R_5=(CH_2)_3SCH_3$;

a) Preparation of N-(tert-butoxycarbonyl)-2(S)-aminobutyric acid 8 g of 2(S)-aminobutyric acid (77.6 mmol) are dissolved in a mixture of dioxane (155 ml), water (78 ml) and 1N NaOH (78 ml). The solution is cooled in an ice/salt bath and 18.62 g of di-tert-butyl dicarbonate (85.4 mmol) are added. The solution is allowed to warm to room temperature and is stirred for one hour. The mixture is then concentrated under vacuum to a volume of about 90 ml and is then acidified with $KHSO_4$ solution. The resulting solution is extracted with methylene chloride (2×200 ml) and the combined extracts are dried and evaporated, which leads to an oil. By prolonged drying under vacuum, a waxy white solid is obtained. m.p.=65–66° C.

b) Preparation of the succinimide ester of N-(tert-butoxycarbonyl)-2(S)-aminobutyric acid 14.2 g of acid (70 mmol) obtained in a) are dissolved in dry tetrahydrofuran, under nitrogen at 0° C. 14.4 g of dicyclohexylcarbodiimide (70 mmol) and 8.1 g of N-hydroxysuccinimide (70 mmol) are added and the mixture is stirred overnight. The precipitate formed is removed by filtration and rinsed once with ethyl acetate, after which the solvent is removed under vacuum, which leads to an oil. The product is used in the subsequent steps without further purification.

$^1$H-NMR (CDCl$_3$, ppm): 4.6 (1H, m, α-H); 2.6 (4H, s, $CH_2CH_2$ succinimide); 1.5–1.7 (2H, m, $CH_2$ aminobutyryl); 1.2 (9H, s, (CH$_3$)$_3$); 0.9 (3H, t, CH$_3$ aminobutyryl)

c) Preparation of 1-(N-(tert-butoxycarbonyl)-2(S)-aminobutyryl)-L-proline 6.933 g of ester (23.1 mmol) obtained in b) are dissolved in tetrahydrofuran (150 ml) and the mixture is cooled to 0° C. A solution of 3.99 g of L-proline (34.7 mmol) and 3.51 g of triethylamine (34.7 mmol) in water (50 ml) is added. Stirring is maintained for 48 hours at room temperature. The tetrahydrofuran is removed under vacuum and is replaced by water, after which the pH is brought to about 2 with dilute $KHSO_4$. The acidic solution is extracted with methylene chloride and the extracts are dried and evaporated, which leads to an oil.

$^1$H-NMR (CDCl$_3$, ppm): 4.3 (1H, m, α-H); 4.2 (1H, m, α-H); 3.6–3.8 (2H, m, $CH_2$N proline); 1.9–2.1 (4H, m, $CH_2CH_2CH_2$N proline); 1.6–1.8 (2H, m, $CH_2$ aminobutyryl); 1.5 (9H, s, (CH$_3$)$_3$); 0.9 (3H, t, CH$_3$ aminobutyryl).

d) Preparation of 1-(N-(tert-butoxycarbonyl)-2(S)-aminobutyryl)-L-proline 3-(methylthio)propylamide 2.47 g (8.23 mmol) of the product obtained in c) are dissolved in tetrahydrofuran (100 ml), under nitrogen, while cooling in an ice/salt bath. 0.948 g of N-ethylmorpholine (8.23 mmol) are added, followed by 1.125 g of isobutyl chloroformate (8.23 mmol). After 30 minutes, 0.864 g of 3-(methylthio)propylamine (8.23 mmol) are added. Stirring is maintained overnight. The suspension is poured into methylene chloride (250 ml), washed with 10% citric acid (3×100 ml) and then with 5% NaHCO$_3$ (3×100 ml), dried and evaporated, which leads to an oil.

$^1$H-NMR (CDCl$_3$, ppm): 4.4 (1H, m, α-H); 4.3 (1H, m, α-H); 3.5–3.8 (2H, m, $CH_2$N proline); 3.2 (2H, m, $CH_2$N); 2.2 (2H, m, $CH_2CH_2$N proline); 2.0 (3H, s, CH$_3$S); 1.6–1.8 (8H, m, $CH_2CH_2CH_2$N proline, $CH_2CH_2SCH_3$, $CH_2$ aminobutyryl); 1.5 (9H, s, (CH$_3$)$_3$); 0.9 (3H, t, CH$_3$ aminobutyryl)

e) Preparation of the title compound in the form of the oxalate salt 5 g (12.9 mmol) of the product obtained in d) are dissolved in cooled trifluoroacetic acid (100 ml), with cooling in an ice/salt bath, and the mixture is stirred for 30 minutes. The acid is removed under vacuum, which leads to a clear oil. This oil is treated with 5% NaHCO$_3$ and is extracted with methylene chloride. The organic phase is dried and evaporated, which leads to the free base (clear oil). The oil obtained is dissolved in a small amount of ethanol and oxalic acid (1.1 equivalents) is added. After addition of ether, white crystals of the desired product in the form of the oxalate salt are obtained. This product is pure enough not to need recrystallization.

m.p.=120–121° C.

$^1$H-NMR (CD$_3$OD, ppm); 4.5 (1H, m, α-H); 4.3 (1H, m, α-H); 3.6 (2H, m, $CH_2$N proline); 2.5 (2H, m, $CH_2$N amide); 2.1 (3H, s, SCH$_3$); 1.75–2.0 (10H, m, $SCH_2CH_2CH_2CH_2CH_2$N proline, $CH_2$ aminobutyryl); 1.0 (3H, t, CH$_3$ aminobutyryl)

Elemental analysis: $C_{13}H_{25}N_3O_2S \cdot C_2H_2O_4 \cdot 0.5H_2O$

Found: C=47.17%; H=7.05%; N=10.67%;

Calculated: C=46.62%; H=7.30%; N=10.87%;

EXAMPLE 3

Preparation of 1-(2(S)-aminobutyryl)-L-proline n-pentylamide; Route 1

$R_1=CH_2CH_3$; $R_2=H$; n=0 or 1 and m=0 or 1 with n being different from m; R=R'=H; $R_3=$—$(CH_2)_2$—; $R_4=$CO—NH—$R_5$; $R_5=(CH_2)_4CH_3$ a) Preparation of N-benzyloxycarbonyl-2(S)-aminobutyric acid 10 g of 2(S)-aminobutyric acid (97 mmol) are dissolved in aqueous 4M KOH solution (100 ml) and the mixture is cooled to 0° C. 24.7 g of benzyl chloroformate (145 mmol) are added and the mixture is stirred while allowing its temperature to rise to room temperature over 2 hours 30 minutes. The mixture is then diluted with water (100 ml) and extracted with ether (2×200 ml). The aqueous phase is acidified to a pH<1 with concentrated HCl and is extracted with ethyl acetate (3×200 ml). The ethyl acetate fractions are combined and dried ($Na_2SO_4$) and the solvent is removed. A white solid is obtained.

$^1$H-NMR (ppm): 7.32 (5H, s, ArCH); 5.22–5.28 (1H, d, NH); 5.10 (2H, s, Ph—$CH_2$); 4.02–4.44 (1H, m, α-CH) ; 1.58–2.02 (2H, m, $CH_2$); 0.9–1.2 (3H, t, $CH_3$).

b) Preparation of the succinimide ester of N-benzyloxycarbonyl-2(S)-aminobutyric acid.

20 g of acid (84 mmol) obtained in a) and 9.7 g of N-hydroxysuccinimide (20 mmol) are dissolved in dimethoxyethane (160 ml) and the solution is cooled in ice. 17.3 g of dicyclohexylcarbodiimide (84 mmol) are added portionwise, with cooling, and a white precipitate forms rapidly. The mixture is refrigerated overnight, then filtered and the solvent is removed. A viscous oil is obtained. By crystallization from isopropanol, a white solid is obtained.

$^1$H-NMR (ppm): 7.31 (5H, s, ArCH); 5.3–5.6 (1H, d, NH); 5.1 (2H, s, Ph—$CH_2$); 4.8–4.9 (1H, m, α-CH); 2.9 (4H, s, 2×$CH_2$ ester); 1.80–2.05 (2H, m, $CH_2$ aminobutyryl); 0.95–1.25 (3H, m, $CH_3$aminobutyryl).

c) Preparation of 1-(N-benzyloxycarbonyl-2(S)-aminobutyryl)-L-proline 5 g of ester (14.95 mmol) obtained in b) are dissolved in tetrahydrofuran (50 ml) and the solution is cooled in ice. 1.75 g of L-proline (14.95 mmol), 2.25 g of triethylamine (22.4 mmol) and water (50 ml) are then added thereto. The mixture is stirred and is cooled for one hour and is then maintained at room temperature overnight. The solvent content is reduced to about half the volume and the solution is acidified and extracted with ethyl acetate (3×100 ml). The combined ethyl acetate fractions are dried ($Na_2SO_4$) and the solvent is removed. A thick oil is obtained.

1H-NMR (ppm): 7.38 (5H, s, ArCH); 5.9–6.0 (1H, d, NH); 5.08 (2H, s, Ph—$CH_2$); 4.42–4.54 (2H, m, 2×α-CH); 3.52–3.85 (2H, m, $CH_2$ proline); 1.52–2.30 (6H, m, 2×$CH_2$ proline, $CH_2$ aminobutyryl); 0.85–1.0 (3H, m, $CH_3$).

d) Preparation of 1-(N-benzyloxycarbonyl-2(S)-aminobutyryl)-L-proline n-pentylamide 2 g (5.98 mmol) of the product obtained in c) are dissolved in dry, distilled tetrahydrofuran (50 ml) and the solution is cooled in an ice/salt bath. 0.813 g of isobutyl chloroformate (5.98 mmol) and 0.687 g of N-ethylmorpholine (5.98 mmol) are added thereto with stirring and the solution becomes cloudy. Stirring is continued with cooling for 30 minutes, then 0.52 g of n-pentylamine (5.98 mmol) is added. The mixture is stirred at room temperature overnight and is then diluted with water (50 ml) and extracted with ethyl acetate (2×50 ml). The combined organic extracts are dried ($Na_2SO_4$) and the solvent is removed. 2.54 g of an oil are obtained. HPLC and TLC analysis showed that some starting acid remained. The oil obtained is thus redissolved in ethyl acetate (100 ml), washed with 4M KOH (50 ml) and water and then dried ($Na_2SO_4$) and the solvent removed. The desired product is obtained.

$^1$H-NMR (ppm): 7.33 (5H, s, ArCH); 5.07–5.08 (2H, m, $CH_2$Ph); 3.96–4.07 (2H, m, α-CH); 3.48–3.9 (2H, m, $CH_2$ proline); 1.1–2.5 (12H, m, 6×$CH_2$); 0.75–1.0 (6H, m, 2×$CH_3$).

e) Preparation of the title compound in the form of the oxalate 1 g (2.48 mmol) of the product obtained in d) is dissolved in methanol (100 ml) and 200 mg of Pd/C (10%) are added. This mixture is hydrogenated under pressure for 3 hours in Parr apparatus. The catalyst is removed by filtration, then the solvent is removed and 223 mg of oxalic acid (2.48 mmol) are added. By crystallization from an ethanol/ether mixture, the desired product is obtained.

m.p.=140–141° C.

Elemental analysis:

$C_{14}H_{27}N_3O_2.0.9C_2H_2O_4.0.2C_2H_5OH.0.5H_2O$

Found: C=52.63%; H=8.44%; N=11.24%;

Calculated: C=52.78%; H=8.48%; N=11.40%;

Mass spectrum (FAB): 270 ($M^+$+1)

$^1$H-NMR (DMSO-$d_6$, ppm): 7.64–7.69 (1H, m, NH); 4.24–4.30 (1H, m, α-CH); 4.03–4.09 (1H, m, α-CH); 3.30–3.74 (2H, m, $CH_2$ proline); 2.90–3.10 (—NH—$CH_2$—); 1.52–2.10 (6H, m, 2×$CH_2$ proline, $CH_2$ butyl chain); 0.72–1.44 (12H, m, 2×$CH_3$, 3×$CH_2$ pentyl chain).

EXAMPLE 4

Preparation of 1-(2(S)-amino-butyryl)-L-proline n-butylamide; Route 1

$R_1$=$CH_2CH_3$; $R_2$=H; n=0 or 1 and m=0 or 1 with n being different from m; R=R'=H; $R_3$=—$(CH_2)_2$—; $R_4$=CO—NH—$R_5$; $R_5$=$(CH_2)_3CH_3$ a) Preparation of 1-(N-(tert-butoxycarbonyl)-2(S)-aminobutyryl)-L-proline n-butylamide 2.42 g of 1-(N-(tert-butoxycarbonyl)-2(S)-aminobutyryl)-L-proline (8.05 mmol) prepared as in Example 2 c) are dissolved in dry tetrahydrofuran (15 ml). The solution is cooled in an ice/salt bath and 0.927 g of N-ethylmorpholine (8.05 mmol) and 1.10 g of isobutyl chloroformate (8.05 mmol) are then added. The solution is stirred for 45 minutes and 0.59 g (8.05 mmol) of n-butylamine is added. After stirring overnight, methylene chloride (200 ml) is added and the mixture is washed with 10% citric acid (2×100 ml) and then with 5% $NaHCO_3$ (2×100 ml). The organic phase is dried ($Na_2SO_4$) and evaporated under vacuum. A syrup is obtained. The deprotection is carried out without characterization.

b) Preparation of the title compound in the form of the oxalate

The product obtained in a) is treated with cold trifluoroacetic acid (TFA) (28 ml), with stirring, in an ice/salt bath for 30 minutes. The TFA is removed under vacuum. The resulting oil is treated with cold 5% $NaHCO_3$ until the pH is about 10, and is then extracted with methylene chloride. The organic phase is dried ($Na_2SO_4$) and evaporated. The oil is taken up in a small volume of ethanol and treated with oxalic acid. After addition of ether, white crystals of the desired product are obtained in the form of the oxalate salt. This compound is sufficiently pure without recrystallization.

m.p.=165–167° C.

$^1$H-NMR ($CD_3OD$, ppm): 4.4 (1H, m, α-H); 4.2 (1H, m, α-H); 3.4–3.7 (2H, m, $CH_2N$ proline); 3.0–3.2 (2H, m, $CH_2NC_4H_9$); 1.6–2.2 (4H, m, $NCH_2CH_2CH_2$ proline); 1.2–1.5 (4H, m, $CH_2$ aminobutyryl, $NCH_2CH_2C_4H_9$); 1.1 (3H, t, $CH_3$ aminobutyryl); 0.9 (3H, t, $CH_3$ of the n-butyl).

Elemental analysis: $C_{13}H_{25}N_3O_2.C_2H_2O_4.1.3H_2O$

Found: C=49.15%; H=7.62%; N=11.06%;

Theory: C=48.85%; H=8.09%; N=11.39%;

EXAMPLE 5

Preparation of 1-(2(S)-aminobutyryl)-L-proline [2 (S) methyl]butylamide; Route 1

$R_1=CH_2CH_3$; $R_2=H$; n=0 or 1 and m=0 or 1 with n being different from m; R=R'=H; $R_3=\text{—}(CH_2)_2\text{—}$; $R_4=CO\text{—}NH\text{—}R_5$; $R_5=(S)CH_2CH(CH_3)CH_2CH_3$;

a) Preparation of 1-(N-benzyloxycarbonyl-2(S)-aminobutyryl)-L-proline

A solution of 2.1395 g of L-proline (18.6 mmol) and 1.56 g of $NaHCO_3$ (18.6 mmol) in water (20 ml) is treated with a solution of 4.138 g of the succinimide ester of N-benzyloxycarbonyl-2(S)-aminobutyric acid (12.4 mmol) prepared as in Example 3 b), in dimethoxyethane (25 ml). After 5 hours, 12.4 ml of water are added, the resulting mixture is acidified to pH=2 with concentrated HCl and is extracted with ethyl acetate. The extracts are dried and are evaporated, which leads to a syrup.

$^1$H-NMR ($CDCl_3$, ppm): 7.2 (5H, m, H-aryl); 5.2 (1H, m, α-H); 5.0 (3H, m, $CH_2$ benzyloxycarbonyl, α-H); 4.0–4.1 (2H, m, $CH_2$N); 1.8–2.0 (4H, m, $CH_2CH_2CH_2$N); 1.1–1.2 (2H, m, $CH_2$ aminobutyryl); 0.9 (3H, t); 3.8 (2H, m, $CH_2$ aryl); 3.5 (2H, m, $CH_2$ ring); 3.2 (2H, m); 2.0 (2H, m); 0.9 (3H, t, $CH_3$ aminobutyryl).

b) Preparation of 1-(N-benzyloxycarbonyl-2(S)-aminobutyryl)-L-proline [2(S)-methyl]butylamide 3.8 g (11.4 mmol) of the product obtained in a) are dissolved in tetrahydrofuran (100 ml) and the mixture is cooled, under nitrogen, in an ice/salt bath. 1.31 g of N-ethylmorpholine (11.4 mmol) are added, followed by 1.487 g of isobutyl chloroformate (11.4 mmol). After 30 minutes, 0.99 g of 2(S)-methylbutylamide (11.4 mmol) are added and stirring is continued overnight. The suspension is poured into methylene chloride (250 ml), washed with 10% citric acid (3×100 ml) and then with 5% $NaHCO_3$ (3×100 ml), dried and evaporated. An oil is obtained.

$^1$H-NMR ($CDCl_3$, ppm): 7.2 (5H, m, H-aryl); 5.0 (2H, d, $CH_2$ benzyloxycarbonyl); 4.3–4.5 (2H, m, 2αH); 3.2–3.6 (2H, m, $CH_2$N); 2.9–3.1 (2H, m, $CH_2$N proline); 1.0–2.1 (18H, m, $CH_2CH_2CH_2$N, $CH_3CH_2$ aminobutyryl, $NCH_2CH(CH_3)CH_2CH_3$).

c) Preparation of the title compound in the form of the oxalate 1.96 g of the product obtained in b) are dissolved in methanol and 0.24 g of palladium-on-charcoal (10%, wet) is added. This suspension is hydrogenated in Parr apparatus at 40 psi for 4 hours. The catalyst is removed by filtration and the solvent is removed under vacuum. The resulting oil is dissolved in a small amount of ethanol and oxalic acid (1.1 equivalents) are added. After addition of ether, the desired product is obtained in the form of the oxalate salt.

m.p.=135–136° C.

$^1$H-NMR ($CD_3OD$, ppm): 4.4 (1H, m, α-H); 4.25 (1H, m, α-H); 3.65 (2H, m, $CH_2$N proline); 3.0 (2H, m, $CH_2$N amide); 2.0 (5H, m, $CH_2CH_2$N proline, $CH_3CH_2CH(CH_3)CH_2$N); 1.5 (2H, m, $CH_2$ aminobutyryl); 1.1 (3H, t, $CH_3$ aminobutyryl); 0.9 (6H, m, $CH_3CH_2CH(CH_3)CH_2$N).

Elemental analysis: $C_{14}H_{27}N_3O_2\cdot C_2H_2O_4\cdot 5H_2O$

Found: C=52.04%; H=7.82%; N=11.27%

Calculated: C=52.16%; H=8.21%; N=11.41%

EXAMPLE 6

Preparation of 1-(2(S)-amino-butyryl)-L-proline n-propylamide; Route 1

$R_1=CH_2CH_3$; $R_2=H$; n=0 or 1 and m=0 or 1 with n being different from m; R=R'=H; $R_3=\text{—}(CH_2)_2\text{—}$; $R_4=CO\text{—}NH\text{—}R_5$; $R_5=(CH_2)_2CH_3$ a) Preparation of 1-(N-(tert-butoxycarbonyl)-2(S)-aminobutyryl)-L-proline n-propylamide 2 g of 1-(N-(tert-butoxycarbonyl)-2(S)-amino-butyryl)-L-proline (6.6 mmol) prepared as in Example 2 c) are dissolved in tetrahydrofuran (40 ml). 0.86 ml of isobutyl chloroformate (6.6 mmol) and 0.85 ml of N.-ethylmorpholine (6.6 mmol) are then added to this solution, at –10° C. and under nitrogen. After stirring at –10° C. for 20 minutes, 2.75 ml of n-propylamine (33.0 mmol) are added. The mixture is left stirring at 0° C. for one hour and then at room temperature overnight. The solvent is evaporated off under vacuum and a white semi-solid material is obtained. It is dissolved in ethyl acetate (150 ml) and washed with 5% citric acid (30 ml), saturated sodium bicarbonate solution (30 ml) and brine (20 ml). After drying ($Na_2SO_4$) the mixture is filtered and the solvent is evaporated off. An oil is obtained, which is purified by liquid chromatography on a column (eluent: ethyl acetate) and a white solid is obtained.

$^1$H-NMR ($CDCl_3$, ppm): 6.86 (1H, broad s, NH); 5.22 (1H, d, NH); 4.56 (1H, dd, α-CH aminobutyryl); 4.37 (1H, m, α-CH proline); 3.54 (2H, m, N—$CH_2$ proline); 3.13 (2H, m, N—$CH_2$ propyl); 2.39–1.31 (8H, m, 4×$CH_2$); 1.24 (9H, s, $(CH_3)_3$—); 0.91 (3H, t, $CH_3$ propyl); 0.86 (3H, t, $CH_3$ aminobutyryl).

Mass spectrum (FAB): 342 (MH$^+$)

b) Preparation of the title compound in the form of the trifluoroacetate 2.0 g (5.9 mmol) of the product obtained in a) are dissolved in dichloromethane (5 ml) and trifluoroacetic acid (5 ml) is added to this cooled solution. The reaction mixture is stirred for 2 hours in an ice bath. The acid is evaporated off and, on precipitation with ethyl ether and drying overnight at 30° C. under 0.1 mmHg, the desired product is obtained.

m.p.=46–51° C. (open capillary)

$^1$H-NMR ($D_2O$/TSP, ppm): 4.41 (1H, t, α-CH aminobutyryl); 4.33 (1H, t, α-CH proline); 3.71 (2H, m, N—$CH_2$ proline); 3.17 (2H, dt, N—$CH_2$ amide); 2.21 (2H, dt, $CH_2$ proline); 1.86–2.03 (4H, m, 2×$CH_2$); 1.54 (2H, tq, $CH_2$ amide); 1.04 (3H, t, $CH_3$ aminobutyryl); 0.89 (3H, t, $CH_3$ amide).

Mass spectrum (FAB): 242 (MH$^+$)

Elemental analysis: $C_{12}H_{23}N_3O_2\cdot 1.3CF_3COOH$

Found: C=44.75%; H=6.13%; N=10.59%;

Calculated: C=45.01%; H=6.29%; N=10.79%;

EXAMPLE 7

Preparation of 1-(2(S)-amino-butyryl)-L-proline isobutylamide; Route 1

$R_1=CH_2CH_3$; $R_2=H$; n=0 or 1 and m=0 or 1 with n being different from m; $R_3=\text{—}(CH_2)_2\text{—}$; $R_4=CO\text{—}NH\text{—}R_5$; $R_5=CH_2CH(CH_3)_2$ a) Preparation of 1-(N-(tert-butoxycarbonyl)-2(S)-aminobutyryl)-L-proline isobutylamide The process is performed as in Example 6 a), using isobutylamine instead of n-propylamine. An oil is obtained.

$^1$H-NMR ($CDCl_3$, ppm): 6.93 (1H, broad s, NH); 5.24 (1H, broad s, NH); 4.56 (1H, dd, α-CH aminobutyryl); 4.36 (1H, tt, α-CH proline); 3.53 (2H, m, N—$CH_2$ proline); 3.53 (2H, m, N—$CH_2$ proline); 3.00 (2H, m, N$CH_2$); 2.39–1.58 (7H, m, CH and $CH_2$) ; 1.37 (9H, s, $(CH_3)_3$—); 0.94 (3H, t, $CH_3$); 0.84 (6H, d, 2×$CH_3$).

Mass spectrum (FAB): 356 (MH$^+$)

b) Preparation of the title compound in the form of the trifluoroacetate

The process is performed as in Example 6 b), starting with the product prepared in a), and the desired product is obtained by precipitation with ethyl ether and drying at room temperature under vacuum (0.1 mmHg) overnight.

m.p.=58–61° C. (open capillary)

$^1$H-NMR (D$_2$O/TSP, ppm): 4.43 (1H, t, α-CH aminobutyryl); 4.33 (1H, t, α-CH proline); 3.70 (2H, m, N—CH$_2$ proline); 3.04 (2H, dd, N—CH$_2$ amide); 2.23 (2H, m, CH$_2$ proline); 1.96 (4H, m, CH$_2$); 1.78 (1H, m, CH); 1.04 (3H, t, CH$_3$ aminobutyryl); 0.89 (6H, d, 2×CH$_3$).

Mass spectrum (FAB): 256 (MH$^+$)

IR (KBr disc, cm$^{-1}$): 3298 and 3089 (N—H), 2962 (C—H), 1662 (C=O).

Elemental analysis: C$_{13}$H$_{25}$N$_3$O$_2$.1.2CF$_3$COOH

Found: C=47.15%; H=6.75%; N=10.72%;

Calculated: C=47.16%; H=6.73%; N=10.71;

EXAMPLE 8

Preparation of L-valyl-L-proline n-butylamide; Route 2

R$_1$=CH(CH$_3$)$_2$; R$_2$=H; n=0 or 1 and m=0 or 1 with n being different from m; R=R'=H; R$_3$=—(CH$_2$)$_2$—; R$_4$=CO—NH—R$_5$; R$_5$=(CH$_2$)$_3$CH$_3$ a) Preparation of N-(tert-butoxycarbonyl)-L-proline n-butylamide 5.0 g of succinimide ester of N-(tert-butoxycarbonyl)-L-proline (0.016 mmol), marketed by Novabiochem, are dissolved in tetrahydrofuran (50 ml). 1.533 ml of n-butylamine (0.015 mmol) are then added thereto, at 0° C. over 10 minutes, and the mixture is stirred for one hour. The solvent is removed and the resulting crude material is purified by chromatography on silica, using ethyl acetate as eluent. An oil is obtained.

$^1$H-NMR (200 MHz, CDCl$_3$, ppm): 6.3 (1H, broad s, NH); 4.25 (1H, m, methine); 3.6–3.1 (4H, m, methylene); 2.9 (2H, m, methylene); 1.95 (9H, s, methyl); 1.6–1.2 (6H, m, methylene).

b) Preparation of L-proline n-butylamide trifluoroacetate 4.32 g of the product obtained in a) (0.014 mmol) and 15 ml of trifluoroacetic acid are stirred at room temperature for one hour. The excess acid is evaporated off under vacuum and the residue is dried under vacuum for 3 hours. The desired product is obtained.

$^1$H-NMR (400 MHz, CDCl$_3$, ppm): 9.3 (1H, broad s, NH); 7.65 (1H, broad s, NH); 4.7 (1H, m, methine); 3.5 (2H, m, methylene); 3.25 (2H, m, methylene); 2.1 (4H, m, methylene); 1.5 (2H, m, methylene); 1.3 (2H, m, methylene); 0.9 (3H, t, methyl).

c) Preparation of N-(tert-butoxycarbonyl)-L-valyl-L-proline n-butylamide 3.707 g of succinimide ester of N-(tert-butoxycarbonyl)-L-valine (0.0117 mol), marketed by Novabiochem, are dissolved in tetrahydrofuran (30 ml). A solution of 3.35 g of the product obtained in b) (0.0117 mol) in 20 ml of tetrahydrofuran is added with stirring at 25° C. 3.0 ml of triethylamine are then added in order to neutralize the trifluoroacetate salt and the mixture is stirred for 20 hours. The solvent is evaporated off and the resulting crude material is purified by chromatography on silica, using a 1/1 mixture of petroleum ether and ethyl acetate as eluent. The desired product is obtained in the form of a colourless oil.

$^1$H-NMR (200 MHz, CDCl$_3$, ppm): 6.9 (1H, broad s, NH); 5.2 (1H, d, NH); 4.5 (1H, dd, methine); 4.25 (1H, dd, methine); 3.6 (2H, m, methylene); 3.2 (2H, q, methylene); 1.1 (5H, m, methine and methylene); 1.4 (9H, s, CH$_3$ tert-butyl); 1.3 (4H, m, methylene); 0.9 (6H, dd, methyl); 0.8 (3H, t, methyl).

d) Preparation of L-valyl-L-proline n-butylamide trifluoroacetate 1.5 g of the product obtained in c) (4.8 mmol) and 6 ml of trifluoroacetic acid are stirred at 25° C. for 45 minutes. The excess acid is evaporated off and the resulting crude material is purified by chromatography on silica, using an ether/ethyl acetate/acetic acid mixture (1/1/0.1) and then an ethyl acetate/methanol/acetic acid mixture (1/1/0.1) as eluent. An additional purification is carried out by preparative HPLC under the following conditions: Lichrosorb r.p. select B column; eluent: 60/40 water/methanol +0.1% trifluoroacetic acid. The product is obtained in the form of an oil.

e) Preparation of the title compound in the form of the oxalate 1.7 g of the product obtained in d) (4.4 mmol) are dissolved in aqueous 20% Na$_2$CO$_3$ solution (5 ml) and the mixture is stirred for 10 minutes and extracted with ethyl acetate (3×15 ml). The organic extracts are dried (Na$_2$SO$_4$) and concentrated so as to obtain an oil (0.734 g). 1 g of oxalic acid is dissolved in 3 ml of ethanol and this solution is added to the oil obtained above, and the resulting mixture is heated on a water bath for 10 minutes and then cooled. By addition of ethyl ether, a white precipitate is obtained, which is filtered and washed with ethyl ether. It is recrystallized from a methanol/ethyl acetate/ether mixture (1/1/3), which leads to white crystals.

m.p.=165–166° C.

TLC (6/2/2 ethyl acetate/methanol/acetic acid): R$_f$=0.25

IR (KBr, cm$^{-1}$): 3432 (NH), 3072 ($^+$NH$_3$), 2958 (C—H), 1718 (C=O), 1641 (C=O), 1554 (N—H).

$^1$H-NMR (200 MHz, DMSO-d$_6$, ppm): 7.9 (1H, t, NH); 7.3 (2H, broad s, NH$_2$); 4.25 (1H, t, methine); 3.95 (1H, d, methine); 3.65 (1H, m, CH$_2$ proline); 3.45 (1H, m, CH$_2$ proline); 3.0 (2H, m, methylene); 2.2–1.5 (5H, m, methine and methylene); 1.3 (4H, m, methylene); 0.9 (6H, dd, methyl); 0.8 (3H, t, methyl).

Mass spectrum: 269 (M$^+$) (2%).

Elemental analysis: C$_{16}$H$_{29}$N$_3$O$_6$.0.25(COOH)$_2$

Found: C=52.12%; H=8.01%; N=11.07%;

Calculated: C=52.19%; H=7.85%; N=11.13%;

EXAMPLE 9

Preparation of L-alanyl-L-prolyl-L-borovaline pinanediol ester; Route 5

R$_1$=CH$_3$; R$_2$=H; n=0 or 1 and m=0 or 1 with n being different from m; R=R'=H; R$_3$=—(CH$_2$)$_2$—; R$_4$=CO—NH—R$_5$; R$_5$=

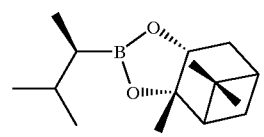

a) Preparation of isopropylboronic acid

A solution of 149 g of triethyl borate (1 mol) in 300 cm$^3$ of ether and a 2M solution of 103 g of isopropylmagnesium chloride (1 mol) in 500 cm³ of ether, are added simultaneously, under a nitrogen atmosphere and with vigorous stirring, into ethyl ether (500 cm³) stirred under nitrogen at −78° C., while maintaining the temperature below −70° C. for 2 hours. The temperature of the reaction mixture is allowed to rise to room temperature and stirring is continued for a further 24 hours. The mixture is then acidified with cold dilute 40% sulphuric acid (250 cm³) and is stirred. while maintaining the temperature below 15° C. Stirring is carried out for a further 16 hours and the mixture is diluted again with water (250 cm³) in order to remove the emulsion. The ether phase is separated out and the aqueous phase is extracted with ether (3×200 cm³). The ether phases are combined, dried (magnesium sulphate) and then concentrated. The resulting solid is crystallized from water. The desired product is obtained (wet); this product needs to be kept wet or in ether in order to prevent autoxidation.

$^1$H-NMR (DMSO-$d_6$), ppm): 3.4 (2H, broad s, OH); 0.8 (7H, s, methine and methyl).

[Isopropylboronic acid has been described by R. M. Washburn et al., Org. Syn., 1963, Coll. Vol. IV: 68–72].

b) Preparation of hexahydro-2(1-methylethyl)-3a,5,5-trimethyl-[3aS-(3aα,4α,6α,7aα)]-4,6-methano-1,3,2-benzodioxaborole (or isopropylboronic acid pinanediol ester): compound XV.

30 g of acid (0.34 mol) prepared in a) and 40 g of (+)-pinanediol (0.23 mol) in 150 cm³ of ether are stirred for 48 hours. The reaction mixture is diluted with 150 cm³ of ether and 100 cm³ of water and the ether phase is then separated out. The aqueous phase is extracted with ether (3×50 cm³), and the organic phases are combined, dried (magnesium sulphate) and concentrated. The resulting oil is purified by chromatography on silica, eluting with a petroleum ether/ethyl acetate mixture (9/1). The oil obtained is further purified by distillation under vacuum and the desired product, having a boiling point of 64–68° C. at 0.3 Torr, is collected.

$^1$H-NMR (CDCl$_3$, ppm): 4.25 (1H, dd, methine); 2.4–1.7 (6H, m, methylene and methine); 1.35 (3H, s, methyl); 1.25 (3H, s, methyl); 1.0 (7H, s, methyl and methine); 0.8 (3H, s, methyl).

[This compound has been described by C. A. Kettner et al., J. Biol. Chem., 1984, 259, 15106].

c) Preparation of 2-(1-chloro-2-methylpropyl)-hexahydro-3a,5,5-trimethyl-[3aS-[2(1S),3aα,4α,6α,7aα]-4,6-methano-1,3,2-benzodioxaborole: compound XVI.

200 cm³ of tetrahydrofuran and 10.6 g of dichloromethane (0.124 mol) are stirred at −105° C. under a nitrogen atmosphere. 46 cm³ of 1.6M butyllithium in hexane (0.084 mol) are introduced using a syringe, at −105° C. over 40 minutes. This mixture is stirred for 15 minutes, after which a mixture of 15 g of compound XV (0.0675 mol) obtained in b) in 60 cm³ of tetrahydrofuran is introduced slowly, using a syringe, while maintaining the temperature at −105° C. The reaction mixture is stirred for 30 minutes and then 40.5 cm³ of 1M zinc chloride in ethyl ether (0.0405 mol) are introduced at −105° C. over 20 minutes, using a syringe. The temperature is allowed to rise to room temperature and stirring is continued for a further 16 hours. The solvent is removed under reduced pressure and the resulting oil is taken up in 500 cm³ of ether. The ether extract is washed with saturated aqueous ammonium chloride solution (100 cm³) and the aqueous phase is separated out. It is extracted with ether (2×100 cm³) and the combined ether solutions are dried (magnesium sulphate) and concentrated. The resulting oil is distilled under vacuum and the desired compound XVI is obtained in the main fraction, this product having a boiling point of 74–108° C. at 0.2 Torr.

$^1$H-NMR (CDCl$_3$, ppm): 4.35 (1H, d, O—CH—pinanediol ester); 3.32 (1H, d, CHCl); 2.45–1.9 (7H, m, methylene-methine pinanediol ester); 1.35 (3H, s, methyl); 1.25 (3H, s, methyl); 1.0 (6H, dd, CH$_3$ isopropyl); 0.8 (3H, s, methyl).

d) Preparation of hexahydro-3a,5,5-trimethyl-α-(1-methylethyl)-N,N-bis(trimethylsilyl)-[3aS-[2(1R),3aα,4α,6α,7aα)]-4,6-methano-1,3,2-benzo-dioxaborole-2-methanamine: compound XVII 24.3 cm³ of hexamethyldisilazane (0.115 mol) and 120 cm³ of tetrahydrofuran are stirred at −72° C. under a nitrogen atmosphere. 61 cm³ of 1.6M n-butyl-lithium in hexane (0.0974 mol) are added gradually thereto, between −72° C. and −70° C., over 40 minutes. The temperature is allowed to rise to 0° C. over 3 hours and the reaction mixture is again cooled to −72° C. A mixture of 24 g of compound XVI (0.0886 mol) obtained in c), in 100 cm³ of tetrahydrofuran, is introduced slowly thereto over 30 minutes at −72° C. The temperature is then brought to 20° C. and the mixture is stirred for 20 hours and then concentrated. The resulting oil is treated with ether (250 cm³) and with water (100 cm³). The organic phase is separated out and the aqueous phase is extracted with ethyl ether (2×100 cm³), after which the ether solutions are combined, dried (sodium sulphate) and concentrated. The resulting oil is distilled under vacuum (discarding the forerun) and compound XVII is obtained, this product having a boiling point of 120–155° C. at 0.2 Torr.

$^1$H-NMR (CDCl$_3$, ppm): 4.25 (1H, d, O—CH pinanediol ester); 2.4–1.7 (7H, m, methylene and methine); 1.35 (3H, s, methyl); 1.25 (3H, s, methyl); 1.15 (1H, d, methine); 0.9 (6H, dd, CH$_3$ isopropyl); 0.8 (3H, s, methyl).

e) preparation of hexahydro-3a,5,5-trimethyl-α-(1-methylethyl) -[3aS-[2(1R),3aα,4α,6α,7aα]-4,6-methano-1,3,2-benzodioxaborole-2-methanamine trifluoroacetate (or borovaline pinanediol ester trifluoroacetate): compound XVIII 1 g (0.0258 mol) of the product obtained in d) in 10 cm³ of pentate is stirred at 0° C. under a nitrogen atmosphere. 0.584 cm³ of trifluoroacetic acid (0.0758 mol) is introduced slowly thereto and this mixture is stirred for one hour at 0° C. After concentration under reduced pressure and then suction at high vacuum for 48 hours, compound XVIII is obtained in the form of a white solid.

$^1$H-NMR (DMSO-$d_6$, ppm): 7.7 (2H, broad s, NH$_2$); 4.3 (1H, d, O—CH); 2.8 (1H, m, α-CH); 2.4–1.8 (7H, m, methine and methyl); 1.35 (3H, s, methyl); 1.25 (3H, s, methyl); 1.0 (6H, dd, methyl); 0.8 (3H, s, methyl).

$[\alpha]^D_{23}$ +25° (c 1.0, CHCl$_3$)

f) Preparation of N-(tert-butoxycarbonyl)-L-alanyl-L-proline: compound XIX 3 g of L-alanyl-L-proline in hydrate form (0.0147 mol) are dissolved in 30 cm³ of aqueous 0.5M NaOH and 30 cm³ of dioxane and the mixture is cooled to 0° C. with stirring. 3.53 g of di-tert-butyl dicarbonate (0.0162 mol) are introduced thereto at 0C, using a syringe. The reaction mixture is stirred at 0° C. for 30 minutes and then at 20° C for one hour. 30 cm³ of ethyl acetate are added and the mixture is cooled to 0° C. It is then treated with dilute aqueous KHSO$_4$ until pH=2 is reached, and a precipitate forms. This is filtered off, washed with ether and dried under vacuum. The desired product is obtained.

NMR (DMSO-$d_6$, ppm): 6.9 (1H, d, NH); 4.2 (2H, m, α-CH alanine and proline); 3.5 (2H, m, methylene); 2.1 (1H, m, CH$_2$ proline); 1.9 (3H, m, CH$_2$ proline); 1.3 (9H, s, methyl); 1.1 (3H, d, methyl).

[This compound has been described in particular by E. Wuensch et al., Int. J. Pept. Protein Res., 1988, 32, 368].

g) Preparation of N-(tert-butoxycarbonyl)-L-alanyl-L-prolyl-L-borovaline pinanediol ester: compound XX 3.17 g of the compound obtained in f) are dissolved in 30 cm$^3$ of stirred tetrahydrofuran under nitrogen, and the solution is cooled to −20° C. 2.27 g of N-ethylmorpholine (0.0190 mol) are introduced thereto at −20° C., followed by 1.59 g of isobutyl chloroformate (0.0116 mol), and a precipitate forms. The reaction mixture is stirred at −20° C. for 30 minutes, after which a mixture of 4.05 g of compound XVIII in the form of the trifluoroacetate (0.0110 mol) as obtained in e) in 20 cm$^3$ of tetrahydrofuran is introduced. The mixture is stirred at −20° C. for 30 minutes, after which it is allowed to warm to 20° C. and is maintained at this temperature for 30 minutes. 30 cm$^3$ of water are then added and the mixture is extracted with ethyl acetate (3×50 cm$^3$). The combined organic phases are dried and concentrated. The resulting oil is purified by chromatography on silica, eluting with a chloroform/methanol mixture (9/1). By drying the resulting oil under vacuum, the desired compound is obtained in the form of a white solid.

$^1$H-NMR (CDCl$_3$, ppm): 7.0 (1H, d, NH); 5.4 (1H, d, NH); 4.65 (1H, d, α-CH); 4.45 (1H, t, α-CH); 4.30 (1H, d, O—CH); 3.5 (2H, m, methine); 3.1 (1H, t, α-CH borovaline); 2.5–1.5 (11H, m, methine and methylene proline and pinane); 1.4 (9H, s, methyl and tert-butyl); 1.35 (3H, s, methyl); 1.3 (3H, dd, methyl alanine); 0.9 (6H, dd, methyl); 0.75 (3H, s, methyl).

h) Preparation of the title compound in the form of the trifluoroacetate 0.5 g of the compound obtained in g) (0.000962 mol) is dissolved in 2 cm$^3$ of dichloromethane and the mixture is cooled to 0° C. under nitrogen. 3.7 g of trifluoroacetic acid (0.0324 mol) are introduced therein, at 0° C. under nitrogen, and the mixture is stirred for 30 minutes. The excess acid is removed under reduced pressure and then under vacuum. The resulting oil is purified by preparative HPLC on a Kromasil column equipped with a 215 nm detector, eluting with a 3/7 aqueous 0.1% CF$_3$COOH/methanolic 0.1% CF$_3$COOH mixture and a colourless solid is obtained, this product having a retention time of 9.7 minutes.

m.p.=124–125° C.

IR (KBr, cm$^{-1}$): 3475 (NH$_2$), 1671 (C=O amide), 1614 (C=O amide).

$^1$H-NMR (CDCl$_3$, ppm): 7.9 (1H, s, NH); 4.5 (broad s, NH$_2$ and α-CH alanine); 4.2 (1H, d, B—O—H); 3.95 (1H, m, α-CH proline); 3.45 (2H, m, CH$_2$ proline); 2.4–1.6 (11H, m, methylene and methine); 1.4 (3H, d, CH$_3$ alanine); 1.3 (3H, s, methyl); 1.2 (4H, s, methyl and methine); 0.8 (6H, dd, methyl); 0.7 (3H, s, methyl).

Elemental analysis: C$_{22}$H$_{38}$BN$_3$O$_4$.2CF$_3$COOH

Found: C=47.8%; H=6.50%; N=6.31%;

Calculated: C=48.2%; H=6.23%; N=6.49%;

EXAMPLE 10

Preparation of L-alanyl-L-prolyldifluoro-L-borovaline borohydride; Route 6

R$_1$=CH$_3$; R$_2$=H; n=0 or 1 and m=0 or 1 with n being different from m; R=R'=H; R$_3$=—(CH$_2$)$_2$—; R$_4$=CO—NH—R$_5$; R$_5$=

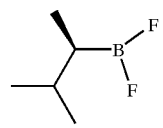

A solution of 0.20 g of 1M BCl$_3$ in CH$_2$Cl$_2$ (0.000384 mol) is cooled to −50° C. A solution of 0.20 g of the compound obtained in Example 9 (0.000384 mol) in 1 cm$^3$ of CH$_2$Cl$_2$ is added thereto using a syringe, under a nitrogen atmosphere and with stirring. This reaction mixture is stirred at this temperature for 15 minutes and the stirring is then continued at 0° C. for one hour. 1 cm$^3$ of water is added thereto, followed by 5 cm$^3$ of ethyl acetate. The aqueous phase is separated out and is evaporated to dryness at 20° C. The resulting white solid is dissolved in 2 cm$^3$ of water and 1 cm$^3$ of acetone and treated with aqueous 0.5M hydrofluoric acid (5 cm$^3$) for 15 minutes. The solvent is removed at 20° C. under a high vacuum. The residual solid is stirred in methanol and the insoluble residue is removed by filtration, after which the filtrate is evaporated off. A white solid is obtained which is crystallized from an acetone/water/ether mixture. The desired compound is obtained in the form of the borohydride.

m.p.=207–208° C.

IR (KBr, cm$^{-1}$): 3439 (NH), 3190 (NH$_3$), 1652 (C=O amide), 1629 (C=O amide), 727 (B—F).

$^1$H-NMR (D$_2$, ppm): 4.8 (1H, m α-CH proline); 4.5 (1H, m, α-CH alanine); 3.8 (2H, m, CH$_2$ proline); 2.31 (1H, m, α-CH valine); 2.0 (4H, m, CH$_2$ proline); 1.7 (1H, m, CH valine); 1.55 (3H, d, CH$_3$ alanine); 0.88 (6H, dd, methyl).

Elemental analysis: C$_{12}$H$_{22}$BF$_2$N$_3$O$_2$.0.95H$_3$BO$_3$

Found: C=41.51%; H=6.86%; N=11.72%;

Calculated: C=41.43%; H=7.20%; N=12.08%;

EXAMPLE 11

Preparation of 1-(2(S)-amino-butyryl)-(4(S)-fluoro)-L-proline n-butylamide; Route 3

R$_1$=CH$_2$CH$_3$; R$_2$=H; n=0 or 1 and m=0 or 1 with n being different from m; R=R'=H; R$_3$=—CH$_2$—CH(cis.F)—; R$_4$=CO—NH—R$_5$; R$_5$=n—C$_4$H$_9$;

a) Preparation of the methyl ester of N-benzyloxycarbonyl-4(S)-fluoro-L-proline 4.83 g (17.29 mmol) of methyl ester of N-benzyloxycarbonyl-4(R)-hydroxy-L-proline (marketed by Aldrich, Sigma) are dissolved, under nitrogen, in dichloromethane (90 ml) and this mixture is cooled to −70° C. and then treated dropwise with 3 ml (22.71 mmol) of diethylaminosulphur trifluoride (DAST). The resulting mixture is warmed up over one hour and is stirred for 18 hours. The reaction mixture is then poured into a water/ice mixture containing NaHCO$_3$ and extracted with dichloromethane, and the extract is dried (MgSO$_4$) and concentrated under reduced pressure. The yellow oil obtained is purified by chromatography on silica, eluting with a 40/60 and then 50/50 petroleum ether/ethyl acetate mixture. After evaporation under vacuum, an oil is obtained; R$_f$=0.5 (50/50 petroleum ether/ethyl acetate)

$^1$H-NMR (CDCl$_3$, ppm): 7.40–7.27 (5H, m, ArH); 5.22 (1H, dt, —CHF—, J$_{HF}$=52.4 Hz, J=3.7 Hz); 5.14–5.06 (2H, m, CH$_2$ benzyl); 4.58 (dd, α-H, J=30.1 Hz, J=9.5 Hz); 3.96–3.62 (2H, m, —CH$_2$N—); 3.64, 3.75 (3h, OCH$_3$); 2.59–2.47 (1H, m, —CH$_2$); 2.47–2.24 (1H, m, —CH$_2$—).

Mass spectrum (EI): m/e (% intensity)=281 (M$^+$, 1.36); 261 (M$^+$—HF, 0.01); 91 (Ph—CH$_2^+$, 100).

b) Preparation of N-benzyloxycarbonyl-4(S)-fluoro-L-proline 3.29 g (11.70 mmol) of the compound prepared in a) are dissolved in methanol (30 ml) and 7 ml (14 mmol) of 2M sodium hydroxide are added dropwise at −5° C. The mixture is then left at room temperature for 17 hours. After addition of water (100 ml), the methanol is removed under vacuum and the aqueous solution is washed twice with dichloromethane. This solution is then acidified to pH=3 with citric acid (20%) and is then extracted with dichloromethane (3×50 cm$^3$). The extracts are dried (MgSO$_4$) and filtered, and the solvent is removed under vacuum (adding ether at the end). A white solid is thus obtained.

m.p.=123–124° C.

$^1$H-NMR (400 MHz, CDCl$_3$, ppm): 7.38–7.26 (5H, m, ArH); 5.32–5.15 (3H, m, —CHF— J$_{HF}$=52.16 Hz, CH$_2$ benzyl); 4.61 (1H, dd, α-H J=27.6 Hz, J=9.6 Hz); 3.98–3.60 (2H, m, CH$_2$N); 2.78–2.54 (1H, m, —CH—); 2.52–2.24 (1H, m, —CH$_2$—).

TLC (ethyl acetate): R$_f$=0.04

Mass spectrum (EI): m/e (% intensity)=267 (M$^+$, 1.82); 247 (M$^+$—HF, 0.02); 91 (PhCH$_2^+$, 100).

c) Preparation of N-benzyloxycarbonyl-4(S)-fluoro-L-proline n-butylamide 1.40 g (5.24 mmol) of the compound obtained in b) are dissolved, under argon, in dry tetrahydrofuran (40 ml) and 0.66 ml (5.24 mmol) of 4-ethylmorpholine is added at 0° C., followed by 0.685 ml (5.24 mmol) of isobutyl chloroformate at −5° C. A white precipitate of 4-ethylmorpholine hydrochloride forms. After stirring for 20 minutes at −5° C., 0.54 ml (5.46 mmol) of n-butylamine is added and the reaction mixture is stirred for 40 minutes at 0° C. and then for one hour at room temperature. The solid is removed by filtration and washed with dry tetrahydrofuran, and the resulting solution is then evaporated under vacuum. The colourless residue is then treated with 50 ml of 5% citric acid solution and 120 ml of ethyl acetate. After shaking vigorously, the phases are separated and the organic phase is washed with 50 ml of 10% KHCO$_3$ and then with 50 ml of brine. After drying (MgSO$_4$) and removal of the solvent under vacuum, a white solid is obtained which is washed with petroleum ether and dried under vacuum over P$_2$O$_5$. The desired product is obtained in the form of a white solid.

m.p.=79–80° C.

TLC (50/50 ethyl acetate/petroleum ether): 0.5

$^1$H-NMR (400 MHz, CDCl$_3$, ppm): 7.34 (5H, broad s, ArH); 6.50–6.00 (1H, broad d, —NH—); 5.21 (1H, dt, —CHF— J$_{HF}$=51.9 Hz, J=3.4 Hz); 5.20–5.00 (2H, m, CH$_2$ benzyl); 4.48 (1H, d, α-H J=1.4 Hz); 4.02–3.38 (2H, m, —CH$_2$N proline); 3.32–3.02 (2H, m, —CH$_2$—NH— NH butyl); 2.90–2.52 (1H, m, —CH$_2$— proline); 2.48–2.08 (1H, m, —CH$_2$— proline); 1.54–1.16 (4H, m, —CH$_2$— NH butyl); 0.87 (3H, broad s, CH$_3$ NH butyl).

d) Preparation of 4(S)-fluoro-L-proline n-butylamide 1.48 g (4.59 mmol) of the compound obtained in c) are dissolved in 40 ml of methanol and 0.56 g of activated wet palladium-on-charcoal (10%) is added. The reaction mixture is hydrogenated under 60 psi for 3 hours and the solution is then filtered and concentrated under vacuum. An oil is obtained which crystallizes after drying under vacuum over P$_2$O$_5$ for 18 hours, which leads to the desired product.

m.p.=30° C.

$^1$H-NMR (400 MHz, CDCl$_3$, ppm): 7.53 (broad s, 1H, —NH—); 5.16 (1H, dt, —CHF—J$_1$=53.1 Hz, J$_2$ 3.7 Hz); 3.82 (1H, dd, α-H, J$_1$=10.3 Hz, J$_2$ =3.3 Hz); 3.40–3.10 (4H, m, —CH$_2$—N— and —CO—N—CH$_2$—); 2.48–2.20 (2H, m, —CH$_2$— proline); 2.12 (1H, broad s, —NH—); 1.42–1.52 (2H, m, —CH$_2$— NH butyl); 1.37–1.28 (2H, m, —C—H$_2$— NH butyl); 0.91 (3H, t, J=7.34 Hz, —CH$_3$).

e) Preparation of 1-(N-(tert-butoxycarbonyl)-2(S)-aminobutyryl)-(4(S)-fluoro)-L-proline n-butylamide The process is performed as in step c), starting with 0.81 g (3.98 mmol) of (N-(tert-butoxy-carbonyl)-2(S)-aminobutyric) acid prepared as in Example 2 a) and using the compound obtained in d) instead of n-butylamine. The crude product obtained shows two spots on TLC with similar R$_f$ values. These two products are separated by chromatography on silica gel, eluting with a gradient of from 20/80 to 60/40 of an ethyl acetate/petroleum ether mixture. The pure amide (second product) is obtained, which crystallizes after drying over P$_2$O$_5$ under vacuum for 5 days.

m.p.=67–68° C.

(trans isomer: T and cis isomer: C)

$^1$H-NMR (400 MHz, CDCl$_3$, ppm): 7.52 (0.37H, broad s, —NH— C); 6.55 (0.63H, broad s, —NH— T); 5.31 (0.37H, dt, —CHF— T J$_1$=52.3 Hz, J$_2$=4.0 Hz); 5.23 (0.63H, dt, —CHF— C J$_1$=50.1 Hz, J$_2$=3.2 Hz); 5.19 (0.63H, broad d, —NH— T, J=8.3 Hz); 5.19 (0.37H, broad d, —NH— C J=6.7 Hz); 4.76 (0.63H, d, αH T, J=Hz); 4.43 (0.37H, d, αH C, J=9.2 Hz); 4.33 (0.63H, q, αH T, J$_1$=8.5 Hz, J$_2$=6.7 Hz); 4.09–3.76 (2.37H, m, —CH$_2$—N— proline and αH C); 3.46–2.85 (3H, m, —CO—N—CH$_2$ and —CH$_2$ aminobutyryl); 2.34–2.07 (1H, m, —CH$_2$ aminobutyryl); 1.89–1.20 (15H, m, tert-C$_4$H$_9$ and —CH$_2$— proline and NH butyl); 1.00 (1.89H, t, CH$_3$ aminobutyryl T, J=7.3 Hz); 1.00 (1.11H, t, CH$_3$ aminobutyryl C, J=7.5 Hz); 0.89 (3H, t, CH$_3$ NH butyl, J=7.3 Hz).

Mass spectrum (FAB):

Found: MH$^+$=374 (11.7); 58 (100.0);

Calculated: M=373 f) Preparation of the title compound in the form of the trifluoroacetate

A 50/50 solution of CF$_3$COOH/CH$_2$Cl$_2$ is cooled to 0° C. and 0.20 g (0.547 mmol) of the compound prepared in e) is added thereto. The mixture is stirred at room temperature for 1 hour 15 minutes, after which the acid and the solvent are removed under vacuum, which leads to a yellow oil. 2×6 ml of CH$_2$Cl$_2$ are then added and the mixture is evaporated under vacuum in order to remove the excess acid. The resulting crude product is washed with 3×20 ml of anhydrous diethyl ether and a pure white solid is obtained, which is dried for 48 hours at room temperature under 0.25 mmHg. The desired product is obtained.

m.p.=60–63° C.

(T: trans isomer and C: cis isomer)

$^1$H-NMR (400 MHz, CD$_3$OD, ppm): 5.34 (0.73H, dm, —CHF— T); 5.27 (0.27H, dm, —CHF— C); 4.65 (1H, dd, α-H aminobutyryl); 4.13 (0.73H, dd, α-H proline T); 4.05–3.63 (2H, m, CH$_2$—N proline and 0.27H, α-H proline C); 3.28–3.08 (2H, m, —N—CH$_2$— —NH butyl); 2.68–2.25 (2H, m, —CH$_2$ aminobutyryl); 2.10–1.75 (2H, m, —CH$_2$ proline); 1.54–1.42 (2H, m, —CH$_2$—CH$_2$—CH$_3$); 1.40–1.29 (2H, m, —CH$_2$—CH$_2$—CH$_3$); 1.11 (2.19H, t, CH$_3$ aminobutyryl T); 1.01 (0.81H, t, CH$_3$ aminobutyryl C); 0.94 (0.81H, t, CH$_3$ NH butyl C); 0.92 (2.19H, t, CH$_3$ NH butyl T).

Mass spectrum (FAB): MH$^+$ found=274 (100%);

Calculated:=273

IR (KBr disc, cm$^{-1}$): 3438 (m, amide); 3073 (m, NH$_3^+$); 1668 (S, C=O).

Microanalysis: C$_{13}$H$_{24}$O$_2$N$_3$F.1.1CF$_3$COOH

Found: C=45.90%; H=6.30%; N=10.48%

Calculated: C=45.78%; H=6.34%; N=10.54%;

EXAMPLE 12

Preparation of 1-(2(S)-aminobutyryl)-(4(S)-benzyl)-L-proline n-butylamide; Route 4

R$_1$=CH$_2$CH$_3$; R$_2$=H; n=0 or 1 and m=0 or 1 with n being different from m; R=R'=H; R$_3$=—CH$_2$—CH(CH$_2$Ph)—; R$_4$=CO—NH—R$_5$; R$_5$=n—C$_4$H$_9$;

a) Preparation of the methyl ester of N-benzyloxycarbonyl-4-keto-L-proline 5.0 g (17.90 mmol) of the methyl ester of N-benzyloxycarbonyl-4-hydroxy-L-proline (marketed by Aldrich, Sigma) are dissolved in 300 ml of acetone. This solution is stirred magnetically and 15 ml of chromic acid in approximately 8N sulphuric acid are added over a period of about 3 minutes. Stirring is continued for one hour, after which the excess oxidizing agent is destroyed by adding 5 ml of isopropanol over 20 minutes. The solvent is removed and the residue is then dissolved in ether and filtered through fluorisil in order to remove the chromium salts. The crude product obtained after evaporation is purified by flash chromatography on silica, eluting with a gradient of from 15/85 to 40/60 of an ethyl acetate/petroleum ether (b.p. <40° C.) mixture. A colourless oil is obtained after drying under reduced pressure overnight.

R$_f$=0.85 (ethyl acetate)

$^1$H-NMR (200 MHz, CDCl$_3$, ppm): 7.30 (5H, broad s, ArH); 5.20–5.00 (2H, m, CH$_2$ benzyl); 4.85 (1H, t, α-H); 3.95 (2H, broad s, —CH$_2$—N proline); 3.70–3.60 (3H, d, —OCH$_3$); 3.05–2.80 (1H, m, —CH$_2$ proline); 3.65–3.50 (1H, m, CH$_2$ proline).

Mass spectrum (FAB): m/e (% intensity)=300 ((M +Na)$^+$, 100.0); 278 (MH$^+$, 13.0); 154 (43.5); 136 (12); 107 (12.5); 91 (100).

b) Preparation of the methyl ester of N-benzyloxycarbonyl-4-benzylidene-L-proline 3.68 g (9.46 mmol) of benzyltriphenyl-phosphonium chloride are suspended in 30 ml of dry tetrahydrofuran and this mixture is added to a solution of 0.22 g (9.65 mmol) of sodium hydride (95%) in 20 ml of dry tetrahydrofuran, under nitrogen. 25 ml of dry DMSO are then added and the mixture is heated at 70° C. until it becomes homogeneous (4 hours). After cooling the solution to 50° C., a mixture of 2.00 g (7.90 mmol) of the ester obtained in a) in 10 ml of dry tetrahydrofuran is added over 5 minutes. The reaction mixture is then heated at 70° C. for 16 hours, after which it is poured into 200 ml of water/ice containing 1.4 g of KHCO$_3$. 150 ml of dichloromethane are then added, after which the organic phase is separated out and the aqueous phase is extracted once with 100 ml of dichloromethane. After drying (MgSO$_4$) of the organic phases and evaporation under vacuum, the crude product obtained is purified by flash chromatography on silica, eluting with a 15/85 and then 35/65 ethyl acetate/petroleum ether mixture. After drying under vacuum under P$_2$O$_5$ overnight, a colourless oil is obtained.

R$_f$=0.90 (ethyl acetate)

$^1$H-NMR (400 MHz, CDCl$_3$, ppm): 7.50–7.05 (10H, m, ArH); 6.53–6.13 (1H, m, H vinyl); 5.30–5.00 (2H, m, H benzyl); 4.73–4.30 (3H, m, α-H and N—CH$_2$ proline); 3.80–3.50 (3H, dd, OCH$_3$); 3.33–3.10 (1H, m, —CH$_2$ proline); 3.05–2.67 (1H, m, —CH$_2$ proline);

Mass spectrum (FAB, (MNOBA matrix+NaI): m/e (% intensity)=300 (MH$^+$+Na, 97); 278 (MH$^+$, 13); 154 (44); 91 (C$_7$H$_7^+$, 100).

c) Preparation of the methyl ester of 4(S) benzyl-L-proline 0.95 g of activated palladium-on-charcoal (10% wet) is added to a solution of 2.10 g (5.97 mmol) of the ester obtained in b) in 250 ml of methanol and this reaction mixture is hydrogenated for 2 hours 30 minutes under 60 psi. After filtration of the solution, concentration under vacuum and drying over P$_2$O$_5$ overnight, the desired product is obtained.

The NMR spectrum shows the presence of two diastereoisomers in a 90/10 cis/trans ratio.

(T=trans isomer and C=cis isomer)

$^1$H-NMR (400 MHz, ppm): 7.32–7.12 (5H, m, ArH); 3.82 (1H, t, α-H, J=8.0 Hz); 3.74 (3H, s, OCH$_3$); 3.08–3.02 (1H, m, —CH$_2$—N proline); 2.80–2.73 (1H, m, —CH$_2$N proline); 2.72–2.58 (2H, m, H benzyl); 1.60–1.70 (0.1H, m, PhCH$_2$CH T); 1.50–1.59 (0.9H, m, PhCH$_2$CH C).

d) Preparation of the methyl ester of 1-(N-benzyloxycarbonyl-2(S)-aminobutyryl)-(4(S)-benzyl)-L-proline 0.66 g (4.01 mmol) of 3-hydroxy-1,2,3-benzo-triazine-4 (3H)-one and 0.83 g (4.01 mmol) of dicyclohexylcarbodiimide (DCC) are added, at 0° C., to a solution of 0.815 g (3.43 mmol) of N-benzyloxycarbonyl-2(S)-aminobutyric acid prepared as in Example 3 a) in a mixture of 5 ml of dimethylformamide and 5 ml of methylene chloride. After 1 hour 15 minutes, a mixture of 0.88 g (4.01 mmol) of the ester obtained in c) in 5 ml of CH$_2$Cl$_2$ is added. The mixture is stirred at 0° C. for 15 minutes and then for 2 days at room temperature. After removal of the solvent under vacuum, the residue is taken up in ethyl acetate. The dicyclohexylurea is removed by filtration and the filtrate is subsequently washed with 4% NaHCO$_3$, with 10% citric acid and then evaporated under vacuum. The crude product thus obtained is purified by flash chromatography on silica, eluting with a gradient of from 15/85 to 35/65 of an ethyl acetate/petroleum ether mixture. After evaporation, a yellow paste is obtained.

$^1$H-NMR (200 MHz, CDCl$_3$, ppm): 7.50–6.95 (10H, m, ArH); 5.60 (1H, d, —NH—); 5.05 (2H, m, PhCH$_2$O); 4.50–4.35 (2H, m, α-H); 3.95–3.60 (4H, m, OCH$_3$ and —CH$_2$—N proline); 3.35–3.20 (1H, m, —CH$_2$—N proline); 2.80–2.10 (4H, m, PhCH$_2$C and —CH$_2$ proline); 1.95–1.50 (3H, m, —CH$_2$ aminobutyryl and H proline); 0.95 (3H, t, CH$_3$ aminobutyryl).

R$_f$=0.61 (ethyl acetate)

e) Preparation of 1-(N-benzyloxycarbonyl-2(S)-aminobutyryl)-(4(S)-benzyl)-L-proline 1.30 g (2.96 mmol) of the ester obtained in d) are saponified with 1.75 ml (3.50 mmol) of 2M NaOH in 30 ml of methanol for 20 hours at room temperature. After evaporation under vacuum, the residue is taken up in 100 ml of distilled water, washed twice with ether and then acidified to pH=1 with 5N aqueous HCl and extracted three times with 150 ml of ethyl ether, and the organic phases are dried (MgSO$_4$), filtered and evaporated under vacuum. The desired product is obtained in the form of a white solid.

m.p.=56–57° C.

1H-NMR (200 MHz, CDCl$_3$, ppm): 7.5–7.0 (10H, m, ArH); 5.7 (1H, d, —NH—); 5.05 (2H, broad s, PhCH$_2$O);

4.50–4.25 (2H, m, α-H); 4.00–3.80 (1H, m, —N—CH$_2$ proline); 3.30–3.10 (1H, m, —N—CH$_2$ proline); 2.80–2.10 (4H, m, PhCH$_2$C and —CH$_2$ proline); 1.90–1.40 (3H, m, —CH$_2$ aminobutyryl and H proline); 0.90 (3H, t, CH$_3$ aminobutyryl).

f) Preparation of 1-(N-benzyloxycarbonyl-2(S)-aminobutyryl)-(4(S)-benzyl)-L-proline n-butylamide The process is performed as in Example 11 c), starting with the compound obtained above in c). The resulting crude product is purified by flash chromatography on silica, eluting with a gradient of from 15/85 to 50/50 of ethyl acetate/petroleum ether mixture. Two samples of the desired product are obtained.

g) Preparation of the title compound in the form of the oxalate hydrate

A solution of 0.75 g of the compound obtained above in f), in methanol, is hydrogenated under 60 psi for 2 hours 30 minutes, using 0.30 g of 10% palladium-on-charcoal (wet). After removal of the catalyst by filtration and of the solvent under vacuum, the crude product obtained is purified by flash chromatography, using a 50/50 ethyl acetate/petroleum ether mixture and then a 50/50 ethyl acetate/methanol mixture. After evaporation of the solvent, the resulting oil is taken up in isopropanol and filtered in order to remove the silica. 350 mg (1.01 mmol) of free base are obtained. 0.12 g (1.32 mmol) of oxalic acid in ethanol is added thereto and ether is added. After crystallization, the desired product is obtained.

m.p.=89–93° C. (open capillary)

$^1$H-NMR (400 MHz, CD$_3$OD, ppm): 7.32–7.15 (5H, m, ArH); 4.48–4.28 (1H, m, α-H); 4.22–4.10 (1H, m, α-H); 3.87–3.68 (1H, m, —CH$_2$—N proline); 3.42–3.06 (3H, m, —CH$_2$N proline and —CH$_2$—N NH$_2$ butyl); 2.84–2.44 (3H, m, —CH$_2$Ph and CH$_2$ proline); 2.36–2.10 (1H, m, —CH$_2$ proline); 2.02–1.76 (2H, m, —CH$_2$ aminobutyryl); 1.67–1.26 (5H, m, —CH$_2$CH$_2$ NH$_2$ butyl and H proline); 1.12–0.86 (6H, m, —CH$_3$ aminobutyryl and —CH$_3$ NH$_2$ butyl).

Microanalysis: C$_{20}$H$_{31}$N$_3$O$_2$.1.05(COOH)$_2$.0.9H$_2$O
Found: C=58.19%; H=7.24%; N=8.95%
Calculated: C=58.18%; H=7.71%; N=9.21%;

Mass spectrum (FAB): m/e (% intensity)=368 (M$^+$+Na, 14); 346 (M$^+$, 100); 261 (68); 160 "(47); 91 (C$_7$H$_7$$^+$, 7).

EXAMPLE 13

Preparation of 2-(2(S)-amino-butyryl)-1,2,3,4-tetrahydro-3(S)-isoquinolinecarboxylic Acid n-butylamide; Route 3

R$_1$=CH$_2$CH$_3$; R$_2$=H; n=0 and m=1; R=R'=H; R$_3$=

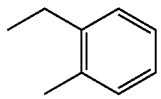

R$_4$=CO—NH—R$_5$; R$_5$=n-C$_4$H$_9$ a) Preparation of 1,2,3,4-tetrahydro-3(S)-isoquinolinecarboxylic acid 5.0 g (30.27 mmol) of L-phenylalanine are dissolved in 50 ml of concentrated hydrochloric acid and 4.0 g of paraformaldehyde and 1 ml of concentrated sulphuric acid are added. This solution is maintained at reflux for two days. After cooling and filtration, the resulting solid is dissolved in a 1/1 (v/v) hot water/ethanol mixture and aqueous NH$_4$OH (30%) is added until a pH 7.0 is reached. The crystals which have precipitated after cooling the solution are recovered by filtration, washed with ethanol and dried. The desired product is thus obtained.

m.p.=315° C. (lit.)[23]

Mass spectrum (FAB): m/e (% intensity)=178 (MH$^+$, 23); 154 (100).

b) Preparation of N-benzyloxycarbonyl-1,2,3,4-tetrahydro-3(S)-isoquinolinecarboxylic acid A solution of 2.50 g (14.11 mmol) of the acid prepared in a), in 2N NaOH (8 ml), is cooled in an ice/water bath and is stirred vigorously using a magnetic stirrer. 2.21 ml (15.52 mmol) of benzyl chloroformate and 8 ml of 2N NaOH are added alternately, in about 10 portions. The temperature of the reaction mixture is maintained between 0 and 5° C. by controlling the rate of addition of the reactants. 9 ml of 2N NaOH are added and the mixture is maintained at room temperature for 30 minutes. The alkaline solution is washed with ether (4×50 ml) and then acidified by addition of 5n HCl (pH<2). The mixture is then extracted with methylene chloride, dried over MgSO$_4$, filtered and evaporated under vacuum. After drying the resulting solid over P$_2$O$_5$, the desired product is obtained.

m.p.=52–55° C.

$^1$H-NMR (200 MHz, CDCl$_3$, ppm): 7.55–7.00 (9H, m, ArH); 5.10 (2H, d, H benylic); 5.00–4.50 (3H, m, α-H and —CH$_2$—N tetrahydroisoquinoline); 3.20–3.00 (2H, m, —CH$_2$ tetrahydroisoquinoline).

Mass spectrum (FAB): m/e (% intensity)=334 ((M +Na)$^+$, 0.1); 312 (MH$^+$, 3.5); 91 (C$_7$H$_7$$^+$, 100).

c) Preparation of N-benzyloxycarbonyl-1,2,3,4-tetrahydro-3(S)-isoquinolinecarboxylic acid n-butylamide The process is performed as in Example 11 c), starting with the acid obtained in b). The reaction mixture is stirred at 0° C. for 40 minutes and then at room temperature overnight. 100 ml of methylene chloride are then added and the solution is washed with 3×50 ml of 15% citric acid. After shaking vigorously, the phases are separated and the organic phase is then washed with 2×50 ml of 5% NaHCO$_3$. After drying over MgSO$_4$, the crude product obtained is purified by flash chromatography, eluting with a 70/30 (v/v) ethyl acetate/petroleum ether mixture. After evaporation under vacuum, the resulting product is dried over P$_2$O$_5$ overnight. The pure amide is thus obtained in the form of an oil.

$^1$H-NMR (200 MHz, CDCl$_3$, ppm): 7.45–7.05 (9H, m, ArH); 5.80 (1H, d, —NH—); 5.25–2.06 (2H, m, —CH$_2$—Ph); 4.90–4.40 (3H, m, α-H and —NH—CH$_2$ tetrahydroisoquinoline); 3.42–2.78 (4H, m, —NH—CH$_2$ NH$_2$ butyl and —CH$_2$ tetrahydroisoquinoline); 3.60–3.40 (2H, m, —CH$_2$ tetrahydroisoquinoline); 1.18–0.66 (7H, m, —CH$_2$CH$_2$CH$_3$ NH butyl).

R$_f$ (ethyl acetate)=0.60

Mass spectrum (FAB): m/e (% intensity)=367 (MH$^+$, 13.9); 91 (C$_6$H$_5$$^+$, 100).

d) Preparation of 1,2,3,4-tetrahydro-3(S)-isoquinolinecarboxylic acid n-butylamide The compound obtained in c) is hydrogenated under the conditions of Example 11 d). The desired product is obtained.

m.p.=58–60° C.

$^1$H-NMR (400 MHz, CDCl$_3$, ppm): 7.26–7.02 (5H, m, Ar—H and —NH amide); 4.08–3.98 (2H, m, α-H and —CH$_2$N tetrahydroisoquinoline); 3.51–3.58 (1H, m, —$CH_2$—NH tetrahydroisoquinoline); 3.32–3.20 (3H, m, —$CH_2$ amide and 1H —$CH_2$ tetrahydroisoquinoline); 2.76–2.88 (1H, m, —$CH_2$ tetrahydroisoquinoline); 1.81 (1H, broad s, —NH tetrahydroisoquinoline); 1.55–1.46 (2H, m, —NH—$CH_2$—$CH_2$—$CH_2$—$CH_3$); (2H, m, —NH—$CH_2$—$CH_2$—$CH_2$—$CH_3$); 0.93 (3H, t, $CH_3$ amide J=7.3 Hz).

e) Preparation of 2-(-N-benzyloxycarbonyl-2(S)-aminobutyryl)-1,2,3,4-tetrahydro-3(S)-isoquinolinecarboxylic acid n-butylamide The process is performed as in step c), starting with N-benzyloxycarbonyl-2(S)-aminobutyric acid prepared as in Example 3 a) and starting with the compound obtained in d). The reaction mixture is left to stand overnight at room temperature and 40 ml of methylene chloride are then added and this solution is washed with 3×50 ml of 10% citric acid. After shaking vigorously, the phases are separated and the organic phase is washed with 2×50 ml of 5% $NaHCO_3$. After drying over $MgSO_4$ and evaporation under vacuum, the resulting crude product is purified by flash chromatography on silica, eluting with a 15/85 and then 35/65 ethyl acetate/ether mixture. The desired product is obtained in the form of an oil which is dried under vacuum over $P_2O_5$ overnight.

Mass spectrum (FAB): m/e (% intensity)=474 ((M +Na)$^+$, 0.1); 452 (M$^+$, 2.5); 91 ($C_7H_7^+$, 100).

$^1$H-NMR (400 MHz, $CDCl_3$, ppm): 7.42–7.08 (9H, m, Ar—H); 6.03 (1H, broad s, —NH amide); 5.68 and 5.39 (1H, d, —NH amide); 5.20–4.88 (3H, m, H benzyl and α-H); 4.86–4.38 (3H, m, —$CH_2$N tetrahydroisoquinoline and α-H); 3.68–2.90 (4H, m, —$CH_2$N $NH_2$ butyl and —$CH_2$ tetrahydroisoquinoline); 2.00–1.60 (2H, m, —$CH_2$ aminobutyryl); 1.44–1.16 (2H, m, —$CH_2$—$CH_2$—$CH_2$—$CH_3$); 1.16–0.96 (2H, m, —$CH_2$—$CH_2$—$CH_2$—$CH_3$); 0.86 and 0.78 (3H, t, $CH_3$ aminobutyryl).

f) Preparation of the title compound in the form of the oxalate

The compound obtained in e) is hydrogenated under the conditions of step d). 0.16 g (1.78 mmol) of oxalic acid is then added to the filter solution and this solution is concentrated under vacuum. Ethanol is then added, followed by ether (1/50 ratio), which leads to a crystallized product. After filtration and washing with diethyl ether, the solid is dried over $P_2O_5$ under vacuum at 30° C. for 24 hours and the desired compound is obtained.

m.p.=105–110° C. (open capillary)

$^1$H-NMR (400 MHz, $CD_3OD$, ppm): 7.34–7.15 (4H, m, Ar—H); 4.86–4.54 (4H, m, 2 α-H and —$CH_2$N tetrahydroisoquinoline); 3.43–2.88 (4H, m, -$CH_2$ tetrahydroisoquinoline and —NH—$CH_2$ NH butyl); 2.14–1.80 (2H, m, —$CH_2$ aminobutyryl); 1.48–1.18 (4H, m, —$CH_2$—$CH_2$—NH butyl); 1.0–1.2 (3H, t, $CH_3$ aminobutyryl); 0.7–0.95 (3H, t, $CH_3$—NH butyl).

Mass spectrum (FAB): m/e (% intensity)=318 (MH$^+$, 96.1); 245 (30.9); 233 (40.3); 149 (100.0); 132 (65.4); 71 (38.8); 58 (53.7); 57 (73.0).

IR (KBr disc, cm$^{-1}$): 3072 (m, NH) ; 2956 (s, CH); 1652 (s, C=O).

Microanalysis: $C_{18}H_{27}N_3O_2 \cdot 1.05(COOH)_2 \cdot 0.5H_2O$

Found: C=57.63%; H=7.08%; N=9.53%;

Calculated: C=57.35%; H=7.21%; N=9.98%;

EXAMPLE 14

Preparation of 1-(2(S)-aminobutyryl)-2(S)-indolinecarboxylic Acid n-butylamide; Route 3

$R_1=CH_2CH_3$; $R_2=H$; n=0 and m=1; $R_3=$

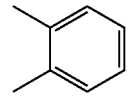

($R_6=H$), R=R'=H;
$R_4=CO—NH—R_5$; $R_5=n-C_4H_9$ a) Preparation of N-benzyloxycarbonyl-2(S)-indolinecarboxylic acid n-butylamide 7.699 g (25.9 mmol) of N-benzyloxycarbonyl-2(S)-indolinecarboxylic acid prepared as in Example 16 a) are dissolved in tetrahydrofuran (150 ml), under nitrogen. 2.986 g (25.9 mmol) of N-ethylmorpholine are added, at 0° C., followed by 3.54 g (25.9 mmol) of isobutyl chloroformate. After 45 minutes, 1.903 g (25.9 mmol) of n-butylamine are added and the suspension is stirred overnight. Methylene chloride (300 ml) is added and the organic phase is washed with 10% citric acid (3×100 ml) and then $NaHCO_3$ (3×100 ml). After drying and evaporation, a white solid is obtained which is recrystallized from methanol.

m.p.=164–165° C.

$^1$H-NMR ($CDCl_3$, ppm): 6.9–7.8 (9H, m, Ar—H); 5.2 (2H, m, $CH_2$ benzyloxycarbonyl); 4.9 (1H, m, aH); 2.9–3.8 (4H, m, $CH_2$ ring $CH_2$N); 1.0–1.5 (4H, M, $CH_2CH_2CH_2$N); 0.8–1.0 (3H, m, $CH_3$).

b) Preparation of 2(S)-indolinecarboxylic acid n-butylamide

The compound prepared in a) is dissolved in methanol and palladium-on-charcoal (10%, wet, 10% by weight) is added. The mixture is hydrogenated for 4 hours under 40 psi in Parr apparatus. After removal of the catalyst and evaporation of the methanol, crystals are obtained which are sufficiently pure without recrystallization.

m.p.=110–111° C.

$^1$H-NMR ($CDCl_3$, ppm): 6.8–7.1 (4H, m, Ar—H); 4.3 (1H, m, α-H); 2.9–3.5 (4H, m, $CH_2$ ring $CH_2$N); 1.0–1.9 (4H, m, $CH_2CH_2CH_2$N); 0.9 (3H, t, $CH_3$).

c) Preparation of 1-(N-benzyloxycarbonyl-2(S)-aminobutyryl)-2(S)-indolinecarboxylic acid n-butylamide The process is performed as in Example 15 c), using 0.646 g (2.73 mmol) of N-benzyloxycarbonyl-2(S)-aminobutyric acid prepared as in Example 3 a) and 0.595 g (2.73 mmol) of the amide prepared in step b). An oil is obtained which is recrystallized from $CCl_4$.

m.p.=178–179° C.

$^1$H-NMR ($CDCl_3$, ppm): 7.0–7.2 (9H, m, Ar—H); 4.9–5.3 (4H, m, 2×αH $CH_2$ benzyloxycarbonyl); 3.5 (2H, m, $CH_2$ ring); 3.1 (2H, m, $CH_2$N); 1.0–2.0 (9H, m, $CH_2CH_2CH_2$N $CH_2$ aminobutyryl $CH_3$ aminobutyryl); 0.9 (3H, m, $CH_3$ butyl).

d) Preparation of the title compound in the form of the oxalate hydrate

The compound obtained in c) is hydrogenated as in Example 5 c) for N-benzyloxycarbonyl-2(S)-aminobutyryl-L-proline [2(S)-methyl] n-butylamide and the title compound is isolated in the form of the oxalate salt. It is sufficiently pure without recrystallization.

m.p.=142° C.

¹H-NMR (CD₃OD, ppm): 8.25 (1H, m, NH); 7.25 (4H, m, Ar—H); 5.1 (2H, m, 2×αH (hidden by the solvent)); 3.8 (2H, m, CH₂Ar); 3.5 (2H, m, CH₂ ring); 3.2 (2H, m, CH₂N); 2.0. (2H, m, CH₂ aminobutyryl); 0.9–1.8 (10H, m, CH₃ aminobutyryl CH₃CH₂CH₂CH₂N).

Analysis: $C_{17}H_{25}N_3O_2 \cdot C_2H_2O_4 \cdot 0.75 H_2O$
Found: C=56.25%; H=6.99%; N=9.84%;
Calculated: C=56.08%; H=7.06%; N=10.33%;

EXAMPLE 15

Preparation. of 1-(2(S)-aminobutyryl)-2(S)-indolinecarboxylic Acid n-propylamide; Route 3

$R_1=CH_2CH_3$; $R_2=H$; n=0 and m=1; $R_3=$

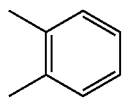

($R_6=H$); R=R'=H; $R_4=CO-NH-R_5$; $R_5=n-C_3H_7$;

a) Preparation of N-benzyloxycarbonyl-2(S)-indolinecarboxylic acid n-propylamide The process is performed as in Example 14 a), starting with N-benzyloxycarbonyl-2(S)-indolinecarboxylic acid prepared as in Example 16 a) and n-propylamine. A white solid is obtained, which is recrystallized from CCl₄.

m.p.=185–186° C.

¹H-NMR (CDCl₃, ppm): 7.0–7.25 (9H, m, Ar—CH); 5.20 (2H, s, Ph—CH₂); 4.90 (1H, m, NCHCO); 3.90 (2H, m, CH₂ indoline); 3.0–3.5 (NCH₂ propyl); 0.9–1.8 (5H, m, CH₃CH₂).

b) Preparation of 2(S)-indolinecarboxylic acid n-propylamide

The compound obtained in step a) is hydrogenated under the conditions of its n-butylamide analogue in Example 14 b). After evaporation of the methanol, a white solid is obtained, which is sufficiently pure without recrystallization.

¹H-NMR (CDCl₃, ppm): 6.85–7.2 (4H, ArCH); 4.3 (1H, m, NCHCO); 2.9–3.8 (4H, m, NCH₂, CH₂ indoline); 1.5 (2H, m, NCH₂CH₂); 0.9 (3H, t, CH₃).

c) Preparation of 1-(N-benzyloxycarbonyl-2(S)-aminobutyryl)-2(S)-indolinecarboxylic acid n-propylamide 0.439 g (1.85 mmol) of N-benzyloxycarbonyl-2(S)-aminobutyric acid prepared as in Example 3 a) is dissolved, under nitrogen, in tetrahydrofuran (50 ml) and the solution is cooled in an ice/water bath. 0.213 g (1.85 mmol) of N-ethylmorpholine is added, followed by 0.253 g (1.85 mmol) of isobutyl chloroformate. After 45 minutes, 0.378 g (1.85 mmol) of the compound obtained in step b) is added and stirring is continued for 12 hours. The suspension is poured into CH₂Cl₂ (100 ml) and the mixture is washed with 10% citric acid (3×100 ml) and then with 5% NaHCO₃ (3×100 ml). After drying and evaporation, a white solid is obtained which crystallizes from CCl₄.

m.p.=176–177° C.

¹H-NMR (CDCl₃, ppm: 7.0–7.25 (9H, m, H—Ar); 5.0 (2H, s, CH₂ benzyloxycarbonyl); 4.8 (1H, m, aH); 4.1 (1H, αH); 3.3 (2H, m, CH₂ ring); 3.0 (2H, m, CH₂N); 1.0–2.0 (4H, m, CH₃CH₂CH₂N CH₂ aminobutyryl); 0.70–1.00 (CH₃ aminobutyryl CH₃ propyl).

d) Preparation of the title compound in the form of the oxalate hydrate

The compound obtained in step c) is hydrogenated under the conditions of Example 5 c) for N-benzyloxycarbonyl-2 (S)-aminobutyryl-L-proline [2(S)-methyl)] n-butylamide. The desired product is obtained in the form of its oxalate salt, which is sufficiently pure without recrystallization.

m.p.=130–131° C.

¹H-NMR (CD₃OD, ppm): 7.70 (1H, m, NH); 6.55–6.90 (4H, m, H—Ar); 4.20–4.60 (2H, m, 2×αH); 2.90–3.40 (2H, m, CH₂ ring); 2.50–2.80 (CH₂N); 1.40–1.80 (2H, m, CH₂CH₃ propyl); 1.00 (2H, m, CH₂ aminobutyryl); 0.40–0.70 (6H, m, CH₃ aminobutyryl CH₃ propyl).

Microanalysis: $C_{16}H_{23}N_3O_2 \cdot (COOH)_2 \cdot 1.25H_2O$
Found: C=53.84%; H=6.68%; N=10.62%;
Calculated: C=53.79%; H=6.90%; N=10.45%;

EXAMPLE 16

Preparation of 1-(2(S)-aminobutyryl)-2(S)-indolinecarboxylic Acid methylamide; Route 3

$R_1=CH_2CH_3$; $R_2=H$; n=0 and m=1; R=R'=H;

$R_3=$ 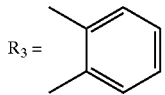

($R_6=H$); $R_4=CO-NH-R_5$; $R_5=CH_3$;

a) Preparation of N-benzyloxycarbonyl-2(S)-indolinecarboxylic acid

A solution of 20 g (122.56 mmol) of 2(S)-indolinecarboxylic acid in 2N NaOH (62 ml) is cooled in an ice/water bath and the solution is stirred using a powerful magnetic stirrer. 20.0 ml (140.09 mmol) of benzyl chloroformate and 68 ml of 2N NaOH are added thereto alternately in about 10 portions over 60 minutes. The temperature of the reaction mixture is maintained between 0° and 5° C. by controlling the rate of addition of the reactants. 50 ml of NaOH are then added and the mixture is maintained at room temperature for 30 minutes. The alkaline solution is washed with ether (4×150 ml) and is then acidified by addition of 5N HCl (80 ml, pH<2). A crystalline mass precipitates after leaving overnight at room temperature. It is filtered off and washed with distilled water (500 ml). After drying over P₂O₅, the desired product is obtained.

m.p.=117–118° C.

¹H-NMR (400 MHz, CDCl₃, ppm): 8.30–6.90 (10H, m, ArH and COOH); 5.45–5.14 (2H, m, CH₂—Ph); 5.08–4.92 (1H, m, αH); 3.65–3.46 (1H, m, CH₂ indoline); 3.30–3.15 (1H, m, CH₂ indoline).

Mass spectrum (FAB): m/e (% intensity)=342 ((M-H+ 2Na)⁺, 0.2); 320 ((M+Na)⁺, 4.3); 298 (MH⁺, 5.7); 297 (M⁺, 9.3); 91 ($C_7H_7^+$, 100).

b) Preparation of N-benzyloxycarbonyl-2(S)-indolinecarboxylic acid methylamide 4.00 g (13.45 mmol) of acid obtained in a) are dissolved in 90 ml of dry tetrahydrofuran and 1.71 ml (13.45 mmol) of 4-ethylmorpholine are added at 0° C. This solution is cooled to −5° C. and 0.62 ml (4.78 mmol) of isobutyl chloroformate is added dropwise. After 30 minutes at −5°C., the solution is saturated with methylamine (gas). The mixture is left overnight at room temperature and 150 ml of dichloromethane are then added and this solution is washed with 3×150 ml of 10% citric acid. After shaking vigorously, the phases are separated and the organic phase is washed with 2×150 ml of 5% NaHCO₃. After drying over MgSO₄, the crude product is purified by washing with hot CCl₄. A white solid corresponding to the pure amide is obtained.

m.p.=210–211° C.

1H-NMR (400 MHz, CDCl₃, ppm): 7.75 (1H, broad s, COOH); 7.45–6.95 (9H, m, Ar—H); 5.90 (1H, broad s, NH); 5.37–5.10 (2H, m, CH₂—Ph); 4.93 (1H, dd, α-H); 3.62–3.16 (2H, m, CH₂ indoline); 2.71 (3H, s, CH₃).

Mass spectrum (FAB): m/e (% intensity): 311 (MH⁺, 11.3); 310 (M⁺, 11.4); 91 (C₇H₇⁺, 100).

c) Preparation of N-benzyloxycarbonyl-2(S)-indolinecarboxylic acid methylamide

A solution of 2.91 g (9.38 mmol) of the compound obtained in step b) in 120 ml of methanol is hydrogenated at 60 psi for 3 hours in the presence of 1.20 g of activated 10% palladium-on-charcoal (wet). After filtration and concentration under vacuum, the resulting oil crystallizes after drying overnight over P₂O₅.

m.p.=125–130° C.

¹H-NMR (200 MHz, CDCl₃, ppm): 7.22–7.03 (3H, m, NH amide and 2 ArH); 6.82 (1H, t, J=7.4 Hz, ArH); 6.73 (1H, d, J=7.8 Hz, ArH); 4.42 (1H, t, αH J=9.4 Hz); 4.14 (1H, broad s, NH); 3.65–3.55 (1H, m, CH₂); 3.14–3.02 (1H, m, CH₂); 2.84 (3H, d, J=15.0 Hz, CH₃).

Mass spectrum (FAB): m/e=177 (MH⁺, 42.4); 176 (M⁺, 33.2); 118 (100.0).

d) Preparation of 1-(N-benzyloxycarbonyl-2(S)-aminobutyryl)-2(S)-indolinecarboxylic acid methylamide 1.73 g (8.51 mmol) of N-(tert-butoxycarbonyl)-2(S)-aminobutyric acid prepared according to Example 2 a) are dissolved, under argon, in 40 ml of dry tetrahydrofuran and 1.07 ml (8.51 mmol) of 4-ethylmorpholine are added at 0° C., followed by 1.11 ml (8.51 mmol) of isobutyl chloroformate at −5° C. A white precipitate forms. After stirring for 30 minutes at −5° C., 1.50 g (8.51 mmol) of the compound obtained in step c) are added. The mixture is then stirred at 0° C. for 40 minutes and then overnight at room temperature. 100 ml of dichloromethane are then added to this solution, after which it is washed with 3×50 ml of 10% citric acid. After shaking vigorously, the phases are separated and the organic phase is washed with 2×50 ml of 5% NaHCO₃. After drying over MgSO₄, the solvent is removed under vacuum and the crude product obtained is purified by recrystallization from CCl₄.

m.p.=196–197° C.

¹H-NMR (400 MHz, CDCl₃, ppm): 8.12 (1H, d, NH); 7.45–6.95 (9H, m, ArH); 5.30 (1H, d, NH); 5.25–5.0 (2H, m, CH₂Ph); 4.82 (1H, t, αH); 4.14 (1H, m, αH); 3.60–3.45 (2H, m, CH₂ indoline); 2.80 (3H, d, CH₃ methylamide); 2.0–1.55 (2H, m, CH₂ aminobutyryl); 1.03 (1H, t, CH₃ aminobutyryl).

Mass spectrum (FAB): m/e (% intensity)=396 (MH⁺, 9.9); 91 (C₆H₅⁺, 100).

e) Preparation of the title compound in the form of the oxalate hydrate 2.15 g (5.44 mmol) of the compound obtained in step d) are dissolved in 200 ml of methanol and 0.85 g of activated 10% palladium-on-charcoal (wet) is added. The reaction mixture is hydrogenated at 60 psi for 3 hours. The solution is filtered and 1.3 equivalents (0.64 g) of oxalic acid (7.07 mmol) are added and the solution is then concentrated under vacuum. Ethanol is added, followed by ether (1:50 ratio) and a crystallized product is obtained. After filtration and washing with diethyl ether, the solid is dried under vacuum for 24 hours over P₂O₅ at 35° C. The desired product is obtained.

m.p.=138–139° C.

¹H-NMR (400 MHz, CD₃OD, ppm): 8.20 and 8.02 (1H, d, ArH); 7.36–7.05 (3H, m, ArH); 5.18–5.02 and 4.70–4.62 (1H, m, αH indoline); 5.01–4.94 and 4.28–4.22 (1H, m, αH aminobutyryl); 3.92–3.00 (2H, m, CH₂ indoline); 2.78 and 2.73 and 2.33 (3H, s, CH₃ amide); 2.26–2.12 and 2.12–2.86 (2H, m, CH₂ aminobutyryl); 1.16 and 1.07 and 1.04 (3H, t, CH₃ aminobutyryl).

Mass spectrum (FAB): m/e (% intensity): 262 (MH⁺, 43.0); 154 (100); 137 (65.1); 136 (81.6).

IR spectrum (KBr disc, cm⁻¹): 3440 (wave, NH); 3289 (m, NH); 2969 (m, CH); 2935 (m, CH); 1668 (s, C=O).

Microanalysis: C₁₄H₁₉N₃O₂. (COOH)₂.1.25H₂O
Found: C=51.55%; H=6.05%; N=11.28%;
Calculated: C=51.40%; H=6.34%; N=11.24%;

EXAMPLE 17

Preparation of 1-(2(S)-aminobutyryl)-2(s)-indolinecarboxylic Acid ethylamide; Route 3

R₁=CH₂CH₃; R₂=H; n=0 and m=1;

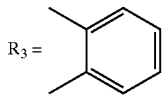

(R₆=H); R=R' H; R₄=CO—NH—R₅; R₅=CH₂CH₃;

a) Preparation of N-benzyloxycarbonyl-2(S)-indolinecarboxylic acid ethylamide

The process is performed as in Example 16 b), using ethylamine (gas). The crude product obtained is purified by recrystallization from CCl₄. By filtration, the pure amide is obtained in the form of a white solid.

m.p.=201.0–201.5° C.

R_f=0.58 (ethyl acetate)

¹H-NMR (400 MHz, CDCl₃, ppm): 7.70 (1H, broad s, COOH); 7.45–6.98 (9H, m, ArH); 5.90 (1H, broad s, NH); 5.35–5.18 (2H, m, CH₂ benzyl); 4.90 (1H, dd, αH); 3.64–3.04 (4H, m, CH₂ indolinyl and NH—CH₂); 0.99 (3H, broad s, CH₃).

b) Preparation of 2(S)-indolinecarboxylic acid ethylamide

The process is performed as in Example 16 c), starting with the compound obtained in step a). The resulting oil crystallizes after drying over P₂O₅ overnight. The desired product is obtained.

m.p.=92–95° C.

R_f=0.28 (ethyl acetate)

¹H-NMR (400 MHz, ppm): 7.22–7.00 (3H, m, NH amide and ArH); 6.82 (1H, t, ArH); 6.73 (1H, d, ArH); 4.42 (1H, t, αH); 4.14 (1H, broad s, NH); 3.65–3.50 (1H, m, CH₂ indoline); 3.45–3.20 (2H, m, CH₂CH₃); 3.14–3.02 (1H, m, CH₂ indoline); 1.15 (3H, t, CH₃).

c) Preparation of 1-(N-benzyloxycarbonyl-2(S)-aminobutyryl)-2(S)-indolinecarboxylic acid ethylamide The process is performed as in Example 16 d), using N-benzyloxycarbonyl-2(S)-aminobutyric acid prepared in Example 3 a) and the compound from step b). The pure amide is obtained in the form of a white solid.

m.p.=184.5–185° C.

¹H-NMR (400 MHz, CDCl₃, ppm): 8.15 (1H, d, H aromatic J=7.9 Hz); 7.44–7.08 (8H, m, ArH); 7.04 (broad s, NH amide); 5.37 (1H, d, NH amide); 5.0–5.2 (2H, m, PhCH₂); 4.84 (1H, m, αH); 4.18 (1H, m, αH); 3.62–3.48 (2H, m, CH₂ indoline); 3.34–3.14 (2H, m, CH₂ ethylamide); 2.10–1.60 (2H, m, CH₂ aminobutyryl); 1.20–0.98 (3H, m, CH₃).

d) Preparation of the title compound

The process is performed as in Example 16 c) for the compound obtained from step c). After drying the solid over $P_2O_5$ for 24 hours at 35° C., the desired product is obtained.

m.p.=115–120° C.

$^1$H-NMR (400 MHz, $D_2O$, ppm): 7.06–8.08 (4H, m, ArCH); 5.12 (1H, m, αH); 3.91 (1H, m, αH); 3.78–3.50 (1H, m, $CH_2N$ indoline); 3.25–2.96 (3H, m, $CH_2N$ indoline and NH—$CH_2$); 2.25–1.90 (2H, m, $CH_2$ aminobutyryl); 1.28–0.98 (m, $CH_3$ aminobutyryl and $CH_3$ ethylamide).

Mass spectrum (FAB): m/e (% intensity): 276 ($MH^+$, 49.9); 191 (80.8); 118 (100); 89 (16.0); 77 (37.2); 58 (74.1); 51 (21.3); 50 (22.7); 46 (19.9); 39 (28.2); 31 (29.5).

IR spectrum (KBr disc, $cm^{-1}$): 3395 (m, amide); 3057 (m, $NH_3^+$); 1718 and 1669 (s, C=O).

Microanalysis: $C_{15}H_2N_3O_2.(COOH)_2 H_2O$

Found: C=53.09%; H=6.54%; N=10.84%;

Calculated: C=53.26%; H=6.57%; N=10.96%;

EXAMPLE 18

Preparation of 1-(2(S)-amino-butyryl)-2(R/S)-(5-methoxy)indolinecarboxylic Acid n-butylamide; Route 7

$R_1=CH_2CH_3$; $R_2=H$; n=0 and m=1;

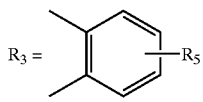

$R_6=OCH_3$; R=R'=H; $R_4$=CO—NH—$R_5$; $R_5$=n—$C_4H_9$ a) Preparation of the ethyl ester of 5-methoxy-2-indolecarboxylic acid: compound XXXXII p-Anisidine (61.5 g, 499 mmol) is treated in 500 ml of 15% HCl containing 500 g of ice by dropwise addition for 5 minutes of a solution of sodium nitrite (37.5 g, 543 mmol) in water (100 ml). 3 g of activated charcoal are added and the mixture is stirred for 10 minutes. After filtration, the filtrate is rapidly added to ethyl 2-methylacetoacetate (80 g, 554 mmol) and anhydrous sodium acetate (410 g, 4.998 mol) in ethanol (500 ml) containing 500 g of ice. The mixture is stirred for 2 hours and then extracted with toluene (3×500 ml). The extracts are dried ($Na_2SO_4$) and the solvent removed in order to obtain crude ethyl 1-(p-methoxyphenylazo)-1-methylacetoacetate in the form of an oil. This oil is added to a cold solution of HCl in ethanol (38–40% by weight). The mixture is brought to and maintained at reflux for 40 minutes. The mixture is stirred for 2 hours at room temperature, water (150 ml) is added and it is then refrigerated. The product separates out in the form of orange crystals which are collected and washed with cold ethanol and then with water.

$^1$H-NMR ($CDCl_3$, ppm): 9.03 (1H, broad s, NH); 7.31 (1H, dd, ArCH); 7.14 (1H, t, ArCH); 7.07 (1H, d, ArCH); 6.99 (1H, dd, ArCH); 4.40 (2H, q, $CH_2$); 3.84 (3H, s, $CH_3O$); 1.43 (3H, t, $CH_3CH_2$).

b) Preparation of 5-methoxy-2(R/S)-indolinecarboxylic acid n-butylamide: compound XXXXIV The product of step a) (10 g, 53 mmol) is dissolved in methanol (100 ml) and treated with magnesium (3.6 g, 150 mmol). The reaction temperature is maintained at 15–20° C. by external cooling and the mixture is stirred overnight. It is then diluted with 300 ml of water and extracted with methylene chloride (4×100 ml). The extracts are dried ($Na_2SO_4$) and the solvent removed to give the methyl ester of 5-methoxy-2(R/S)-indolinecarboxylic acid (compound XXXXIII). This compound is dissolved in butylamine (40 ml) and refluxed under nitrogen for 3 hours. The excess amine is removed and the residue crystallized from ether to give compound XXXXIV.

m.p;=119–121° C.

$^1$H-NMR ($CDCl_3$, ppm): 7.2 (1H, s, NHCO); 6.6–6.7 (3H, m, ArCH); 4.37 (1H, t, NHCHCO); 3.90 (1H, s, NH indoline); 3.73 (3H, s, $OCH_3$); 3.54 (1H, dd, ArC(H)H); 3.27 (2H, m, $NHCH_2$); 3.05 (1H, dd, ArC(H)H); 1.2–1.5 (4H, m, $CH_3(CH_2)_2$), 0.89 (3H, t, $CH_3(CH_2)_2$).

c) Preparation of 1-(N-benzyloxycarbonyl)-2(S)-aminobutyryl)-2(R/S)-(5-methoxy)indolinecarboxylic acid n-butylamide: compound XXXXV 2.37 g (10 mmol) of N-benzyloxycarbonyl-2(S)-aminobutyric acid, obtained according to Example 3 a), and the compound obtained in step b) (2.48 g, 10 mmol) are dissolved in anhydrous methylene chloride and cooled to 0° C. The mixture is treated with triethylamine (2.03 g, 20 mmol) and then with bis(2-oxo-3-oxazolidinyl)phosphinyl chloride (2.8 g, 10 mmol). The reaction mixture is stirred overnight at room temperature. It is washed with 10% citric acid solution (3×100 ml) and then with 5% sodium bicarbonate solution (3×100 ml), dried ($Na_2SO_4$) and the solvent is removed. The product is purified by chromatography on silica gel, eluting with 1/2 ethyl acetate/petroleum ether.

$^1$H-NMR ($CDCl_3$, ppm): 8.0 (0.5H, m, NH); 7.2–7.3 (5H, m, Ph); 6.6–7.1 (3.5H, m, NH and ArCH indoline); 4.7–5.7 (4H, m, $PhCH_2$, NH, NCHCO of butyric acid); 4.0–4.3 (1H, m, NCHCO indoline); 3.78 (3H, s, $OCH_3$); 3.45 (1H, m, ArCH(H) indoline); 3.0–3.2 (3H, m, $NHCH_2$, ArCH(H) indoline); 0.7–2.0 (12H, 3×$CH_2$, 2×$CH_3$).

Mass spectrum (FAB): m/e=468 ($M^+$+1).

d) Preparation of the title compound in the form of the oxalate salt

The compound of step c) (2.8 g, 6 mmol) is dissolved in 100 ml of methanol containing palladium-on-charcoal (10%, 0.8 g, 50% water) and the mixture is hydrogenated at 40 psi for 2.5 hours. The catalyst is removed by filtration and the solvent removed. The residue is treated with oxalic acid (0.85 g, 9.4 mmol) in ethanol (10 ml) and then with ether (500 ml) and the product precipitates.

Microanalysis: $C_{18}H_{27}N_3O_3.(COOH)_2.0.25H_2O$:

Found: C=56.14%; H=6.98%; N=9.57%;

Calculated: C=56.13%; H=6.95%; N=9.82%;

Mass spectrum (FAB): m/e=333 ($M^+$)

$^1$H-NMR (DMSO-$d_6$, ppm): 8.3–9.1 (masked ArCH); 7.97 (1H, dd, CONH); 6.7–7.0 (2H, m, ArCH); 4.9–5.3 (1H, m, NCHCO indoline); 3.2–3.9 (5H, m, $CH_3O$, NCHCO butyl, ArCH (H)); 2.7–3.2 (3H, m, $CONHCH_2$ ArCH(H)); 1.0–2.0 (6H, m, $CH_3CH_2$, $CH_3(CH_2)_2$); 0.7–1.0 (2×$CH_3CH_2$).

e) Optical separation of 1-(2(S)-aminobutyryl)-2(R/S)-(5-methoxy)indolinecarboxylic acid n-butylamide 1-(N-Benzyloxycarbonyl-2(S)-aminobutyryl)-2 (R/S) -(5-methoxy) indolinecarboxylic acid n-butylamide (compound XXXXV) is separated into its diastereoisomers by chromatography on a column of silica gel, using a methylene chloride/diethyl ether (10/1) mixture as eluent.

The (S,S) isomer is eluted first. It is collected and recrystallized from methanol and the benzyloxycarbonyl protecting group is then removed by hydrogenation in the presence of palladium-on-charcoal in methanol for 2 hours 30 minutes at a hydrogen pressure of 60 psi, as described above. The catalyst is removed by filtration and the residue is treated with oxalic acid in methanol and then with ether in order to lead to the oxalate salt.

m.p.=185–190° C.

Microanalysis: $C_{18}H_{27}N_3O_3.1.4C_2H_2O_4.0.5H_2O$:

Found: C=53.5%; H=6.81%; N=9.05%;

Calculated: C=53.3%; H=6.63%; N=8.97%;

The (S,R) isomer is eluted second. It is treated in a similar manner to the (S,S) isomer in order to obtain the oxalate salt.

m.p.=95–105° C.

Microanalysis: $C_{18}H_{27}N_3O_3.1.35C_2H_2O_4$:

Found: C=54.5%; H=6.55%; N=9.45%;

Calculated: C=54.1%; H=6.58%; N=9.24%;

EXAMPLE 19

Preparation of 1-(2(S)-aminobutyryl)-2(R/S)-(6-methoxy)indolinecarboxylic acid n-butylamide; Route 7

$R_1=CH_2CH_3$; $R_2=H$; n=0 and m=1;

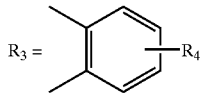

$R_6=OCH_3$; R=R'=H; $R_4=CO-NH-R_5$; $R_5$n-$C_4H_9$

The process is performed as in Example 18. The title compound is obtained in the form of the oxalate salt.

Microanalysis: $C_{18}H_{27}N_3O_3.(COOH)_2H_2O$:

Found: C=54.54%; H=7.08%; N=9.52%;

Calculated: C=54.41%; H=7.08%; N=9.52%;

$^1$H-NMR (DMSO-$d_6$, ppm): 8.5 (1H, b, NH); 7.3–8.2 (6H, m, $NH_3^+$, ArCH, $H_2O$); 7.0–7.2 (1H, m, ArCH); 6.5–6.7 (1H, m, ArCH); 5.05 (1H, dd, NCHCO indoline); 3.2–4.1 (5H, m, $CH_3O$, ArCH(H), NCHCO butyryl); 2.7–3.2 (3H, m, $NCH_2$ ArCH(H)); 1.5–2.0 (2H, m, $CH_2$); 1.0–1.5 (4H, m, 2×$CH_2$); 0.7–1.0 (6H, m, 2×$CH_3$).

EXAMPLE 20

Preparation of 1-(2(S)-aminobutyryl)-2(R/S)-(5-fluoro)indolinecarboxylic Acid N-butylamide; Route 7

$R_1=CH_2CH_3$; $R_2=H$; n=0 and m=1;

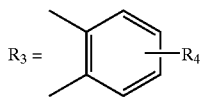

$R_6=F$; R=R'=H; $R_4=CO-NH-R_5$; $R_5=N-C_4H_9$ a) Preparation of the ethyl ester of (5-fluoro)-2-indolecarboxylic acid: compound XXXXII The process is performed as in Example 18 a) in order to prepare ethyl 1-(p-fluorophenylazo)-1-methylacetoacetate starting with p-fluoroaniline and ethyl 2-methylacetoacetate. It is dissolved in 270 ml of acetic acid containing 15 ml of sulphuric acid and the mixture is then refluxed for 15 minutes. After cooling to room temperature, 500 ml of water are added and the mixture is extracted with ether (500 ml) and with methylene chloride (500 ml). The combined extracts are washed with water (1000 ml) and with 10% potassium carbonate solution (300 ml), dried and the solvent is removed. The product is then obtained by crystallization from ethanol.

$^1$H-NMR (CDCl$_3$, ppm): 7.0–7.4 (4H, m, ArCH); 4.41 (2H, q, $CH_2$) ; 1.40 (3H, t, $CH_3$).

b) Preparation of 5-fluoro-2(R/S)-indolinecarboxylic acid n-butylamide: compound XXXXIV.

The process is performed as in Example 18 b).

m.p.=93–5° C.

$^1$H-NMR (CDCl$_3$, ppm): 7.12 (1H, b, NH); 6.6–6.9 (3H, m, ArCH; 4.42 (1H, t, NHCHCO); 4.03 (1H, b, NH); 3.56 (1H, dd, ArCH(H)); 3.27 (2H, m, $CH_2NH$); 3.05 (1H, m, ArCH(H)); 1.2–1.7 ($CH_3(CH_2)_2$); 0.90 (3H, t, $CH_3$).

Mass spectrum (FAB): m/e=237 ($M^+$+1).

c) Preparation of 1-(N-(benzyloxycarbonyl)-2(S)-aminobutyryl)-2(R/S)-(5-fluoro)indolinecarboxylic acid n-butylamide; compound XXXXV The process is performed as in Example 18 c) and the product is then purified by chromatography on silica gel (eluent: 1/1 ethyl acetate/petroleum ether).

m.p.=192–3° C.

$^1$H-NMR (CDCl$_3$, ppm): 8.05 (1H, b, NH); 7.2–7.4 (5H, m, Ph); 6.8–7.1 (4H, m, NH, ArCH indoline); 4.7–5.4 (4H, m, PhCH$_2$, 2×NCHCO); 3.5 (2H, m, ArCH$_2$ indoline); 3.2 (2H, m, CH$_2$NHCO); 0.7–2.0 (12H, m, CH$_3$CH$_2$ and CH$_3$ (CH$_2$)$_2$).

d) Preparation of the title compound in the form of the oxalate salt

The process is performed as in Example 18 d).

Microanalysis: $C_{17}H_{24}FN_3O_2.(COOH)_2.0.75H_2O$:

Found: C=53.58%; H=6.60%; N=10.25%;

Calculated: C=53.70%; H=6.52%; N=9.89%.

$^1$H-NMR (DMSO-$d_6$, ppm): 8.60 (1H, b, NH); 7.8–8.1 (1H, m, ArCH); 7.2–7.8 (4H, b, $NH_3^+$ and $H_2O$); 6.8–7.2 (2H, m, ArCH); 5.0–5.2 (1H, m, NHCHCO indoline); 2.6–3.8 (5H, m, NCHCO butyryl, ArCH$_2$, CH$_2$NHCO); 1.5–2.0 (2H, m, CH$_2$); 1.0–1.5 (4H, m, 2×CH$_2$); 0.6–1.0 (6H, m, 2×CH$_3$).

Mass spectrum (FAB): m/e=322 ($M^+$=1).

e) Optical separation of 1-(2(S)-aminobutyryl)-2(R/S)-(5-fluoro)indolinecarboxylic acid n-butylamide 1-(N-(Benzyloxycarbonyl)-2(S)-aminobutyryl)-2(R/S)-(5-fluoro)indolinecarboxylic acid is separated into its diastereoisomers by chromatography on a column of silica gel, using a petroleum ether (P.E.=60–80° C.)/ethyl acetate mixture (2/1) as eluent.

The (S,R) isomer is eluted first. It is recrystallized from a petroleum/diethyl ether mixture and then deprotected by hydrogenation as indicated in Example 18 e). The (S,R) isomer is obtained in the form of the oxalate salt.

m.p.=173–177° C.

Analysis: $C_{17}H_{24}FN_3O_2.C_2H_2O_4.H_2O$:

Found: C=52.9%; H=6.37%; N 9.52%;

Calculated: C=53.14%; H=6.57%; N=9.78%.

The (S,S) isomer is eluted second and treated in the same way as the first isomer in order to purify and deprotect it. The (S,S) isomer is also obtained in the form of the oxalate salt.

m.p.=105–110° C.

Microanalysis: $C_{17}H_{24}FN_3O_2.C_2H_2O_4.H_2O$:

Found: C=52.9%; H=6.37%; N=9.70%;
Calculated: C=53.14%; H=6.57%; N=9.78%.

EXAMPLE 21

Preparation of 1-(2(S)-aminobutyryl)-2(R/S)-5-benzyloxy)indolinecarboxylic Acid N-butylamide; Route 7

$R_1=CH_2CH_3$; $R_2=H$; n=0 and m=1;

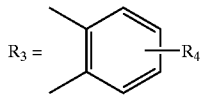

$R_6=OCH_2Ph$; $R=R'=H$; $R_4=CO-NH-R_5$; $R_5=n-C_5H_9$

The process is performed as in Example 18.

1-(N-(tert-Butoxycarbonyl)-(S)-aminobutyryl)-2(R/S)-(5-benzyloxy)indolinecarboxylic acid n-butylamide (3.56 g, 7 mmol) is dissolved in ethyl acetate (20 ml) and then treated with HCl in ethyl acetate (3M, 25 ml). The mixture is stirred at room temperature for 1 h and the solid formed is collected, washed and dried. The title compound is isolated in the form of the hydrochloride.

Microanalysis: $C_{24}H_{31}N_3O_3 \cdot HCl \cdot H_2O$
Found: C=63.28%; H=6.92%; N=9.20%;
Calculated: C=63.36%; H=7.31%; N=9.24%.

$^1$H-NMR (DMSO-$d_6$, ppm): 8.7 (0.9H, broad s, NH of one diastereoisomer); 8.5 (broad s, $NH_3^+$ and $H_2O$); 8.07 (0.1H, NH of the second diastereoisomer); 7.93 (1H, d, ArCH); 7.2–7.5 (5H, m, ArCH); 6.93 (1H, s, ArCH); 6.84 (1H, dd, ArCH); 5.35 (0.9H, dd, NCHCO indoline of one diastereoisomer); 4.9–5.2 (2.1H, $PhCH_2$, NCHCO indoline of the second diastereoisomer); 4.7 (0.1H, m, NCHCO butyryl of one diastereoisomer); 3.92 (0.9H, m, NCHCO butyryl of the second diastereoisomer); 3.4–3.7 (1H, m, ArCH(H) indoline); 2.8–3.1 (3H, m, ArCH(H) indoline, $NCH_2$); 1.5–2.0 (2H, m, $CH_2$); 1.05–1.5 (4H, m, $2\times CH_2$); 0.7–1.0 (6H, m, $2\times CH_3$).

Mass spectrum (FAB): m/e=410 ($M^+$+1).

EXAMPLE 22

Preparation of 1-(2(S)-aminobutyryl)-2(S)-[(3aS,7aS)-perhydro]indolinecarboxylic Acid N-butylamide; Route 3

$R_1=CH_2CH_3$; $R_2=H$; n=0 and m=1;

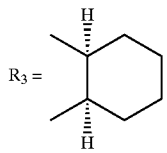

$R=R'=H$; $R_4=CO-NH-R_5$; $R_5=n-C_4H_9$ a) Preparation of 2(S)-[(3aS,7aS)-perhydro] indolinecarboxylic acid in the form of the N-acetate salt.

A solution of 2(S)-indolinecarboxylic acid (2.5 g, 15.32 mmol) in acetic acid containing $PtO_2$ (1 g) is hydrogenated at 55° C. for 2 hours and at 60 psi. The catalyst is removed by filtration and the solvent removed under vacuum in order to give a crude residue which is crystallized from diethyl ether in order to give, after filtration and washing with ether, a white solid.

m.p.=274–248° C.

$^1$H-NMR (200 MHz, $CD_3OD$, ppm): 4.05–3.90 (1H, m, junction H); 3.70–3.55 (1H, m, αH); 2.45–2.20 (2H, m, $CH_2-COOH$); 2.15–1.25 (12H, m, $CH_2$ cyclohexyl, junction H and $CH_3$ AcOH).

b) Preparation of N-(benzyloxycarbonyl)-2(S)-[(3aS,7aS) perhydro]indolinecarboxylic acid.

A solution of the compound obtained in step a), (1.28 g, 5.58 mmol) in 2N NaOH is cooled in a water/ice bath and stirred vigorously. Benzyl chloroformate (0.95 ml, 6.65 mmol) and 2N sodium hydroxide (30 ml) are added (in about 10 portions). The temperature of the reaction mixture is maintained between 5 and 10° C. by adjusting the rate of addition of the reactants. 40 ml of 2N sodium hydroxide are added and the mixture is maintained at room temperature for 30 minutes. The alkaline solution is washed with ether (4×50 ml) and then acidified to pH<2 by addition of 5N HCl. The solution is extracted with $CH_2Cl_2$ and the extracts are dried over $MgSO_4$, filtered and evaporated under vacuum. The oil obtained is dried under vacuum over $P_2O_5$ in order to obtain the desired product.

$^1$H-NMR (200 MHz, $CDCl_3$, ppm): 7.14 (5H, broad s, ArCH); 5.05 (2H, broad s, H benzyl); 4.20–4.10 (1H, m, junction H); 4.00–3.75 (1H, m, αH); 2.20–1.00 (11H, m, $CH_2$ cyclohexyl, junction H', $CH_2COOH$)

c) Preparation of N-benzyloxycarbonyl-2(S)-[(3aS,7aS) perhydro]indolinecarboxylic acid n-butylamide The process is performed as in Example 11, step c), using the product obtained in Example 22, step b).

1.40 g of the product obtained in the above step (4.61 mmol) are dissolved in 50 ml of anhydrous tetrahydrofuran and 0.58 ml of 4-ethylmorpholine (4.61 mmol) are added at a temperature of 0° C. This solution is cooled to −5° C. and 0.60 ml of isobutyl chloroformate (4.61 mmol) are added dropwise. After 30 minutes at −5° C., 0.46 ml of butylamine (4.61 mmol) is added to the solution and the mixture is then left overnight at room temperature. 70 ml of dichloromethane are then added and this solution is washed with 3×50 ml of 10% citric acid. After vigorous stirring, the phases are separated. The organic phase is washed with 2×50 ml of 5% $NaHCO_3$. After drying over $MgSO_4$, the solution is evaporated under vacuum and the crude amide is obtained, which is used without further purification.

$^1$H-NMR (200 MHz, $CDCl_3$, ppm): 7.30 (5H, broad s, ArCH); 5.05 (2H, broad s, H benzyl); 4.20 (1H, m, αH); 4.00–3.80 (1H, m, junction H); 3.80–3.60 (1H, m, NH); 3.20–3.00 (2H, m, $CH_2-NH$ butylamide); 2.30–1.00 (15H, m, $CH_2$ cyclohexyl, $CH_2-CH_2-BuNH$, junction H, $CH_2-COOH$); 1.00–0.80 (6H, m, $CH_3$ butylamide).

d) Preparation of 2-[(2S,3aS,7aS)perhydro] indolinecarboxylic acid n-butylamide

The product of step c) (1.70 g, 4.54 mmol) dissolved in 200 ml of methanol is hydrogenated at room temperature for 2 hours 30 minutes at 60 psi, using 0.6 g of Pd/C (10%, wet) as catalyst. The amide is isolated in the form of an oil.

$^1$H-NMR (200 MHz, $CDCl_3$, ppm): 7.80 (1H, broad s, NH); 3.90–3.80 (1H, m, αH); 3.50–3.00 (3H, m, $-CH_2-$ NH—BuNH—, junction H); 3.00–1.05 (15H, m, $-CH_2-$ cyclohexyl, junction H, $-CH_2-$ butylamide); 0.95 (3H, t, $CH_3$ butylamide)

e) Preparation of 1-(N-benzyloxycarbonyl-2(S)-aminobutyryl)-2(S)-[(3aS,7aS)perhydro]indolinecarboxylic acid n-butylamide N-benzyloxycarbonyl-2(S)-aminobutyric acid obtained as in Example 3 a) (0.95 g, 4 mmol) is dissolved in 45 ml of anhydrous tetrahydrofuran and 0.51 ml of 4-ethylmorpholine (4.01 mmol) is added at 0° C. This solution is cooled to −5° C. and treated dropwise with isobutyl chloroformate (0.52 ml, 4.01 mmol). After 30 minutes at −5° C., the compound of step d) (0.90 g, 4.01 mmol) dissolved in 5 ml of anhydrous tetrahydrofuran is added to the mixture and the mixture thus obtained is left standing overnight at room temperature. 50 ml of dichloromethane are then added, after which the mixture is washed with 3×50 ml of 10% citric acid solution. The organic phase is washed with 2×50 ml of 5% $NaHCO_3$. After drying over $MgSO_4$, the solution is evaporated under vacuum and a crude product is obtained, which is purified by flash chromatography on silica, eluting with an ethyl acetate/ether mixture (15/85 and then 35/65). This allows the desired product to be obtained in the form of an oil. It is dried overnight at reduced pressure over $P_2O_5$.

$^1$H-NMR (200 MHz, $CDCl_3$, ppm); 7.20 (5H, broad s, ArCH); 6.90 (1H, broad s, —NH—); 5.45 (1H, d, —NH—); 5.10–4.95 (2H, m, H benzyl); 4.50–4.30 (2H, m, junction H and αH); 4.10–4.00 (1H, m, αH); 3.20–3.00 (2H, m, —$CH_2$— butylamide); 2.65–1.00 (17H, m, —$CH_2$— cyclohexyl, junction H, —$CH_2$— aminobutyryl, —CH— butylamide); 1.00–0.90 (6H, m, $CH_3$ aminobutyryl and $CH_3$ butylamide)

Mass spectrum (FAB): m/e (% intensity): 444 ($MH^+$, 13.5); 225 (56); 124 (100); 91 (91).

f) Preparation of the title compound

A solution of the compound obtained in step e) (0.66 g, 1.49 mmol) in 100 ml of methanol is hydrogenated for 3 hours using a Pd/C catalyst (0.25 g, 10%, wet) at 60 psi. The catalyst is removed by filtration and the solvent evaporated under vacuum. 0.18 g of oxalic acid (1.98 mmol) is added to the crude. oil thus obtained, in ethanol, and ether is then added thereto. After crystallization, filtration and drying under vacuum, the desired product is obtained.

m.p.=168–9° C. (open capillary)

$^1$H-NMR (400 MHz, $CD_3OD$, ppm): 4.30–4.25 (1H, m αH); 4.05–3.85 and 3.40–3.35 (2H, m, αH and 7aH); 3.15–2.98 (2H, m, —$CH_2$—NH—$BuNH_2$); 2.33–2.15 (1H, m, 3aH); 2.05–1.50 (9H, m, —$CH_2$— aminobutyryl, —$CH_2$— perhydroindoline); 1.45–1.05 (7H, m, —$CH_2$— $CH_2$—$BuNH_2$ and H proline); 0.95–0.75 (6H, m, —$CH_3$ aminobutyryl and —$CH_3$ $BuNH_2$).

Mass spectrum (FAB): m/e (% intensity)=332 $(MH+Na)^+$, 1); 310 ($MH^+$, 100); 225 (75); 124 (66); 59 ($C_7H_7^+$, 43).

IR (KBr disc, $cm^{-1}$): 3342 ($NH_3^+$, wave) ; 3049 (NH, vague); 2937 (CH, s); 2857 (CH, s); 1745 (C=O, s); 1682 (s); 1652 (s).

Microanalysis: $C_{17}H_{31}N_2O_2.1.0C_2H_2O_4.0.3H_2O$:

Found: C=56.34%; H=8.37%; N 10.33%;

Calculated: C=56.36%; H=8.36%; N=10.38%.

EXAMPLE 23

Preparation of 2-(2(S)-aminobutyryl)-1-(R/S)-isoindolinecarboxylic Acid N-butylamide; Route 4

$R_1=CH_2CH_3$; $R_2=H$; n=1 and m=0;

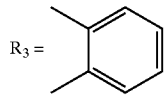

R=R'=H; $R_4$=CO—NH—$R_5$; $R_5$=n-$C_4H_9$ a) Preparation of o-(bromomethyl)phenylacetic acid o-Tolylacetic acid (40 g, 266 mmol), N-bromosuccinimide (52.147 g, 293 mmol) and benzoyl peroxide (0.174 g, catalytic) are dissolved in 300 ml of $CCl_4$. The suspension is brought to and maintained at reflux for 12 hours. After cooling, the solid particles are separated out by filtration. and the $CCl_4$ is evaporated off under vacuum, which allows a white solid to appear. This is sufficiently pure without recrystallization.

$^1$H-NMR ($CDCl_3$, ppm): 7.25 (4H, m, ArH); 4.3 (2H, s, $CH_2COOH$); 3.7 (2H, S, $CH_2Br$).

b) Preparation of the methyl ester of o-(bromomethyl) phenylbromoacetic acid

The acid obtained in step a) is dissolved in 44 ml of $SOCl_2$ and heated for 3 hours at 55° C. The $SOCl_2$ is removed under vacuum and the resulting brown oil is treated with 26 ml of $Br_2$ by irradiation using a 450 W UV lamp for 2 hours. After addition, the bromine is removed by distillation under vacuum and the black residue is poured into 305 ml of methanol. The methanol is then removed and a black oil remains, which is distilled under pressure of 0.1 mm Hg. The distillation fractions which come off between 120 and 130° C. are collected.

$^1$H-NMR ($CDCl_3$, ppm): 7.0–7.50 (4H, m, ArH); 5.7 (1H, s, CH); 4.3 (2H, d, $CH_2Br$); 3.7 (3H, s, $CH_3$)

c) Preparation of the methyl ester of N-benzyl-1(R/S)-isoindolinecarboxylic acid in the form of the hydrochloride.

The methyl ester (46.4 g, 144 mmol) obtained in step b) is dissolved in anhydrous toluene (288 ml) under nitrogen. 46.35 g of benzylamine (864 ml) are added using an ice/salt mixture. The mixture is stirred for 72 hours. Next, the amine hydrobromide is removed by filtration and the toluene removed under vacuum. The yellow oil obtained is dissolved in ether and HCl is bubbled through in order to obtain the hydrochloride.

m.p.=160–161° C.

$^1$H-NMR ($D_2O$, ppm): 7.00 (9H, m, ArH) ; 5.20 (1H, s, αH); 4.10 (2H, d, $CH_2$ ring); 4.00 (2H, d, $CH_2Bn$); 3.10 (3H, s, $CH_3$)

d) Preparation of the methyl ester of 1(R/S)-isoindolinecarboxylic acid in the form of the hydrochloride The product of step c) (5 g, 16 mmol) is dissolved in 100 ml of ethanol and Pd/C (10%, wet) is added. The suspension is stirred at 40 psi of hydrogen and at 50° C. for 8 hours. The catalyst is extracted by filtration and the ethanol concentrated to a small volume. The addition of ether allows white crystals to appear. The degree of purity of the product is sufficient and recrystallization is not necessary.

m.p.=159–161° C.

$^1$H-NMR ($CD_3OD$, ppm): 7.25–7.30 (4H, m, ArH); 5.50 (1H, s, αH); 4.50 (2H, d, $CH_2$ ring); 3.8 (3H, s, $CH_3$).

e) Preparation of the methyl ester of 2-(N-(benzyloxycarbonyl)-2(S)-aminobutyryl)-1(R/S)-isoindolinecarboxylic acid N-Benzyloxycarbonyl-2(S)-aminobutyric acid (compound of Example 3, step a)) (2.62 g, 11.04 mmol) is dissolved in 100 ml of tetrahydrofuran under nitrogen and cooled on an ice/salt mixture. N-Ethylmorpholine (1.27 g, 11.04 mmol) is added, followed by isobutyl chloroformate (1.51 g, 11.04 mmol). After 30 minutes, the compound obtained in step d) (2.347 g, 11.04 mmol) is added. Stirring is continued overnight. The mixture is then poured into 200 ml of $CH_2Cl_2$, washed with 3×100 ml of citric acid (10%) and then with 3×100 ml of $NaHCO_3$ (5%), dried and evaporated until a clear oil is obtained.

$^1$H-NMR ($CDCl_3$, ppm): 7.25 (9H, m, ArH); 5.75 (1H, m, αH); 5.10 (2H, s, $CH_2$ benzyloxycarbonyl); 4.60–5.00 (3H, m, αH, $CH_2$ ring); 3.8 (3H, s, $OCH_3$); 1.60–2.00 (2H, m, $CH_2$ aminobutyryl); 1.0 (3H, m, $CH_3$ aminobutyryl).

f) Preparation of 2-(N-benzyloxycarbonyl-2(S)-aminobutyryl)-1(R/S)-isoindolinecarboxylic acid The compound of step e) (3.422 g, 8.6 mmol) is dissolved in 69 ml of methanol. 8.6 ml of 2N NaOH are added and the solution is stirred at room temperature for 24 hours. 172 ml of water are then added and the methanol is removed under vacuum. The solution is acidified with concentrated HCl to pH 2 and the resulting suspension is extracted with $CH_2Cl_2$. After drying, the $CH_2Cl_2$ is removed. An oil remains.

$^1$H-NMR ($CDCl_3$, ppm): 7.00–7.30 (9H, m, ArH); 5.75 (2H, m, $CH_2$ ring); 4.8–5.2 (3H, m, αH, $CH_2$ benzyloxycarbonyl); 4.60 (1H, m, αH); 1.90 (2H, m, $CH_2$ aminobutyryl); 1.0 (3H, m, $CH_3$ aminobutyryl).

g) Preparation of 2-(N-benzyloxycarbonyl-2(S)-aminobutyryl)-1(R/S)-isoindolinecarboxylic acid n-butylamide The compound of step f) (2.70 g, 7.07 mmol) is dissolved in 100 ml of tetrahydrofuran under nitrogen and cooled on an ice/salt mixture. N-Ethylmorpholine (0.814 g, 7.07 mmol) is added, followed by isobutyl chloroformate (0.966 g, 7.07 mmol). After 30 minutes, n-butylamine (0.517 g, 7.07 mmol) is added and the stirring is continued overnight. The mixture is poured into 200 ml of $CH_2Cl_2$, washed with 3×100 ml of citric acid (10%) and then with 3×1.00 ml of $NaHCO_3$ (5%), dried and evaporated until a clear oil is obtained.

$^1$H-NMR ($CDCl_3$, ppm): 7.25 (9H, m, ArH); 5.20–5.30 (2H, m, $CH_2$ ring); 4.80–5.10 (3H, m, αH, $CH_2$ benzyloxycarbonyl); 4.00–4.25 (1H, m, αH); 3.0 (2H, m, $CH_2N$); 1.00–1.90 (6h, m, $CH_2$ aminobutyryl, $CH_3CH_2CH_2$); 0.8–1.5 (6H, m, $CH_3$ aminobutyryl, $CH_3$ butyl).

h) Preparation of the title compound in the form of the oxalate salt

The compound of step g) is hydrogenated in the same manner as Example 5, step c), and the product is isolated as the oxalate salt.

m.p.=90–92° C.

$^1$H-NMR ($CD_3OD$, ppm): 7.00–7.25 (4H, m, ArH); 5.30 (1H, m, NCHCO); 4.8–5.0 (2H, m, $CH_2$ isoindoline); 3.25 (1H, m, NCHCO); 2.90–3.00 (2H, m, $CH_2N$); 1.50–2.00 (2H, m, $CH_2$ aminobutyryl); 0.8–1.2 (10H, m, $CH_3CH_2CH_2$ $CH_3$ aminobutyryl).

Microanalysis: $C_{17}H_{25}N_3O_2 \cdot C_2H_2O_4 \cdot 1.25H_2O$:

Found: C=54.98%; H=7.30%; N=10.66%;

Calculated: C=54.86%; H=7.15%; N=10.10%.

Examples 24 to 36 correspond to compounds of formula (I) in which:

$R_2$=H, n=0 and m=1, $R_3$ represents the unit

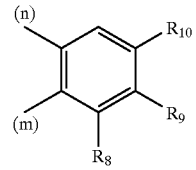

$R_4$=CONHR$_5$ and $R_5$=n-butyl, $R_1$, R, R', $R_8$, $R_9$ and $R_{10}$ being as defined in each example.

EXAMPLE 24
Route 8

Preparation of 1-(N-benzyloxycarbonyl-L-valyl)-5-methoxyindoline-2(R/S)-carboxylic Acid Butylamide Triethylamine (2.25 ml, 16 mmol) and bis(2-oxo-3-oxazolidinyl)phosphinyl chloride (1.539 g, 6.054 mmol) were added to a cooled solution (0° C.) of 5-methoxyindoline-2(R/S)-carboxylic acid (1.000 g, 4.03 mmol) and N-benzyloxycarbonyl-L-valine (1.135 g, 4.50 mmol) dissolved in dichloromethane (50 ml), under nitrogen. The mixture was stirred at room temperature for 22 hours and then washed with 10% citric acid (3×50 ml), 5% $NaHCO_3$ (3×50 ml) and water (50 ml). The organic phase was dried and concentrated: the residue was purified by chromatography on a column of silica gel, using a 3/2 petroleum ether/ethyl acetate mixture as eluent. A white solid was obtained.

Melting point: 124–126° C.

$^1$H-NMR ($CDCl_3$) δ (ppm) 8.03 (1H, m, CONH), 7.24–7.47 (5H, m, ArH), 6.71–6.89 (3H, m, ArH), 4.86–5.65 (4H, m, COCHNH of the valine, PhCH$_2$), 3.75–4.15 (4H, m, COCHN of the indoline, $OCH_3$), 3.46–3.51 (1H, m, CH(H) of the indoline), 3.09–3.21 (3H, m, CH(H) of the indoline, CONCH$_2$), 1.85–2.12 (1H, m, CHMe$_2$), 0.78–1.42 (13H, m, $CH_2CH_2CH_3$ of the butyl, 2×$CH_3$ of the valine).

Preparation of 1-(L-valyl)-5-methoxyindoline-2(R/S)-carboxylic Acid Butylamide Oxalate: $R_1$=CH(CH$_3$)$_2$, R=R'=$R_8$=$R_{10}$=H, $R_9$=OCH$_3$ Activated palladium-on-charcoal (0.2 g, containing 10% water) was added to a solution of 1-(N-benzyloxycarbonyl-L-valyl)-5-methoxyindoline-2(R/S)-carboxylic acid butylamide (0.502 g, 1.04 mmol) in methanol (20 ml). The mixture was hydrogenated for two and a half hours at room temperature. After removing the catalyst by filtration, oxalic acid (0.130 g, 1.44 mmol) was added to the filtrate; the solvent was removed and the residue, which crystallized from a methanol/diethyl ether mixture, gave a white solid.

Melting point: 112–120° C.

$C_{19}H_{29}N_3O_3 \cdot 1.25(COOH)_2$, required: C, 56.14%; H, 6.90%; N, 9.13%;

found: C, 56.01%; H; 6.93%; N, 9.30%.

$^1$H-NMR (DMSO-d$_6$), δ (ppm) 8.46–8.53 (1H, m, CONH), 7.91–8.06 (1H, d, ArH), 6.77–6.94 (2H, m, ArH), 4.95–5.30 (1H, m, COCHN of the indoline), 2.94–3.91 (8H, m, COCHN of the valine, $CH_3O$, $CH_2$ of the indoline, CONHCH$_2$), 2.05–2.24 (1H, m, CHMe$_2$), 0.81–1.46 (13H, m, $CH_2CH_2CH_3$, 2×$CH_3$ of the valine).

EXAMPLE 25

Route 8

Preparation of 1-(N-benzyloxycarbonyl-L-alanyl)-5-methoxyindoline-2(R/S)-carboxylic Acid Butylamide Triethylamine (1.12 ml, 8 mmol) and bis(2-oxo-3-oxazolidinyl)phosphinyl chloride (0.815 g, 3.2 mmol) were added to a cooled (0° C.) solution of 5-methoxyindoline-2(R/S)-carboxylic acid butylamide (0.500 g, 2.01 mmol) and N-benzyloxycarbonyl-L-alanine (0.4956 g, 2.22 mmol) dissolved in dichloromethane (25 ml), under nitrogen. The mixture was stirred at room temperature for 22 hours. It was then washed with 10% citric acid (3×30 ml), 5% NaHCO$_3$ (3×30 ml) and water (30 ml). The organic phase was dried and concentrated and the residue was purified by chromatography on a column of silica gel, using a 1/1 petroleum ether/ethyl acetate mixture as eluent. A white solid was obtained.

Melting point: 106–109° C.

$^1$H-NMR (CDCl$_3$), δ (ppm) 8.00–8.07 (1H, m, CONH), 7.30–7.36 (5H, m, ArH), 6.72–7.02 (3H, m, ArH), 5.35–6.00 (1H, m, NH of the alanine), 4.95–5.20 (3H, m, PhCH$_2$, COCHN of the alanine), 4.20–4.80 (1H, m, COCHN of the indoline), 3.76 (3H, s, OCH$_3$), 3.40–3.60 (1H, m, CH(H) of the indoline), 3.09–3.30 (3H, m, CH(H) of the indoline, CONCH$_2$), 1.10–1.50 (7H, m, CH$_2$CH$_2$, CH$_3$ of the alanine), 0.78–0.87 (3H, m, CH$_3$ of the butyl).

Preparation of 1-(L-alanyl)-5-methoxyindoline-2(R/S)-carboxylic Acid Butylamide Oxalate: R$_1$=CH$_3$, R=R'=R$_8$=R$_{10}$=H, R$_9$=OCH$_3$ Activated palladium-on-charcoal (0.04 g, containing 10% water) was added to a solution of 1-(N-benzyloxycarbonyl-L-alanyl)-5-methoxyindoline-2(R/S)-carboxylic acid butylamide (0.130 g, 0.28 mmol) in methanol (6 ml). The mixture was hydrogenated for two and a half hours at room temperature. The. catalyst was removed by filtration and oxalic acid (0.028 g, 0.31 mmol) was then added to the filtrate, which was concentrated. Diethyl ether was added in order to make the product precipitate out, and this product was obtained in the form of a white solid.

Melting point: 112–118° C.

C$_{17}$H$_{25}$N$_3$O$_3$.1.14 (COOH)$_2$.0.9H$_2$O required: C, 51.51%; H, 6.46%; N, 9.10%;

found: C, 51.37%; H, 6.28%; N, 9.40%.

$^1$H-NMR (DMSO-d$_6$), δ (ppm) 8.44–8.47 (1H, m, CONH), 7.97–8.04 (1H, m, ArH), 6.78–6.92 (2H, m, ArH), 4.75–5.25 (1H, m, COCHN of the indoline), 3.35–4.10 (5H, m, COCHN of the alanine, CH(H) of the indoline, CH$_3$O), 2.99–3.13 (3H, m, CH(H) of the indoline, CONCH$_2$), 1.23–1.50 (7H, m, CH$_2$CH$_2$, CH$_3$ of the alanine), 0.87 (3H, t, CH$_3$ of the butyl).

EXAMPLE 26

Route 8

Preparation of 1-(N-benzyloxycarbonyl-L-alanyl)-5-methoxyindoline-2(S)-carboxylic Acid Butylamide 1-(N-Benzyloxycarbonyl-L-alanyl)-5-methoxyindoline-2(R/S)-carboxylic acid butylamide was prepared as described above. Careful chromatography on a column of silica gel, using a 1/1 petroleum ether/ethyl acetate mixture as eluent gave two diastereoisomers. The first to elute was the (R,S) isomer, followed by the (S,S) isomer.

Data for the (S,S) form:

$^1$H-NMR (CDCl3), δ (ppm) 8.02–8.05 (1H, m, CONH), 7.30–7.38 (5H, m, ArH), 6.73–7.00 (3H, m, ArH), 4.77–5.63 (4H, m, NH of the alanine, PhCH$_2$, COCHN of the alanine), 4.24–4.28 (1H, m, COCHN of the indoline), 3.78 (s, 3H, OCH$_3$), 3.49–3.54, 3.17–3.22 (m, 4H, CH$_2$ of the indoline, CONCH$_2$), 1.16–1.55 (m, 7H, CH$_2$CH$_2$, CH$_3$ of the alanine), 0.79–0.89 (m, 3H, CH$_3$ of the butyl).

Preparation of 1-(L-alanyl)-5-methoxyindoline-2(S)-carboxylic Butylamide Oxalate: R$_1$=CH$_3$, R=R'=R$_8$=R$_{10}$=H, R$_9$=OCH$_3$ Activated palladium-on-charcoal (0.04 g, containing 10% water) was added to a solution of 1-(N-benzyloxycarbonyl-L-alanyl)-5-methoxyindoline-2(S)-carboxylic acid butylamide (0.110 g, 0.234 mmol) in methanol (6 ml). The mixture was hydrogenated for two and a half hours at room temperature. The catalyst was removed by filtration and oxalic acid (0.0219 g, 0.25 mmol) was then added to the filtrate, which was concentrated. Diethyl ether was added in order to make the product precipitate out, and this product was obtained in the form of a white solid.

Melting point: 141–143° C.

C$_{17}$H$_{25}$N$_3$O$_3$.1.75(COOH)$_2$.0.25(H$_2$O), required: C, 51.14%; H, 6.07%; N, 8.73%;

found: C, 51.00%; H, 5.98%; N, 8.88%.

$^1$H-NMR (DMSO-d$_6$), δ (ppm) 8.48–8.51 (1H, m, CONH), 8.01 (1H, d, ArH), 6.89 (1H, s, ArH), 6.79 (1H, d, ArH), 5.00–5.03 (1H, m, COCHN of the indoline), 3.61–3.73 (5H, m, CH$_3$O, COCHN of the alanine, CH(H) of the indoline), 3.04–3.10 (3H, m, CH(H) of the indoline, CONCH$_2$), 1.25–1.51 (7H, m, CH$_2$CH$_2$ of the butyl, CH$_3$ of the alanine), 0.87 (3H, t, CH$_3$ of the butyl).

EXAMPLE 27

Route 9

Preparation of Ethyl Azidoacetate

A solution of ethyl bromoacetate (150 g, 0.901 mol) in dry acetonitrile (800 ml) was treated with sodium azide (58.57 g, 0.901 mol) under a nitrogen atmosphere, and the mixture was heated at reflux for 20 hours. After cooling, water (50 ml) was added and the mixture was stirred for half an hour; the upper phase was separated out and the lower phase was treated with a salt and extracted with diethyl ether. The organic phases were combined and the solvent removed at a temperature not exceeding 50° C., in order to give a yellow oil.

$^1$H-NMR (CDCl$_3$), δ (ppm) 4.24 (2H, q, OCH$_2$), 3.84 (2H, s, N$_3$ CH$_2$), 1.29 (3 H, t , CH$_3$).

Preparation of Ethyl 2-azido-3-(2-methoxyphenyl) propenoate

Pieces of sodium (3.678 g, 160 mmol) were added portionwise to ethanol (200 ml) over a period of 30 minutes. The resulting solution was cooled to −18° C. and a mixture of 2-methoxybenzaldehyde (4.832 g, 40 mmol) and ethyl azidoacetate (160 mmol) were then added over a period of one hour at a rate which allowed the temperature to be maintained below −15° C. After 3 hours, the solution was stored at 5° C. for 2 days in order to give a crystalline product which was collected by filtration and washed with cold hexane.

¹H-NMR (CDCl₃), δ (ppm) 8.19–8.20 (1H, m, ArCH—), 7.22–7.40 (2H, m, ArH), 6.84–7.04 (2H, m, ArH), 4.35 (2H, q, OCH₂), 3.84 (3H, s, OCH₃), 1.36 (3H, t, CH₃).

Preparation of Ethyl 4-methoxyindole-2-carboxylate

Ethyl 2-azido-3-(2-methoxyphenyl)propenoate (3.566 g, 144 mmol) was suspended in toluene (800 ml) and the mixture was refluxed for three hours, then cooled and stirred at room temperature overnight. The ethyl 4-methoxyindole-2-carboxylate formed as a yellow solid and was collected.

Melting point: 168–170° C.

H-NMR (CDCl₃), δ (ppm) 8.92 (1H, m, NH), 7.34–7.35 (1H, m, ArH), 7.23–7.27 (1H, m, ArH), 6.99–7.03 (1H, dd, ArH), 6.48–6.52 (1H, d, ArH), 4.39 (2H, q, OCH₂—), 3.95 (3H, s, CH₃O), 1.39 (3H, t, —CH₃).

Preparation of Methyl 4-methoxyindoline-2(R/S)-carboxylate

Ethyl 4-methoxyindole-2-carboxylate (0.95 g, 4.33 mmol) was dissolved in methanol (10 ml) and magnesium shavings (0.471 g, 19.37 mmol) were then added, with stirring, at room temperature under a nitrogen atmosphere. After the reaction started, a water bath was used to maintain the reaction temperature between 15–20° C. This mixture was stirred overnight. At the end of the reaction, dichloromethane (200 ml) was added to the mixture, followed by ammonium chloride solution (200 ml). The organic phase was separated out and the aqueous phase was extracted with dichloromethane (3×50 ml). The combined organic phases were dried over magnesium sulphate and the solvent was removed to give a brown oil.

¹H-NMR (CDCl₃), δ (ppm) 6.99–7.06 (1H, m, ArH), 6.29–6.40 (2H, dd, ArH), 4.43 (2H, m, H—N, COCHN of the indoline), 3.79 (3H, s, H₃COO), 3.77 (3H, s, H₃CO), 3.28–3.32 (2H, m, CH₂ of the indoline).

Preparation of 4-methoxyindoline-2(R/S)-carboxylic Acid Butylamide

Methyl 4-methoxyindoline-2(R/S)-carboxylate (0.89 g, 4.3 mmol) was dissolved in butylamine (40 ml) under nitrogen and the solution was then stirred at reflux for three hours. After cooling the mixture, the remaining butylamine was removed under vacuum. The crude product was recrystallized from diethyl ether in order to give an off-white solid.

¹H-NMR (CDCl₃), δ (ppm) 7.01–7.09 (2H, m, CONH, ArH), 6.35–6.36 (2H, dd, ArH), 4.35–4.45 (1H, m, COCHN of the indoline), 4.13–4.16 (1H, m, NH of the indoline), 3.79 (3H, s, OCH₃), 3.49–3.63 (1H, m, CH(H) of the indoline), 3.21–3.31 (2H, m, CONCH₂) 2.89–3.01 (1H, m, CH(H) of the indoline), 1.26–1.55 (4H, m, CH₂CH₂), 0.90 (3H, t, CH₃).

Preparation of 1-(benzyloxycarbonyl-2(S)-aminobutyryl)-4-methoxyindoline-2(R/S)-carboxylic Acid Butylamide 4-Methoxyindoline-2(R/S)-carboxylic acid butylamide (0.935 g, 3.77 mmol) and N-benzyloxycarbonyl-2(S)-aminobutyric acid (1.422 g, 6.00 mmol) were dissolved in dry methylene chloride (50 ml). The solution was cooled to 0° C. and triethylamine (1.67 ml, 12 mmol) and bis(2-oxo-3-oxazolidinyl)phosphinyl chloride (1.527 g, 6.00 mmol) were then added. The mixture was stirred at room temperature for 22 hours and then washed with 3N hydrochloric acid (3×50 ml), with 5% sodium bicarbonate (3×50 ml) and with water (50 ml) and dried over sodium sulphate. After removing the solvent, the residue was purified by chromatography on a column of silica gel, using a 3/2 dichloromethane/ethyl acetate mixture as eluent. An off-white solid was obtained.

¹H-NMR (CDCl₃), δ (ppm) 7.73–7.75 (1H, m, CONH), 7.18–7.33 (6H, m, ArH), 6.62–6.73 (2H, m, ArH), 4.82–5.66, 4.18–4.19 (5H, m, PhCH₂, NH of the Abu, 2×COCHN), 3.81 (3H, s, CH₃O), 3.16–3.49 (4H, m, CONCH₂, CH₂ of the indoline), 0.79–1.83 (12H, m, CH₂CH₂CH₃, CH₂CH₃). (Abu=aminobutyryl).

Preparation of 1-(2(S)-aminobutyryl)-4-methoxyindoline-2(R/S)-carboxylic Acid
Butylamide Oxalate: R₁=CH₂CH₃, R=R'=R₉=R₁₀= H, R₈=OCH₃

1-(Benzyloxycarbonyl-2(S)-aminobutyryl)-4-methoxyindoline-2(R/S)-carboxylic acid butylamide (0.100 g, 0.21 mmol) was dissolved in dry methanol (20 ml) and activated palladium-on-charcoal (0.04 g) was added. The mixture was hydrogenated for 2.5 hours at room temperature. The catalyst was removed and oxalic acid (0.020 g, 0.22 mmol) was added to the solution, which was concentrated. Ether was added and an off-white solid was obtained.

Melting point: 117–119° C.

C₁₈H₂₇N₃O₃.1.0(COOH)₂.1.0(H₂O)

required: C, 54.41%; H, 7.08%; N, 9.52%;

found: C, 54.48%; H, 6.87%; N, 9.50%.

¹H-NMR (DMSO-d₆), δ (ppm) 6.5–10.0 (CONHBu, acidic hydrogens), 7.6–7.85, 7.15–7.35, 6.65–6.90 (m, ArH), 4.6–5.5 (1H, m, COCHN of the indoline), 2.5–4.1 (8H, m, CH₃O, CH₂ of the indoline, CONCH₂—, COCHN of the Abu), 0.7–2.2 (12H, m, CH₂CH₂CH₃, CH₂CH₃ of the Abu).

EXAMPLE 28

Route 11

Preparation of Ethyl 2-oxo-3-methylbutanoate

Isopropylmagnesium chloride (2.0M in ether, 200 mmol) was added to a solution of diethyl oxalate (29.23 g, 20.0 mmol) in dry diethyl ether (100 ml) at −70° C. over a period of one hour. The mixture was stirred at −70° C. for a further half an hour and then poured immediately into a vigorously stirred suspension of ice (80 g), diethyl ether (100 ml) and concentrated HCl (18 ml). The aqueous phase was separated out and the organic phase washed with water (100 ml) and then dried (MgSO₄) and the solvent was removed in order to leave the desired product in the form of a colourless oil.

¹H-NMR (CDCl₃), δ (ppm) 4.28 (2H, q, OCH₂), 3.18–3.25 (1H, m, COCH), 1.31 (3H, t, CH₃ of the ethoxy), 1.16 (6H, d, 2×CH₃ of the propyl).

Preparation of Ethyl 2-oxo-3-methylbutanoate Phenylhydrazone

A mixture of ethyl 2-oxo-3-methylbutanoate (23.76 g) and phenylhydrazine (25 ml) was heated at 60° C. in toluene for about one hour, during which time a slight vacuum was used in order to remove the water. After removing the solvent, the residue was chromatographed on silica gel, using a 4/1 petroleum ether/ethyl acetate mixture as eluent, in order to give the desired product in the form of a yellow oil.

¹H-NMR (CDCl₃), δ (ppm) 7.10–7.33 (4H, m, ArH), 6.86–6.98 (1H, m, ArH), 4.28 (2H, q, OCH₂), 2.88–3.06 (1H, m, N=CCH), 1.36 (3H, t, CH₃ of the ethoxy), 1.06 (6H, d, 2×CH₃ of the propyl).

Preparation of Ethyl 3,3-dimethyl-3H-indole-2-carboxylate

Ethanol saturated with hydrochloric acid (320 ml, at a concentration of about 34%) was prepared. Ethyl 2-oxo-3-methylbutanoate phenylhydrazone (compound 65) (20 g, 85.4 mmol) was then added to this solution. The resulting yellow mixture was refluxed for 10 minutes. The mixture was cooled and the ethanol was removed. The residue was added to ether (100 ml) and treated with 5% sodium carbonate until the effervescence ceased. The organic phase was separated out and the aqueous phase was extracted with ether (3×50 ml). The combined organic extracts were washed with water (3×100 ml) until neutral, and were dried (MgSO$_4$). The solvent was removed to leave golden crystals. Recrystallization from petroleum ether at 30° C. gave pale cream crystals.

Melting point: 76–77° C.

$^1$H-NMR (CDCl$_3$), δ (ppm) 7.70–7.80 (1H, m, ArH), 7.34–7.36 (3H, m, ArH), 4.43 (2H, q, OCH$_2$), 1.49 (6H, s, 2×CH$_3$ of the indole), 1.42 (3H, t, CH$_3$ of the ethoxy).

Preparation of Ethyl 3,3-dimethylindoline-2(R/S)-carboxylate

Ethyl 3,3-dimethyl-3H-indole-2-carboxylate (4.00 g, 18.4 mmol) was dissolved in ethanol (20 ml) and activated palladium-on-charcoal (0.5 g) was then added to this solution. This mixture was hydrogenated for five hours. After filtration in order to remove the catalyst, the filtrate was dried (MgSO$_4$) and the solvent removed in order to give a brown oil.

$^1$H-NMR (CDCl$_3$), δ (ppm) 6.94–7.08 (2H, m, ArH), 6.62–6.80 (2H, m, ArH), 4.06–4.34 (4H, m, NH of the indoline, COCHN of the indoline, CH$_2$ of the ethoxy), 1.44 (3H, s, 1×CH$_3$ of the indoline), 1.24 (3H, t, CH$_3$ of the ethoxy), 1.07 (3H, s, 1×CH$_3$ of the indoline).

Preparation of 3,3-dimethylindoline-2(R/S)-carboxylic Acid Butylamide

Butylamine (15 ml) in toluene (40 ml) was cooled to −78° C. and a 2.5M solution of butyllithium in hexane (12.91 ml, 31.5 mmol) was added dropwise. After half an hour, ethyl 3,3-dimethylindoline-2(R/S)-carboxylate (4.600 g, 21 mmol) was added to the solution and this mixture was stirred under nitrogen for three hours. The mixture was then poured into a water/ice mixture (50 ml) and extracted with ethyl acetate; the extracts were dried over magnesium sulphate and the solvent was removed to give a brown oil. This was purified by chromatography on a column of silica gel, using a 7/3 petroleum ether/ethyl acetate mixture as eluent in order to give a yellow solid.

$^1$H-NMR (CDCl$_3$), δ (ppm) 7.02–7.08 (3H, m, 2ArH, CONH), 6.84 (1H, t, ArH), 6.70 (1H, d, ArH), 3.96–4.68 (2H, m, NH of the indoline, COCHN of the indoline), 3.20–3.38 (2H, m, CONCH$_2$), 1.31–1.68 (7H, m, CH$_2$CH$_2$ of the butyl, 1×CH$_3$ of the indoline), 1.08 (3H, s, 1×CH$_3$ of the indoline), 0.90 (3H, t, CH$_3$ of the butyl).

Preparation of 1-(N-benzyloxycarbonyl-2(S)-aminobutyryl)-3,3-dimethylindoline-2(R/S)-carboxylic Acid Butylamide 3,3-Dimethylindoline-2(R/S)-carboxylic acid butylamide (1.000 g, 4.08 mmol) and N-benzyloxycarbonyl-2(S)-aminobutyric acid (1.451 g, 6.12 mmol) were dissolved in dry tetrahydrofuran (25 ml). The solution was cooled to 0° C. and triethylamine (2.44 ml, 13.78 mmol) and bis(2-oxo-3-oxazolidinyl)phosphinyl chloride (2.338 g, 9.183 mmol) were added. The mixture was stirred at room temperature for 22 hours and ethyl acetate (40 ml) was then added, and the mixture was washed with 3N hydrochloric acid (3×50 ml), 5% sodium bicarbonate (3×50 ml) and water (50 ml) and dried over sodium sulphate. After removing the solvent, several successive purifications by chromatography on a column of silica gel gave the product in the form of an off-white solid.

$^1$H-NMR (CDCl$_3$), δ (ppm) 8.08–8.2 (1H, m, CONH), 7.02–7.5 (9H, m, ArH), 4.04–5.82 (5H, m, CH$_2$ of the benzyl, CH, NH of the Abu, COCHN of the indoline), 3.00–3.30 (2H, m, CONCH$_2$), 0.70–1.98 (18H, m, CH$_2$CH$_3$ of the Abu, 2×CH$_3$ of the indoline, CH$_2$CH$_2$CH$_3$ of the butyl).

Preparation of 1-(2(S)-aminobutyryl)-3,3-dimethylindoline-2(R/S)-carboxylic Acid Butylamide Oxalate: R$_1$=CH$_2$CH$_3$, R=R'—32 CH$_3$, R$_8$=R$_9$=R$_{10}$=H 1-(N-Benzyloxycarbonyl-2(S)-aminobutyryl)-3,3-dimethyl-2(R/S)-carboxylic acid butylamide (0.0660 g, 0.142 mmol) was dissolved in dry methanol (6 ml), and activated palladium-on-charcoal (0.022 g) was then added. This mixture was hydrogenated at 60 psi of hydrogen for 2.5 hours at room temperature. After filtration in order to remove the catalyst, oxalic acid (0.013 g, 0.14 mmol) was added to the solution. Most of the methanol was removed by evaporation, ether was then added and an off-white solid precipitated out. This product was collected and dried.

Melting point: 127–133° C.

C$_{19}$H$_{29}$N$_3$O$_2$.1.0(COOH)$_2$.1.0H$_2$O required: C, 57.39%; H, 7.57%; N, 9.56%;

found: C, 57.25%; H, 7.52%; N, 9.70%.

$^1$H-NMR (DMSO-d$_6$), δ (ppm) 8.45–8.75 (1H, m, CONH), 7.99–8.23 (1H, m, ARh), 7.07–7.29 (3H, m, ArH), 4.63–4.83, 3.61–4.00 (2H, m, CH of the Abu, COCHN of the indoline), 3.00–3.16 (2H, m, CONCH$_2$), 0.85–1.88 (18H, m, CH$_2$CH$_3$ of the Abu, CH$_2$CH$_2$CH$_3$ of the butyl, 2×CH$_3$ of the indoline).

EXAMPLE 29
Route 10

Preparation of Ethyl 3-methylindole-2-carboxylate

Phenylhydrazine (14.87 g, 0.137 mol) was mixed with 2-ketobutyric acid (14 g, 0.137 mol) and a solution of sulphuric acid (14 g, 0.142 mol) in absolute ethanol was added shortly afterwards. The crude hydrazone dissolved and the brown solution was maintained under moderate boiling for five hours. The mixture was kept overnight at 4° C. A solid precipitated out. This product was collected and washed with water (30 ml). and alcohol (10 ml) to give an off-white solid.

$^1$H-NMR (CDCl$_3$), δ (ppm) 8.66–8.80 (1H, m, NH), 7.67 (1H, dd, ArH), 7.14–7.36 (3H, m, ArH), 4.42 (2H, q, OCH$_2$), 2.61 (3H, s, CH$_3$ of the indole), 1.43 (3H, t, CH$_3$ of the ester).

Preparation of Methyl 3-(R/S)-methylindoline-2(R/S)-carboxylate

Ethyl 3-methylindole-2-carboxylate (4.06 g, 20 mmol) was dissolved in methanol (50 ml) and magnesium shavings (2.431 g, 100 mmol) were then added with stirring, at room temperature under a nitrogen atmosphere. After the reaction started, a water bath was used to maintain the reaction temperature between 15–20° C. After the end of the reaction, dichloromethane (200 ml) was added to the mixture, followed by NH$_4$Cl solution (200 ml). The organic phase was separated out and the aqueous phase was extracted with dichloromethane (3×50 ml). The combined organic phases were dried over magnesium sulphate and the solvent was removed to give a brown oil.

$^1$H-NMR (CDCl$_3$), δ (ppm) 7.03–7.22 (2H, m, ArH), 6.73–6.78 (2H, m, ArH), 4.48–4.82 (1H, m, H—N), 4.00, 4.50 (1H, dd, COCHN of the indoline), 3.78, 3.77 (3H, S, H$_3$COOC), 3.47–3.70 (1H, m, CH(CH$_3$) of the indoline), 1.44, 1.22 (3H, dd, CH$_3$ of the indoline).

Preparation of 3-(R/S)-methylindoline-2(R/S)-carboxylic Acid Butylamide

Methyl 3-(R/S)-methylindoline-2(R/S)-carboxylate (3.60 g, 18.8 mmol) was dissolved in butylamine (100 ml) under nitrogen and the solution was then stirred at reflux for 3 hours. After cooling the mixture, the remaining butylamine was removed under vacuum. The crude product was purified by chromatography on a column of silica gel, using a 7/3 and then a 5/5 petroleum ether/ethyl acetate mixture as eluent. Two main fractions were collected. The first was a white solid which is the trans isomer.

$^1$H-NMR (CDCl$_3$), δ (ppm) 7.01–7.24 (3H, m, 2ArH, CONH), 6.83 (1H, t, Arh), 6.71 (1H, d, ArH), 4.05–4.07 (1H, m, NH of the indoline), 3.89–3.92 (1H, m, COCHN of the indoline), 3.23–3.27 (3H, m, CH(CH$_3$) of the indoline, CONCH$_2$) 1.43–1.63 (5H, m, CH$_3$ of the indoline, CH$_2$ of the butyl), 1.29–1.37 (2H, m, CH$_2$ of the butyl), 0.90 (3H, t, CH$_3$ of the butyl).

The second was an off-white solid which is the cis isomer.

$^1$H-NMR (CDCl$_3$), δ (ppm) 7.04–7.09 (3H, m, 2ArH, CONH), 6.79–6.83 (1H m, ArH), 6.69 (1H, d, ArH), 4.43–4.47 (1H, dd, COCHN of the indoline), 4.02–4.03 (1H, m, NH of the indoline), 3.67–3.71 (1H, m, CH(CH$_3$) of the indoline), 3.18 3.39 (2H, m, CONCH$_2$) 1.43–1.63 (2H, m, CH$_2$ of the butyl), 1.29–1.37 (2H, m, CH$_2$ of the butyl), 1.12 (3H, d, CH$_3$ of the indoline), 0.90 (3H, t, CH$_3$ of the butyl).

Preparation of 1-(N-benzyloxycarbonyl-2(S)-aminobutyryl)-3(R)-methylindoline-2(R)-carboxylic Acid Butylamide and of 1-(N-benzyloxycarbonyl-2(S)-aminobutyryl)-3(S)-methylindoline-2(S)-carboxylic Acid Butylamide trans-3-Methylindoline-2-carboxylic acid butylamide (0.530 g, 2.284 mmol) and N-benzyloxycarbonyl-2(S)-aminobutyric acid (0.65 g, 2.74 mmol) were dissolved in dry dichloromethane (5 ml). Triethylamine (1.15 ml, 8.224 mmol) and bis(2-oxo-3-oxazolidinyl)phosphinyl chloride (1.047 g, 4.112 mmol) were add ed t o this solution. The mixture was stirred at room temperature for 22 hours, after which it was washed with 3N hydrochloric acid (3×50 ml), with 5% sodium bicarbonate (3×50 ml) and with water (50 ml) and dried over sodium sulphate. After removal of the solvent, chromatography on a column of silica gel, using a 3/2 petroleum ether/ethyl acetate mixture gave the product in the form of an off-white solid.

$^1$H-NMR (CDCl$_3$), δ (ppm) 8.08–8.20 (1H, m, CONH), 6.60–7.55 (9H, m, ArH), 4.60–5.70 (4H, m, CH$_2$ of the benzyl, COCHNH of the Abu), 4.04–4.44 (1H, m, COCHN of the indoline), 2.96–3.78 (3H, m, CH(CH$_3$) of the indoline, CONCH$_2$), 0.70–1.84 (15H, m, CH$_2$CH$_3$ of the Abu, CH$_3$ of the indoline, CH$_2$CH$_2$CH$_3$ of the butyl).

Preparation of 1-(2(S)-aminobutyryl)-3(R)-methylindoline-2(R)-carboxylic Acid Butylamide Oxalate and of 1-(2(S)-aminobutyryl)-3(S)-methylindoline-2(S)-carboxylic Acid Butylamide Oxalate: R$_1$=CH$_2$CH$_3$, R or R'=CH$_3$ and R' or R=H, R$_8$=R$_9$=R$_{10}$=H 1-(N-benzyloxycarbonyl-2(S)-aminobutyryl)-3(R)-methylindoline-2(R)-carboxylic acid butylamide and 1-(N-benzyloxycarbonyl-2(S)-aminobutyryl)-3(S)-methylindoline-2(S)-carboxylic acid butylamide (140 mg, 0.310 mmol) were dissolved in dry methanol (6 ml) and activated palladium-on-charcoal (0.040 g) was then added. This mixture was hydrogenated for 2.5 hours at room temperature. After filtration, oxalic acid (0.028 g, 0.320 mmol) was added to the solution. After removing most of the methanol by evaporation, ether was added. A white solid was obtained.

Melting point: 120.8–125.9° C.

C$_{18}$H$_{27}$N$_3$O$_2$.0.75(COOH)$_2$.1.1H$_2$O, required: C, 57.86%; H, 7.64%; N, 10.36%;

found: C, 57.59%; H, 7.40%; N, 10.21%.

$^1$H-NMR (DMSO-d$_6$), δ (ppm) 8.53–8.57 (1H, m, CONH), 8.03–8.11 (1H, m, ArH), 7.00–7.40 (3H, m, ArH), 4.59–4.81, 3.59–3.88, 2.99–3.38 (5H, m, COCHN of the Abu, 2×CH of the indoline, CONCH$_2$), 1.58–1.85, 1.21–1.45, 0.81–1.08 (15H, m, CH$_2$CH$_3$ of the Abu, CH$_2$CH$_2$CH$_3$ of the butyl, CH$_3$ of the indoline).

EXAMPLE 30

Route 10

Preparation of 1-(N-benzyloxycarbonyl-2(S)-aminobutyryl)-3(R)-methylindoline-2(S)-carboxylic Acid Butylamide and of 1-(2(S)-N-benzyloxycarbonyl-2(S)-aminobutyryl)-3(S)-methylindoline-2(R)-carboxylic Acid Butylamide cis-3-Methylindoline-2-carboxylic acid butylamide (0.220 g, 0.948 mmol) and N-benzyloxycarbonyl-2(S)-aminobutyric acid (0.355 g, 1.50 mmol) were dissolved in dry dichloromethane (5 ml). Triethylamine (0.455 ml, 4.5 mmol) and bis(2-oxo-3-oxazolidinyl)phosphinyl chloride (0.573 g, 2.25 mmol) were added to this solution. The mixture was stirred at room temperature for 22 hours and then washed with 3N hydrochloric acid (3×50 ml), with 5% sodium bicarbonate (3×50 ml) and with water (50 ml) and dried over sodium sulphate. After removing the solvent, the residue was purified by chromatography on a column of silica gel, using a 3/2 petroleum ether/ethyl acetate mixture as eluent. The main fractions were recrystallized from diethyl ether in order to allow an off-white product to be collected.

$^1$H-NMR (CDCl$_3$), δ (ppm) 8.08–8.16 (H, m, CONH), 7.0–7.40 (9H, m, ArH), 4.76–5.98 (4H, m, CH$_2$ of the benzyl, CH, NH of the Abu), 4.18–4.44 (1H, m, COCHN of the indoline), 2.96–3.98 (3H, m, CH(CH$_3$) of the indoline, CONCH$_2$), 0.70–1.94 (15H, m, CH$_2$CH$_3$ of the Abu, CH$_3$ of the indoline, CH$_2$CH$_2$CH$_3$ of the butyl).

Preparation of 1-(2(S)-aminobutyryl)-3(R)-methylindoline-2(S)-carboxylic Acid Butylamide Oxalate and of 1-(2(S)-aminobutyryl)-3(S)-methylindoline-2(R)-carboxylic Acid Butylamide Oxalate: R$_1$=CH$_2$CH$_3$, R or R'=CH$_3$ and R' or R=H, R$_8$=R$_9$=R$_{10}$=H 1-(N-Benzyloxycarbonyl-2(S)-aminobutyryl)-3(R)-methylindoline-2(S)-carboxylic acid butylamide and 1-(N- benzyloxycarbonyl-2(S)-aminobutyryl)-3(S)-methylindoline-2(R)-carboxylic acid butylamide (60 mg, 0.133 mmol) were dissolved in dry methanol (6 ml), and activated palladium-on-charcoal (0.020 g) was then added. This mixture was hydrogenated for 2.5 hours at room temperature. After filtration, oxalic acid (0.013 g, 0.140 mmol) was added to the solution. After removing most of the methanol by evaporation, ether was added and a white solid was obtained.

Melting point: 158.7–162° C.

$C_{18}H_{27}N_3O_2.1.4(COOH)_2.0.7H_2O$, required: C, 54.76%; H, 6.90%; N, 9.22%;

found: C, 54.45%; H, 6.70%; N, 9.54%.

$^1$H-NMR (DMSO-d$_6$), δ (ppm) 8.59–8.60 (1H, m, CONH), 8.06 8.08 (1H, m, ArH), 7.07–7.23 (3H, m, ArH), 5.00 (1H, d, COCHN of the indoline), 3.87–3.91 (1H, m, COCHN of the Abu), 3.60–3.58 (1H, m, CH(CH$_3$) of the indoline), 3.04–3.16 (2H, m, CONCH$_2$), 1.79–1.95 (2H, m, CH$_2$ of the butyl), 1.21–1.44 (m, 7H, CH$_2$ of the butyl, Abu and CH$_3$ of the indoline), 0.98 (3H, t, CH$_3$ of the Abu), 0.870 (3H, t, CH$_3$ of the butyl).

EXAMPLE 31
Route 9

Preparation of Ethyl 2-azido-3-(2-ethoxyphenyl)propenoate

Pieces of sodium (3.678 g, 160 mmol) were added to ethanol (200 ml) over a period of 30 minutes. The resulting solution was cooled to −18° C. and a mixture of 2-ethoxybenzaldehyde (6.007 g, 40 mmol) and ethyl azidoacetate (160 mmol) was then added, over one hour, at a rate which allowed the temperature to be maintained below −15° C. After three hours, the solution was stored at 5° C. for two days in order to give a crystalline product which was collected and washed with cold hexane in order to give an off-white solid.

$^1$H-NMR (CDCl$_3$), δ (ppm) 8.20–8.16 (1H, dd, ArH), 7.44 (1H, s, CH), 7.24–7.33 (1H, m, ArH), 6.84–7.00 (2H, m, ArH), 4.36 (2H, q, OCH$_2$), 4.07 (2H, q, COOCH$_2$), 1.44 (3H, t, CH$_3$ of the ether), 1.39 (3H, t, CH$_3$ of the ester).

This product was recrystallized from methanol to give the methyl ester.

Preparation of Methyl 4-ethoxyindole-2-carboxylate

Methyl 2-azido-3-(2-ethoxyphenyl)propenoate (2.061 g, 10 mmol) was suspended in toluene (500 ml) and the mixture was refluxed for three hours and then maintained at room temperature overnight. The solids were collected by filtration in order to give the desired product in the form of a yellow solid.

$^1$H-NMR (CDCl$_3$), δ (ppm) 8.92 (1H, m, NH), 7.37–7.38 (1H, m, ArH), 7.18–7.26 (1H, m, ArH), 6.94 (1H, d, ArH), 6.49 (1H, d, ArH), 4.18 (2H, q, OCH$_2$), 3.93 (3H, s, CH$_3$O), 1.49 (3H, t, CH$_3$ of the ethoxy).

Preparation of Methyl 4-ethoxyindoline-2(R/S)-carboxylate

Methyl 4-ethoxyindole-2-carboxylate (1.02 g, 4.568 mmol) was dissolved in methanol (20 ml) and magnesium shavings (0.55 g, 22.6 mmol) were then added, with stirring, at room temperature under nitrogen. After the reaction started, a water bath was used to maintain the reaction temperature between 15–20° C. At the end of the reaction, dichloromethane (200 ml) was added to the mixture, followed by NH$_4$Cl solution (200 ml). The organic phase was separated out and the aqueous phase was extracted with dichloromethane (3×50 ml). The combined organic phases were dried over magnesium sulphate and the solvent was removed in order to give a brown oil.

$^1$H-NMR (CDCl$_3$), δ (ppm) 6.96–7.03 (1H, m, ArH), 6.28–6.39 (2H, m, ArH), 4.32–4.44 (2H, m, COCHNH of the indoline), 4.03 (2H, q, OCH$_2$), 3.75 (3H, s, H$_3$COOC), 3.29–3.33 (2H, m, CH$_2$ of the indoline), 1.38 (3H, t, CH$_3$ of the ethoxy).

Preparation of 4-ethoxyindoline-2(R/S)-carboxylic Acid Butylamide

Methyl 4-ethoxyindoline-2(R/S)-carboxylate (0.84 g, 3.8 mmol) was dissolved in butylamine (40 ml), under nitrogen, and the solution was then stirred at reflux for three hours. After cooling the mixture, the remaining butylamine was removed under vacuum. The crude product was purified by chromatography on a column of silica gel, using a 5/5 petroleum ether/ethyl acetate mixture as eluent. A yellow solid was obtained.

$^1$H-NMR (CDCl$_3$), δ (ppm) 6.99–7.05 (2H, m, CONH, ArH), 6.33–6.36 (2H, dd, ArH), 4.36–4.41 (1H, m, COCHN of the indoline), 3.98–4.11 (3H, m, NH, OCH$_2$), 3.52–3.59 (1H, m, CH(H) of the indoline), 3.25 (2H, q, CONCH$_2$), 2.92–2.98 (1H, m, CH(H) of the indoline), 1.27–1.50 (7H, m, CH$_2$CH$_2$ of the butyl, CH$_3$ of the ether), 0.89 (3H, t, CH$_3$ of the butyl).

Preparation of 1-(N-benzyloxycarbonyl)-2(S)-aminobutyryl)-4-ethoxyindoline-2(S)-carboxylic Acid Butylamide 4-Ethoxyindoline-2(R/S)-carboxylic acid butylamide (0.720 g, 2.748 mmol) and N-benzyloxycarbonyl-2(S)-aminobutyric acid (0.787 g, 4.982 mmol) were dissolved in dry methylene chloride (5 ml). The solution was cooled to 0° C. and triethylamine (1.39 ml, 9.947 mmol) and bis(2-oxo-3-oxazolidinyl)phosphinyl chloride (1.268 g, 4.982 mmol) were then added. The mixture was stirred at room temperature for 22 hours and then washed with 3N hydrochloric acid (3×50 ml), with 5% sodium bicarbonate (3×50 ml) and with water (50 ml) and dried over sodium sulphate. After removing the solvent, the product was purified by chromatography on a column of silica gel, using a 3/2 petroleum ether/ethyl acetate mixture as eluent. An off-white product was obtained; this product was recrystallized from diethyl ether.

$^1$H-NMR (CDCl$_3$), δ (ppm) 7.71–7.73 (1H, m, CONH), 7.15–7.37 (6H, m, ArH), 6.59–6.76 (2H, m, ArH), 4.82–5.77 (4H, m, NH of the Abu, CH$_2$Ph, COCHN of the indoline), 3.99–4.21 (3H, m, OCH$_2$ COCHN of the Abu), 3.12–3.49 (4H, m, CH$_2$ of the indoline, CONCH$_2$) 0.79–2.06 (15H, m, CH$_2$CH$_2$CH$_3$ of the butyl, CH$_3$ of. the ethoxy, CH$_2$CH$_3$ of the Abu).

Preparation of 1-(2(S)-aminobutyryl)-4-ethoxyindoline-2(S)-carboxylic Acid Butylamide Oxalate: $R_1=CH_2CH_3$, $R=R'=R_9=R_{10}=H$, $R_8=OC_2H_5$ 1-(N-Benzyloxycarbonyl)-2(S)-aminobutyryl)-4-ethoxyindoline-2(S)-carboxylic acid butylamide (0.135 g, 28.1 mmol) was dissolved in dry methanol and activated palladium-on-charcoal (0.040 g) was then added. This mixture was hydrogenated for 2.5 hours at room temperature. After filtration, oxalic acid (0.0290 g, 32.2 mmol) was added to the solution. Most of the methanol was removed by evaporation and ether was then added. A white solid was obtained.

Melting point: 144.7–146.2° C.

$C_{19}H_{29}N_3O_3.1.0(COOH)_2.1.0H_2O$, required: C, 55.37%; H, 7.30%; N, 9.22%;

found: C, 55.11%; H, 7.09%; N, 9.19%.

$^1$H-NMR (DMSO-$d_6$), δ (ppm) 8.50–8.53 (1H, m, CONHBu), 7.72 (1H, d, ArH), 7.18 (1H, d, ArH), 6.72 (1H, d, ArH), 5.04–5.06 (1H, m, COCHN of the indoline), 4.03–4.06 (2H, m, $CH_2O$), 2.96–3.96 (5H, m, COCHN of the Abu, $CH_2$ of the indoline, $CONCH_2$), 1.75–1.92 (2H, m, $CH_2$ of the butyl), 0.84–1.41 (10H, m, $CH_2CH_3$ of the Abu, butyl).

EXAMPLE 32
Route 9

Preparation of Ethyl 2-azido-3-(2,3-dimethoxyphenyl)propenoate

Pieces of sodium (3.678 g, 160 mmol) were added to ethanol (200 ml) over a period of 30 minutes. The resulting solution was cooled to −18° C. and a mixture of 2,3-dimethoxybenzaldehyde (4.832 g, 40 mmol) and ethyl azidoacetate (20.64 g, 160 mmol) was then added, over one hour, at a rate which allowed the temperature to be maintained below −15° C. After three hours, the solution was stored at 5° C. for two days in order to give a crystalline product which was collected. and washed with cold hexane in order to give a pure product in the form of a yellow oil.

$^1$H-NMR (CDCl$_3$), δ (ppm) 7.78–7.82 (1H, dd, ArH), 7.32 (1H, s, ArCH), 7.04–7.12 (1H, t, ArH), 6.89–6.93 (1H, m, ArH), 4.37 (2H, q, $OCH_2$), 3.86 (3H, s, $OCH_3$), 3.83 (3H, s, $OCH_3$), 1.39 (3H, t, $CH_3$).

Preparation of Ethyl 4,5-dimethoxyindole-2-carboxylate

Ethyl 2-azido-3-(2,3-dimethoxyphenyl)propeneoate (4.0 g, 144 mmol) was suspended in toluene (120 ml) and the mixture was refluxed for three hours and then cooled and stirred at room temperature overnight. The solids were collected by filtration in order to give the product in the form of a yellow solid.

$^1$H-NMR (CDCl$_3$), δ (ppm) 8.76–8.96 (1H, m, NH), 7.30 (1H, dd, ArH), 7.04–7.12 (2H, m, ArH), 4.36 (2H, q, O—CH$_2$—), 4.06 (3H, s, $CH_3O$), 3.86 (3H, s, $CH_3O$), 1.37 (3H, t, —CH$_3$).

Preparation of Methyl 4,5-dimethoxyindoline-2(R/S)-carboxylate

Ethyl 4,5-dimethoxyindole-2-carboxylate (0.500 g, 2 mmol) was dissolved in methanol (10 ml) and magnesium shavings (0.2431 g, 10 mmol) were then added, with stirring, at room temperature under a nitrogen atmosphere. After the reaction started, a water bath was used to maintain the reaction temperature between 5–15° C. At the end of the reaction, dichloromethane (200 ml) was added to the mixture, followed by NH$_4$Cl solution (200 ml). The organic phase was separated out and the aqueous phase was extracted with dichloromethane (3×50 ml). The combined organic phases were dried over magnesium sulphate and the solvent was removed to give a brown oil.

$^1$H-NMR (CDCl$_3$), δ (ppm) 6.64 (1H, d, ArH), 6.38 (1H, d, ArH), 4.28–4.36 (2H, m, NH, COCHN of the indoline), 3.85 (3H, s, $H_3CO$), 3.77, 3.75 (6H, s, $H_3CO$, $H_3COO$), 3.37–3.41 (2H, m, $CH_2$).

Preparation of 4,5-dimethoxyindoline-2(R/S)-carboxylic Acid Butylamide

Methyl 4,5-dimethoxyindoline-2(R/S)-carboxylate (0.447 g, 1.89 mmol) was dissolved in butylamine (35 ml), under nitrogen, and the solution was then stirred at reflux for three hours. After cooling the mixture, the remaining butylamine was removed under vacuum. The crude product was recrystallized from diethyl ether to give an off-white solid.

$^1$H-NMR (CDCl$_3$), δ (ppm) 7.06–7.18 (1H, m, CONH), 6.66 (1H, d, ArH), 6.39 (1H, d, ArH), 4.28–4.44 (1H, m, COCHN of the indoline), 3.59–3.98 (2H, m, NH, CH(H) of the indoline), 3.84 (3H, s, $OCH_3$), 3.79 (3H, s, $OCH_3$), 3.11–3.28 (3H, m, CH(H) of the indoline, $CONCH_2$), 1.30–1.52 (4H, m, $CH_2CH_2$), 0.90 (3H, t, $CH_3$).

Preparation of 1-(N-benzyloxycarbonyl)-2(S)-aminobutyryl)-4,5-dimethoxyindoline-2(R/S)-carboxylic Acid Butylamide 4,5-Dimethoxyindoline-2(R/S)-carboxylic acid butylamide (0.300 g, 1.079 mmol) and N-benzyloxycarbonyl-2 (S)-aminobutyric acid (0.3422 g, 1.444 mmol) were dissolved in dry methylene chloride (10 ml). The solution was cooled to 0° C. and triethylamine (0.49 ml, 3.46 mmol) and bis(2-oxo-3-oxazolidinyl)phosphinyl chloride (0.4409 g, 1.732 mmol) were then added. The mixture was stirred at room temperature for 22 hours and then washed with 3N hydrochloric acid (3×20 ml), with 5% sodium bicarbonate (3×20 ml) and with water (20 ml) and dried over sodium sulphate. After removing the solvent, the residue was purified by chromatography on a column of silica gel, using a 3/2 dichloromethane/ethyl acetate mixture as eluent. An off-white product was obtained.

$^1$H-NMR (CDCl$_3$), δ (ppm) 7.75–7.86 (1H, m, CONH), 7.10–7.35 (5H, m, ArH), 6.73–6.80 (2H, m, ArH), 4.82–5.36 (4H, m, PhCH$_2$, NH of the Abu, COCHN of the indoline), 3.14–4.8 (11H, m, COCHN of the Abu, $CH_2$ of the indoline, 2×$CH_3O$, $CONCH_2$), 0.78–1.80 (12H, m, $CH_2CH_2CH_3$ of the butyl, $CH_2CH_3$ of the Abu).

Preparation of 1-(2(S)-aminobutyryl)-4,5-dimethoxyindoline-2(R/S)-carboxylic Acid Butylamide Oxalate: $R_1=CH_2CH_3$, R=R'=$R_{10}$, =H, $R_8=R_9=OCH_3$ 1-(Benzyloxycarbonyl)-2(S)-aminobutyryl)-4,5-dimethoxyindoline-2(R/S)-carboxylic acid butylamide (0.100 g, 0.20 mmol) was dissolved in dry methanol (10 ml), and activated palladium-on-charcoal (0.038 g) was then added. This mixture was hydrogenated for 2.5 hours at room temperature. After filtration, oxalic acid (0.020 g, 0.22 mmol) was added to the solution. Most of the methanol was removed by evaporation and ether was then added. An off-white solid was obtained.

Melting point: 196.1–197.5° C.

$C_{19}H_{29}N_3O_4.1.0(COOH)_2.1.0H_2O$, required: C, 53.49%; H, 7.05%; N, 8.91%;

found: C, 53.46%; H, 6.89%; N, 8.80%.

$^1$H-NMR (DMSO-$d_6$), δ (ppm) 8.48–8.52 (1H, m, CONHBu), 7.79 (1H, d, ArH), 6.90 (1H, d, ArH), 5.03–5.06 (1H, m, COCHN of the indoline), 3.57–3.77 (8H, m, 2×$CH_3O$, CH(H) of the indoline, COCHN of the Abu), 3.08–3.12 (3H, m, $CONCH_2$, CH(H) of the indoline), 1.77–1.93 (2H, m, $CH_2$ of the Abu), 1.25–1.42 (4H, m, CH$_2$CH$_2$ of the butyl), 0.85–1.04 (6H, m, CH$_3$ of the Abu, CH$_3$ of the butyl).

EXAMPLE 33
Route 12

Preparation of 1-(N-benzyloxycarbonyl)-2(S)-aminobutyryl)-5-benzyloxyindoline-2(R/S)-carboxylic Acid Butylamide 5-Benzyloxyindoline-2(R/S)-carboxylic acid butylamide (0.648 g, 2 mmol), N-benzyloxycarbonyl-2(S)-aminobutyric acid (0.521 g, 2.2 mmol) and dicyclohexylcarbodiimide (2.2 mmol) were dissolved in dichloromethane (70 ml) and stirred for 18 h. The mixture was washed with NaHCO$_3$ solution, the washing waters were extracted with ethyl acetate and the combined organic fractions were dried (Na$_2$SO$_4$). The solvent was removed to give a solid which was purified by chromatography on a column of silica gel, using a 1/1 ethyl acetate/petroleum ether mixture, in order to give the (S/S) diastereoisomer alone and the (S/S and S/R) diastereoisomers combined.

NMR δ=8.00–8.03 (1H, m, NH), 7.24–7.40 (10H, m, 2×Ph), 6.78–6.90 (3H, m, ArH), 4.78–5.34 (6H, m, 2×PhCH$_2$, NCHCO of the Abu, NH), 4.3–4.18 (1H, m, NCHCO of the indoline), 3.43–3.49 (2H, m, CH$_2$ of the indoline) 3.14–3.18 (2H, m, CONHCH$_2$) 0.77–1.93 (12H, m, 2×CH$_3$, 3×CH$_2$).

Preparation of 1-(2(S)-aminobutyryl)-5-hydroxyindoline-2(S)-carboxylic Acid Butylamide Oxalate: R$_1$=CH$_2$CH$_3$, R=R'=R$_8$=R$_{10}$=H, R$_9$=OH N-benzyloxycarbonyl-2(S)-aminobutyryl-5-benzyloxyindoline-2(S)-carboxylic acid butylamide (200 mg, 0.36 mmol) was dissolved in methanol (20 ml) and treated with activated palladium-on-charcoal (80 mg). The mixture was hydrogenated at 80 psi for 2.5 h. The catalyst was removed by filtration and the amount of solvent reduced. Oxalic acid (36 mg) was added, followed by ether, in order to give the product in the form of a white solid.

Melting point: 156.5–158° C.

C$_{17}$H$_{25}$N$_3$O$_3$.1.1(COOH)$_2$.0.3H$_2$O.0.5(C$_2$H$_5$)$_2$O,
required: C, 55.23%; H, 7.19%; N, 9.12%;
found: C, 54.99%; H, 7.29%; N, 9.08%.

NMR d=8.42–8.43 (1H, m, NH), 7.91 (1H, d, ArH), 6.57–6.70 (2H, m, ArH), 5.59–4.87 (1H, m, NCHCO of the Abu), 3.55–3.59 (1H, m, NCHCO of the indoline), 3.33–3.44 (2H, m, CONCH$_2$), 3.00–3.16 (2H, m, CH$_2$ of the indoline), 0.84–1.87 (12H, m, 3×CH$_2$, 2×CH$_3$).

EXAMPLE 34
Route 12

Preparation of 1-2(S)-aminobutyryl-5-hydroxyindoline-2(R/S)-carboxylic Acid Butylamide Oxalate: R$_1$=CH$_2$CH$_3$, R=R'=R$_8$=R$_{10}$=H, R$_9$=OH The above procedure was repeated with N-benzyloxycarbonyl-2(S)-aminobutyryl-5-benzyloxyindoline-2(R/S)-carboxylic acid butylamide (100 mg, 0.18 mmol) in order to give the desired product.

Melting point: 129–130° C.

C$_{17}$H$_{25}$N$_3$O$_3$.0.9(COOH)$_2$.0.5H$_2$O.0.3(C$_2$H$_5$)$_2$O,
required: C, 55.63%; H, 7.20%; N, 9.74%;
found: C, 55.44%; H, 7.31%; N, 9.73%.

NMR δ=8.43–8.44 (1H, m, CONH), 7.86–7.94 (1H, d, ArCH), 6.58–6.67 (2H, m, ArCH), 4.93–5.20 (1H, m, NCHCO of the Abu), 3.36–3.81 (2H, m, NCHCO of the indoline, CH(H) of the indoline), 2.90–3.11 (3H, m, CH(H) of the indoline, CONHCH$_2$), 0.84–1.74 (12H, m, 3×CH$_2$, 2×CH$_3$).

EXAMPLE 35
Route 8

Preparation of Methyl 5-methylindole-2-carboxylate

5-Methylindole-2-carboxylic acid (0.9 g, 5.13 mmol) was dissolved in methanol (25 ml) and treated with sulphuric acid (0.5 ml). The mixture was refluxed for 4 h. The volume of solvent was reduced and the residue treated with sodium hydrogen carbonate solution and extracted with ethyl acetate. The organic fractions were dried and concentrated to give the desired ester.

Preparation of Methyl 5-methylindoline-2(R/S)-carboxylate

Methyl 5-methylindole-2-carboxylate (0.95 g, 5 mmol) and magnesium shavings (0.62 g, 25 mmol) were suspended in methanol (25 ml) and the mixture was stirred at 15° C. for 2 h. The mixture was filtered, diluted with methylene chloride (100 ml) and washed with NH$_4$Cl solution. The organic phase was dried (Na$_2$SO$_4$) and the solvent removed to give the crude product, which was purified by chromatography on a column of silica gel, using a 7/3 petroleum/ethyl acetate mixture as eluent.

NMR δ=6.63–6.93 (3h, M, ArCH), 4.33–4.41 (1H, m, NCHCO), 3.75 (3H, s, CH$_3$O), 3.29–3.36 (2H, m, CH$_2$), 2.24 (3H, s, CH$_3$Ar)

Preparation of 5-methylindoline-2 (R/S)-carboxylic Acid Butylamide

Methyl 5-methylindoline-2(R/S)-carboxylate (0.3 g, 4.18 mmol) was dissolved in butylamine (20 ml) and the mixture was refluxed for 4 h under nitrogen. The excess amine was removed under vacuum to give a solid, which was recrystallized from ether in order to allow the product to be collected.

NMR δ=6.60–6.90 (3H, m, ArCH), 4.21–4.33 (2H, m, CONH, NCHCO), 3.43–3.48 (1h, m, CH(H) of indoline), 3.22–3.28 (2H, m, NCH$_2$), 3.02–3.18 (1H, m, CH(H) of indoline), 2.24 (3H, s, CH$_3$Ar), 1.29–1.50 (4H, m, 2×CH$_2$), 0.86–0.93 (3H, m, CH$_3$).

Preparation of 1-N-benzyloxycarbonyl-2(S)-aminobutyryl-5-methylindoline-2(R/S)-carboxylic Acid Butylamide Triethylamine (0.84 ml) and bis(2-oxo-3-oxazolidinyl) phosphinyl chloride (0.76 g) were added to a solution of 5-methylindolinecarboxylic acid butylamide (0.46 g, 2 mmol) and N-benzyloxycarbonyl-2(S)-aminobutyric acid in dichloromethane (10 ml), under nitrogen. The mixture was stirred at room temperature for 20 hours. The solution was washed with saturated NH$_4$Cl solution and with water. The combined aqueous fractions were extracted with methylene chloride. The combined organic fractions were dried and the solvent was removed to give a yellow oil which was purified by chromatography on a column of silica gel, using a 7/3 ether/petroleum mixture as eluent. The desired product was obtained in the form of an off-white solid.

NMR δ=7.97–8.00 (1H, m, NH), 7.24–7.38 (5H, m, ArCH), 6.89–7.07 (3H, m, ArCH), 4.79–5.31 (4H, m,

PhCH$_2$, NH, NCHCO of the Abu), 4.00–4.40 (1H, m, NCHCO of indoline), 3.42–3.57 (2H, m, CONHCH$_2$), 3.09–3.22 (2h, m, CH$_2$ of indoline), 2.29 (3H, s, CH$_3$Ar), 0.80–2.26 (12H, m, 3×CH$_2$, 2×CH$_3$).

Preparation of 1-2(S)-aminobutyryl-5-methylindoline-2(R/S)-carboxylic Acid Butylamide Oxalate: R$_1$=CH$_2$CH$_3$, R=R'=R$_8$=R$_{10}$=H, R$_9$=CH$_3$ 1-N-Benzyloxycarbonyl-2(S)-aminobutyryl-5-methylindoline-2(R/S)-carboxylic acid butylamide (130 mg) was dissolved in methanol (12 ml) and treated with activated palladium-on-charcoal (40 mg). The mixture was hydrogenated at 60 psi for 2.5 h. The catalyst was removed by filtration and the volume of solvent was reduced. This mixture was treated with oxalic acid (28.8 mg) and ether in order to give the desired product.

Melting point: 110–2° C.

C$_{18}$H$_{27}$N$_3$O$_2$.(COOH)$_2$.0.1 H$_2$O required: C, 58.70%; H, 7.19%; N, 10.27%;

found: C, 58.83%; H, 7.20%; N, 9.88%.

NMR δ=8.45–8.46 (1H, m, CONH), 7.90–7.99 (1H, m, ArCH), 7.33–7.35 (2H, m, ArCh), 7.00–7.06 (1H, m, NH), 4.97–5.02 (2H, m, NCHCO of the Abu, NH), 3.55–3.90 (5H, m, CONHCH$_2$, NCHCO and CH$_2$ of indoline), 2.23, 2.25 (3H, s, CH$_3$—Ar), 0.8–2.0 (12H, m, 3×CH$_2$, 2×CH$_3$).

EXAMPLE 36

Route 13

Preparation of Methyl 5-chloroindole-2-carboxylate

5-Chloroindole-2-carboxylic acid (0.95 g, 4.65 mmol) was dissolved in methanol (35 ml) and treated with sulphuric acid (0.5 ml). The mixture was refluxed for 5 h and cooled and the solvent was removed. The residue was recrystallized twice from methanol to give the product.

Preparation of Methyl 5-chloroindoline-2(R/S)-carboxylate

Methyl 5-chloroindole-2-carboxylate (0.6 g, 2.87 mmol) and magnesium shavings (0.34 g, 14.3 mmol) were suspended in methanol (40 ml) and the mixture was stirred for 8 h. The mixture was filtered, treated with methylene chloride (100 ml) and washed with NH$_4$Cl solution. The organic fraction was dried (Na$_2$SO$_4$) and the solvent removed in order to give a solid which was purified by chromatography on a column of silica gel, using a 7/3 petroleum/ethyl acetate mixture as eluent. The product was isolated in the form of a yellow solid.

Preparation of 5-chloroindoline-2(R/S)-carboxylic Acid Butylamide

Methyl 5-chloroindoline-2(R/S)-carboxylate (0.63 g, 3 mmol) was dissolved in butylamine (25 ml) and refluxed for 4 h. The excess amine was removed and the residue was crystallized from ether to give a yellow solid.

Preparation of 1-N-t-butoxycarbonyl-2(S)-aminobutyryl-5-chloroindoline-2(S)-carboxylic Acid Butylamide 5-Chloroindoline-2(R/S)-carboxylic acid butylamide (0.52 g, 2 mmol) and N-t-butoxycarbonyl-2(S)-aminobutyric acid (0.45 g, 2.2 mmol) were dissolved in methylene chloride (20 ml) and treated with bis(2-oxo-3-oxazolidinyl)phosphinyl chloride (0.64 g, 2.5 mmol) and triethylamine (0.5 g, 5 mmol). The mixture was stirred at room temperature for 12 h and then washed with 10% citric acid (3×50 ml), with 5% NaHCO$_3$ (3×50 ml) and with water (50 ml). The organic phase was dried and concentrated. The residue was purified by chromatography to give the product.

Preparation of 1-(2(S)-aminobutyryl)-5-chloroindoline-2(S)-carboxylic Acid Butylamide Trifluoroacetate: R$_1$=CH$_2$CH$_3$, R=R'=R$_8$=R$_{10}$=H, R$_9$=Cl 1-N-t-butoxycarbonyl-2(S)-aminobutyryl-5-chloroindoline-2(R/S)-carboxylic acid butylamide (50 mg, 0.114 mmol) was dissolved in trifluoroacetic acid (2 ml) and methylene chloride (2 ml) and maintained at room temperature for 40 minutes. Evaporation of the solvents and addition of diethyl ether gave the product.

Melting point: 83–84° C.

C$_{17}$H$_{24}$N$_3$O$_2$Cl.1.5 CF$_3$COOH, required: C, 47.21%; H, 5.05%; N, 7.85%;

found: C, 47.43%; H, 5.24%; N, 8.42%.

NMR δ=8.07–8.09 (1H, d, ArH), 7.27–7.36 (2H, m, ArH), 5.03–5.06 (1H, m, NCHCO de l'Abu), 3.59–3.70 (2H, m, NCHCO of the indoline, CH(H) of the indoline), 3.06–3.12 (3H, m, CH(H) of the indoline, CONHCH$_2$), 1.77–1.94 (2H, m, CH$_2$ de l'Abu), 1.24–1.43 (4H, m, CH$_2$CH$_2$CH$_3$), 0.83–1.58 (6H, m, 2×CH$_3$).

EXAMPLE 37

Route 14

Preparation of Methyl Indoline-2(S)-carboxylate

Indoline-2(S)-carboxylic acid (10 g, 64 mmol) was refluxed in a mixture of methanol (50 ml) and sulphuric acid (8 ml) for 5 h. The solvent was removed to give the product in the form of an oil.

Preparation of Methyl 1-(N-t-butoxycarbonyl-2(S)-aminobutyryl)indoline-2(S)-carboxylate Triethylamine (3.15 ml) and bis(2-oxo-3-oxazolidinyl) phosphinyl chloride (5.75 g, 22.6 mmol) were added to a solution of methyl indoline-2-carboxylate (2 g, 11.3 mmol) and N-t-butoxycarbonyl-2(S)-aminobutyric acid (2.6 g, 13.6 mmol) in methylene chloride (15 ml), at 0° C. under nitrogen. The reaction was stirred for 2 h at 5° C. and then at room temperature overnight. The mixture was filtered, the filtrate was washed with water (2×40 ml) and the combined aqueous fractions were extracted with methylene chloride. The combined organic fractions were dried and concentrated to give a residue, which was purified by chromatography on a column of silica gel, using a 7/3 petroleum ether/ethyl acetate mixture as eluent. The product was obtained in the form of a white solid.

1-(N-t-butoxycarbonyl-2(S)-aminobutyryl)-indoline-2(S)-carboxylic Acid (3-hydroxy)propylamide Methyl 1-(N-t-butoxycarbonyl-2(S)-aminobutyryl) indoline-2(S)-carboxylate (0.36 g, 1 mmol) was dissolved in methanol (10 ml) and treated, under nitrogen and at 50° C., with 3-hydroxypropylamine (10 ml). The mixture was stirred at 50° C. for 3 h and the solvent was evaporated off. The residue was dissolved in methylene chloride (30 ml) and washed with 1M KHSO$_4$. The organic phase was dried (Na$_2$SO$_4$) and evaporated. The residue was purified by column chromatography in order to give the product.

1-(2(S)-Aminobutyryl)indoline-2(S)-carboxylic Acid (3-hydroxy)propylamide Trifluoroacetate: $R_1=CH_2CH_3$, $R_2=H$, $R=R'=R_8=R_9=R_{10}=H$, n= and m= 1, $R_3=$

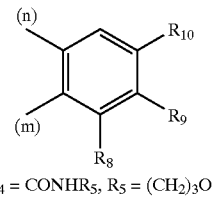

$R_4 = CONHR_5$, $R_5 = (CH_2)_3OH$ 1-(N-t-Butoxycarbonyl)-2(S)-aminobutyryl)-indoline-2(S)carboxylic acid (3-hydroxy)propylamide (0.12 g) was dissolved in methylene chloride (1 ml) and treated with trifluoroacetic acid (1 ml). The solution was stirred at room temperature for 20 minutes and the solvents were removed in order to give an oil. Addition of ether and filtration gave the product in the form of. a solid.

Melting point: 86–88° C.

$C_{16}H_{23}N_3O_3 \cdot 1.5\ CF_3COOH$, required: C, 47.97%; H, 5.11%; N, 8.67%;

calculated: C, 47.90%; H, 5.18%; N, 8.82%.

NMR δ: 8.11 (1H, d, ArH), 7.05–7.29 (3H, m, ArH), 5.02–5.04 (NCHCO de l'Abu) 4,37–4.65 (NCHCO of indoline, OH), 3.62–3.68 (2H, m, $CH_2OH$), 3.34–3.42 (1H, m, CH(H) of the indoline), 3.09–3.21 (3H, m, CH(H) of the indoline, $CONHCH_2$), 1.56–1.94 (4H, m, $CH_2CH_2OH$, $CH_2CH_3$), 0.94–1.1 (3H, m, $CH_3$).

Measurement of the Activity of Membrane-bound Tripeptidylpeptidase

After isolating and characterizing the abovementioned membrane-bound tripeptidylpeptidase, the inventors devised a measurement of its activity, described below.

Membranes from rat brain were obtained by centrifugation (200,000×g min) of a homogenate prepared in 10 volumes of 50 mM potassium phosphate buffer, pH 7.4.

After washing thoroughly, the centrifugation pellet is taken up in the buffer containing 10% glycerol and 0.1% Brij 35 in order to obtain a concentration of 25 mg of proteins/ml.

After preincubation for 25 minutes, the incubations are carried out for 15 minutes at 37° C. in the buffer in a volume of 0.1 ml containing 0.1% Brij 35, 100 mM bestatin, 25 μg of membrane and 50 μM of substrate (A-AP-Amc). The release of Amc is evaluated by fluorimetry.

DEVELOPMENT OF INHIBITORS

The effect of the compounds according to the invention given above as examples was evaluated by measuring the activity of membrane-bound tripeptidylpeptidase II. The inhibitory power of these compounds was expressed by their apparent dissociation constant (Ki), calculated from the values of their 50% inhibitory concentration and from the $K_M$ of the substrate (23 μM).

Table II below reports a series of characteristic values for the compounds according to the invention.

TABLE II

INHIBITION OF THE ACTIVITY OF MEMBRANE-BOUND AMINOTRIPEPTIDYLPEPTIDASE FROM BRAIN

| Example No. | Ki μm |
|---|---|
| 1 | 0.9 |
| 2 | 0.3 |
| 3 | 0.270 |
| 4 | 0.10 |
| 5 | 0.5 |
| 6 | 0.080 |
| 7 | 0.320 |
| 8 | 0.57 |
| 9 | 0.00030 |
| 10 | 0.00030 |
| 11 | 0.320 |
| 12 | 0.140 |
| 13 | 0.040 |
| 14 | 0.0052 |
| 15 | 0.0060 |
| 16 | 0.340 |
| 17 | 0.012 |
| 18 | 0.008 |
| 19 | 0.077 |
| 20 | 0.012 |
| 21 | 1.0 |
| 22 | 0.560 |
| 23 | 0.143 |
| 2 (S)-aminobutyryl-L-prolineamide* | known 0.57 |
| (S,S) isomer | 20 0.003 |
| (S,R) isomer | 20 0.233 |
| (S,S) isomer | 18 0.006 |
| (S,R) isomer | 18 0.241 |
| 24 | 0.146 |
| 25 | 0.026 |
| 26 | 0.0075 |
| 27 | 0.014 |
| 28 | 0.864 |
| 29 | 0.593 |
| 30 | 0.032 |
| 31 | 0.029 |
| 32 | 0.0096 |
| 33 | 0.0066 |
| 34 | 0.0104 |
| 35 | 0.0226 |
| 36 | 0.0025 |
| 37 | 0.0124 |

*$R_1 = CH(CH_3)_2$; $R_2 = H$; n = 0 or 1 and m = 0 or 1 with n being different from m; R = R' = H; $R_3 = —(CH_2)_2—$; $R_4 = CO—NH-R_5$; $R_5 = H$ Noteworthy effects were demonstrated for the compounds according to the invention, in particular for the compounds having an indoline skeleton. It is significant to note that the compound of Example 22, for example, has a protective effect on endogenous CCK-8 on slices of depolarized rat cerebral cortex, demonstrated according to the method of Rose et al. (Proc. Natl. Acad. Sci. USA, 1988, 85: 8326). At a concentration of 1 μM, it multiplies the recovery of released CCK-8 4-fold (measured by radioimmunoassay).

The anorexigenic activity (pro-satiety) of this same compound is demonstrated in rodents. In mice, at a dose of 10 mg/kg (intravenously), this compound decreases the spontaneous taking of solid food ("UAR" tablet) by 45%, measured over a period of 30 to 90 minutes after free access to this food (period preceded by fasting overnight and oral administration of 0.2 ml of a semi-liquid meal).

This test is completed by an evaluation of the inhibitory activity of TPP II "ex vivo", which consists in administering a compound according to the invention to a rodent and in measuring the residual catalytic activity on membranes from brain or from a peripheral organ.

For example, the activity of liver TPP II measured in mice 90 minutes after oral administration of 10 mg/kg of the compound of Example 9 is about 90–100% inhibited.

What is claimed is:

1. A compound selected from the group consisting of a compound of the formula

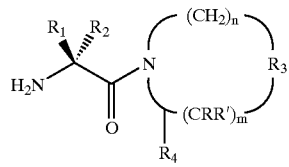

I wherein $R_1$ is hydrogen or alkyl of 1 to 4 carbon atoms, $R_2$ is hydrogen or alkyl of 1 to 2 carbon atoms with at least one of $R_1$ and $R_2$ being hydrogen, n is 0 or 1, m is 0 or 1 with n being different from m, R and R' are individually hydrogen or alkyl of 1 to 2 carbon atoms, $R_3$ is selected from the group consisting of

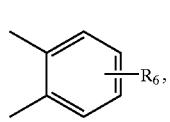 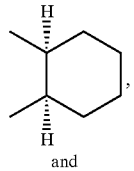 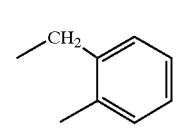

and

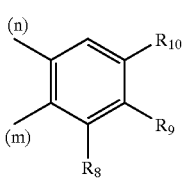

$R_6$ is selected from the group consisting of hydrogen, —F, —OCH$_3$ and benzyloxyl, $R_8$, $R_9$ and $R_{10}$ are individually selected from the group consisting of hydrogen, halogen, alkoxy of 1 to 4 carbon atoms, benzyloxy, —OH and alkyl of 1 to 4 carbon atoms, m and n indicating the bond orientation with respect to —(CH$_2$)$_n$— or to N if n is 0 and to (—CRR')$_m$ or to —CHR$_4$— if m is 0, $R_4$ is

$R_5$ is selected from the group consisting of hydrogen, alkyl of 1 to 6 carbon atoms, —(CH$_2$)$_3$—SCH$_3$, benzyl, cyclohexylmethyl, —(CH$_2$)$_3$—OH

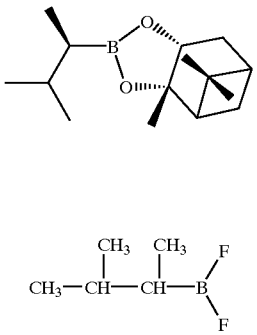

and

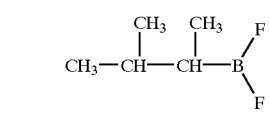

or a salt thereof, or a hydrate thereof.

2. A compound of claim 1 having the formula

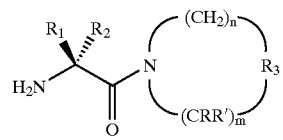

I' wherein $R_1$ is hydrogen or alkyl of 1 to 4 carbon atoms, $R_2$ is alkyl of 1 to 2 carbon atoms or hydrogen, at least one of $R_1$ and $R_2$ being hydrogen, n is 0 or 1 m is 0 or 1 and n and m are different, $R_3$ is selected from the group consisting of

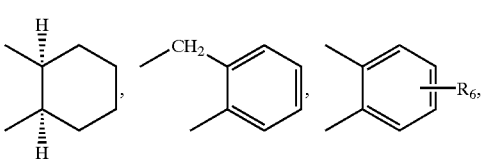

$R_6$ is selected from the group consisting of hydrogen, —F, —OCH$_3$ and benzyloxy, $R_4$ is

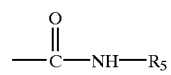

and $R_5$ is selected from the group consisting of hydrogen, alkyl of 1 to 6 carbon atoms, —(CH$_2$)$_3$—SCH$_3$, benzyl, cyclohexylmethyl

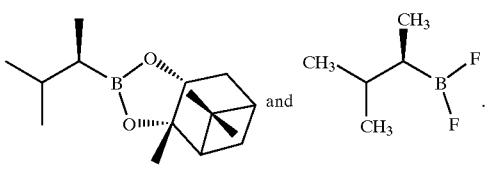

.

3. A compound of claim 1 wherein n is 0 and m is 1.
4. A compound of claim 3 wherein $R_3$ is

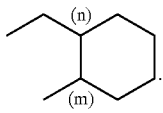

5. A compound of claim 3 wherein R and R' represent hydrogen and $R_3$ is

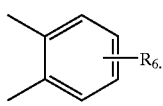

6. A compound of claim 3 wherein $R_3$ is

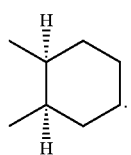

7. A compound of claim 3 wherein $R_3$ is

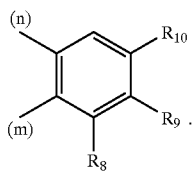

8. A compound of claim 1 wherein n is 1 and m is 0.
9. A compound of claim 8 wherein $R_3$ is

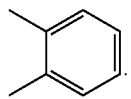

10. A compound of claim 1 wherein $R_5$ is n-butyl.
11. A compound of claim 1 wherein $R_5$ is hydrogen.
12. A compound of claim 1 wherein $R_1$ is hydrogen.
13. A compound of claim 1 selected from the group consisting of 2-(2(S)-aminobutyryl)-1,2,3,4-tetrahydro-3(S)-isoquinolinecarboxylic acid n-butylamide;
1-(2(S)-aminobutyryl)-2(S)-indolinecarboxylic acid n-butylamide;
1-(2(S)-aminobutyryl)-2(S)-indolinecarboxylic acid n-propylamide;
1-(2(S)-aminobutyryl)-2(S)-indolinecarboxylic acid methylamide;
1-(2(S)-aminobutyryl-2(S)-indolinecarboxylic acid ethylamide;
1-(2(S)-aminobutyryl)-2(R/S)-(5-methoxy) indolinecarboxylic acid n-butylamide;
1-(2(S)-aminobutyryl)-2(R/S)-(6-methoxy) indolinecarboxylic acid n-butylamide;
1-(2(S)-aminobutyryl)-2(R/S)-(5-fluoro)indolinecarboxylic acid n-butylamide;
1-(2(S)-aminobutyryl)-2(R/S)-(5-benzyloxy) indolinecarboxylic acid n-butylamide;
1-(2(S)-aminobutyryl)-2(S)-[(3aS,7aS)-perhydro] indolinecarboxylic acid n-butylamide;
2-(2(S)-aminobutyryl)-1(R/S)-isoindolinecarboxylic acid n-butylamide; and the corresponding salts or hydrates thereof.

14. A compound of claim 13 selected from the group consisting of 1-(2(S)-aminobutyryl)-2(S)-indolinecarboxylic acid n-butylamide;
1-(2(S)-aminobutyryl)-2(S)-indolinecarboxylic acid n-propylamide;
1-(2(S)-aminobutyryl)-2(S)-indolinecarboxylic acid ethylamide;
1-(2(S)-aminobutyryl)-2(R/S)-(5-methoxy) indolinecarboxylic acid n-butylamide;
1-(2(S)-aminobutyryl)-2(R/S)-(5-fluoro)indolinecarboxylic acid n-butylamide and the corresponding salts or hydrates thereof.

15. A compound of claim 1 selected from the group consisting of 1-(L-valyl)-5-methoxyindoline-2(R/S)-carboxylic acid butylamide;
1-(L-alanyl)-5-methoxyindoline-2(R/S)-carboxylic acid butylamide;
1-(L-alanyl)-5-methoxyindoline-2(S)-carboxylic acid butylamide;
1-(2(S)-aminobutyryl)-4-methoxyindoline-2(R/S)-carboxylic acid butylamide;
1-(2(S)-aminobutyryl)-3,3-dimethylindoline-2(R/S)-carboxylic acid butylamide;
1-(2(S)-aminobutyryl)-3(R)-methylindoline-2(R)-carboxylic acid butylamide and 1-(2(S)-aminobutyryl)-2(S)-methylindoline-2(S)-carboxylic acid butylamide;
1-(2(S)-aminobutyryl)-3 (R)-methylindoline-2(S)-carboxylic acid butylamide and 1-(2(S)-aminobutyryl)-3(S)-methylindoline-2(R)-carboxylic acid butylamide;
1-(2(S)-aminobutyryl)-4-ethoxyindoline-2(S)-carboxylic acid butylamide;
1-(2(S)-aminobutyryl)-4,5-dimethoxyindoline-2(R/S)-carboxylic acid butylamide;
1-(2(S)-aminobutyryl)-5-hydroxyindoline-2(S)-carboxylic acid butylamide;
1-(2(S)-aminobutyryl)-5-hydroxyindoline-2(R/S)-carboxylic acid butylamide;
1-(2(S)-aminobutyryl)-5-methylindoline-2(R/S)-carboxylic acid butylamide;
1-(2(S)-aminobutyryl)-5-chloroindoline-2(S)-carboxylic acid butylamide; and
1-(2(S)-aminobutyryl)indoline-2(S)-carboxylic acid (3-hydroxy)propylamide;

or a salt or hydrate thereof.

16. A method of inhibiting the enzymatic hydrolysis of cholecystokinin in a warm-blooded animal comprising administering to a warm-blooded animal a compound of claim 1 for a time and under conditions effective to inhibit aminotripeptidylpeptidase.

17. A method of suppressing appetite in a warm-blooded animal comprising administering to a warm-blooded animal a compound of claim 1 for a time and under conditions effective to suppress appetite in said animals.

* * * * *

UNITED STATES PATENT AND TRADEMARK OFFICE
CERTIFICATE OF CORRECTION

PATENT NO. : 6,403,561 B1
DATED : June 11, 2002
INVENTOR(S) : Rose et al.

Page 1 of 1

It is certified that error appears in the above-identified patent and that said Letters Patent is hereby corrected as shown below:

<u>Title page,</u>
After Item "(87)   PCT Pub.No. : WO96/35805
                PCT Pub. Date:  Nov. 14, 1996", please insert
-- [30]  Foreign Application Priority Data
May 9, 1995     (FR)    France…………...95 05489 --

Signed and Sealed this

Fifteenth Day of October, 2002

*Attest:*

JAMES E. ROGAN
*Attesting Officer*      *Director of the United States Patent and Trademark Office*